(12) United States Patent
Blais et al.

(10) Patent No.: US 8,309,096 B2
(45) Date of Patent: Nov. 13, 2012

(54) FUSION PROTEIN

(75) Inventors: Normand Blais, West Laval (CA); Martine Boyer, West Laval (CA); Vincent Brichard, Rixensart (BE); Jamila Louahed, Rixensart (BE); Denis Martin, West Laval (CA); Remi Palmantier, West Laval (CA); Clement Rioux, West Laval (CA)

(73) Assignee: GlaxoSmithKline Biologicals S.A., Rixensart (BE)

( * ) Notice: Subject to any disclaimer, the term of this patent is extended or adjusted under 35 U.S.C. 154(b) by 508 days.

(21) Appl. No.: 12/503,468

(22) Filed: Jul. 15, 2009

(65) Prior Publication Data

US 2010/0029912 A1 Feb. 4, 2010

Related U.S. Application Data

(63) Continuation-in-part of application No. PCT/US2008/050879, filed on Jan. 11, 2008.

(60) Provisional application No. 60/914,925, filed on Apr. 30, 2007, provisional application No. 60/914,848, filed on Apr. 30, 2007.

(30) Foreign Application Priority Data

Jan. 15, 2007 (GB) .................................. 0700759.4
May 21, 2007 (GB) .................................. 0709707.4

(51) Int. Cl.
*A61K 39/00* (2006.01)
*A61K 38/00* (2006.01)
*C07K 1/00* (2006.01)

(52) U.S. Cl. ............... 424/192.1; 424/185.1; 424/277.1; 424/184.1; 514/1.1; 530/350; 530/828

(58) Field of Classification Search ........................ None
See application file for complete search history.

(56) References Cited

U.S. PATENT DOCUMENTS

| 5,804,381 | A | 9/1998 | Chen et al. |
| 6,140,050 | A | 10/2000 | Sahin et al. |
| 6,242,052 | B1 | 6/2001 | Hilger et al. |
| 6,251,603 | B1 | 6/2001 | Jager et al. |
| 6,274,145 | B1 | 8/2001 | Chen et al. |
| 6,338,947 | B1 | 1/2002 | Sahin et al. |
| 6,417,165 | B1 | 7/2002 | Valmori et al. |
| 6,525,177 | B2 | 2/2003 | Stockert |
| 6,605,711 | B1 | 8/2003 | Valmori et al. |
| 6,689,742 | B1 | 2/2004 | Cerundolo et al. |
| 6,723,832 | B1 | 4/2004 | Knuth et al. |
| 6,756,044 | B1 | 6/2004 | Roelvink et al. |
| 6,800,730 | B1 | 10/2004 | Tureci et al. |

FOREIGN PATENT DOCUMENTS

| WO | 91/18926 | 12/1991 |
| WO | WO98/32855 | 7/1998 |
| WO | WO01/74855 | 10/2001 |
| WO | WO2005/032475 | 4/2005 |
| WO | WO2005/071088 | 10/2005 |
| WO | WO/2007/044406 | 4/2007 |

OTHER PUBLICATIONS

Rimoldi et al., Efficient simultaneous presentation of NY-ESO-1/LAGE-1 primary and nonprimary open reading frame-derived CTL epitopes in melanoma, Journal of Immunology, Journal of Immunology, 165:12, pp. 7253-7261, (Dec. 15, 2000).
Odunsi Kunle et al., NY-ESO-1 and LAGE-1 cancer testis antigens are potential targets for immunotherapy in epithelial ovarian cancer, Cancer Research, 63:18 , pp. 6076-6083, (Sep. 15, 2003).
Chen, et al., (1997) Proceedings of the National Academy of Sciences USA, vol. 94: pp. 1914-1918.
Nicholaou, et al., (2006) Immunology Cell Biology, vol. 84: pp. 303-317.
Jungbluth, et al., (2001) Int. J. Cancer, vol. 92: pp. 856-860.
Jager, et al., (1998), J. Exp. Medical, vol. 187: pp. 265-270.
Yamaguchi, et al., (2004), Clinical Cancer Res., Vo. 10: pp. 890-961.
Davis, et al., (2004) Proceedings of the National Academy of Sciences USA., vol. 101: pp. 10697-10702.
Jager, et al., (2000) Proceedings of the National Academy of Sciences USA, vol. 97: pp. 12198-12203.
Sun et al., (2006) Cancer Immunology Immunotherapy, vol. 55: pp. 644-652.

*Primary Examiner* — S. Devi
(74) *Attorney, Agent, or Firm* — Eric J. Kron

(57) ABSTRACT

Fusion proteins comprising an antigen derived from NY-ESO-1 linked to an antigen derived from LAGE-1, which may further comprise carriers, fusion partners, or the like, are provided. Methods for preparing, formulating, and using such fusion proteins are also provided. Such proteins are useful a vaccine components for inducing an immune response against a range of cancer-antigen-bearing cells.

5 Claims, 23 Drawing Sheets

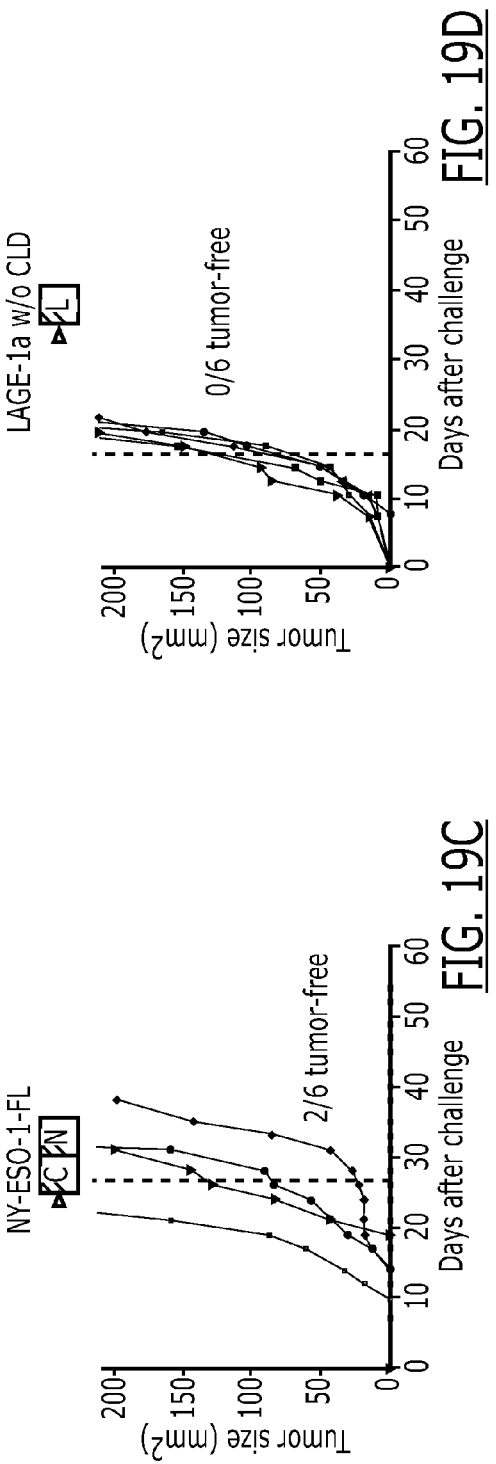
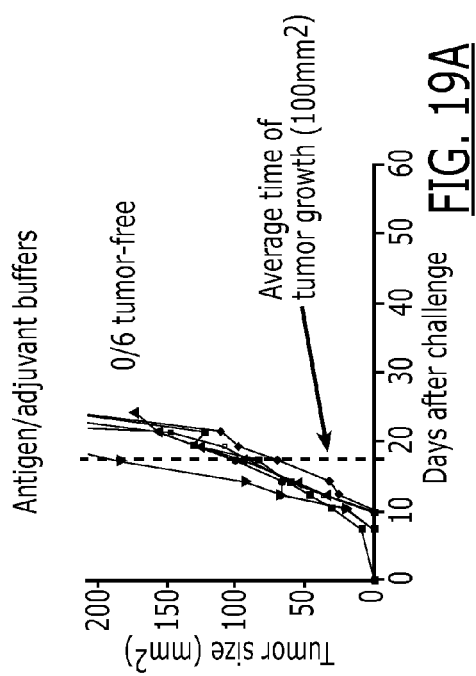
FIG. 19A, FIG. 19B, FIG. 19C, FIG. 19D
Controls

Screening #1: NYES01-specific Immune Responses

| Immunogens | | IgG2a (ng/ml) | % CD4 (INF-v+/TNF-α+) | WB anti-NYES01 w/o CLD |
|---|---|---|---|---|
| LVL030 | P C L N | 509,499 | 0.23 | + |
| LVL068 | C L N | 231,255 | 0.27 | +++ |
| LVL078 | C N L | 159,471 | 0.30 | +++ |
| LVL024 | P C N L | 155,384 | 0.23 | + |
| LVL076 | N L | 109,041 | 0.30 | + |
| LVL020 | P N L | 18,410 | 0.13 | + |
| LVL079 | L N | 16,309 | 0.20 | + |
| LVL026 | P L N | 10,520 | 0.07 | + |
| LVL075 | L | 36 | − | − |
| NYESOFL | C N | 531,385 | 0.87 | +++ |

FIG. 21A

Screening #1: LAGE 1a w/o CLD -specific immune responses

| Immunogens | | IgG2a (ng/ml) | % CD4 (INF-v+/TNF-α+) |
|---|---|---|---|
| LVL068 | C L N | 315,092 | 0.20 |
| LVL078 | C N L | 206,300 | 0.13 |
| NYESO FL | C N | 64,959 | 0.37 |
| LVL076 | N L | 28,803 | 0.03 |
| LVL079 | L N | 16,445 | 0.17 |
| LVL024 | P C N L | 10,832 | 0.10 |
| LVL030 | P C L N | 11,625 | 0.13 |
| LVL026 | P L N | 4,671 | − |
| LVL020 | P N L | 4,067 | 0.03 |
| LVL075 | L | 10,447 | 0.07 |

FIG. 21B

FUSION PROTEIN

CROSS REFERENCE TO RELATED APPLICATIONS

This application is a continuation-in-part application of co-pending international application PCT/US2008/050879, filed 11 Jan. 2008, which claims the benefit of Great Britain patent application serial number GB0709707.4, filed 21 May 2007, U.S. provisional application Ser. No. 60/914,925, filed 30 Apr. 2007, U.S. provisional application Ser. No. 60/914,848, filed 30 Apr. 2007, and Great Britain patent application serial number GB 0700759.4, filed 15 Jan. 2007, each of which are incorporated herein by reference in their entirety.

FIELD OF THE INVENTION

The present invention relates generally to polypeptides and constructs comprising an antigen derived from one or both of the tumor rejection antigens NY-ESO-1 and LAGE-1.

BACKGROUND TO THE INVENTION

Cancer testis (CT) antigens are a class of tumour-associated antigens with expression normally restricted to germ cells in the testis, ovaries or trophoblast cells. These antigens are not usually expressed in adult somatic tissues. See, Simpson, et al., Nat. Rev. Cancer, 5 (8):615-625 (2005); Scanlan, et al., Immunol. Reviews, 188:22-32 (2002); Scanlan, et al., Canc. Immun., 4:1-15 (2004).

The gene regulation of CT antigens is disrupted in cancer patients, leading to the aberrant expression of these antigens in a wide variety of tumours. The first CT antigen to be identified, MAGE-1, was identified in the early 1990s by T-cell epitope cloning (van der Bruggen et al, 1991 Science 13; 254 (5038):1643-7; van der Bruggen et al, 1999 Science 254:1643-1647; Traversari, et al, 1992 Immunogenetics, 35 (3):145-152; and U.S. Pat. No. 5,342,774, incorporated by reference). Since then, serological expression cloning technique (SEREX) (Sahin, et al., Proc. Natl. Acad. Sci. USA, 92 (25):11810-11813 (1995) and U.S. Pat. No. 5,698,396), recombinant antigen expression on yeast surface (RAYS) (Mischo, et al., Canc. Immun., 3:5-16 (2003)) and differential mRNA expression analysis (Gure, et al., Int. J. Canc., 85 (5):726-732 (2000)) have led to the identification of approximately 90 CT antigens, and their number is expected to grow in the coming years. The immunogenicity of some CT antigens in cancer patients makes them an ideal target for the development of tumour vaccines.

NY-ESO-1. A cancer testis antigen currently of interest for use in cancer immunotherapy is NY-ESO-1. This antigen was first identified by SEREX in an oesophageal squamous cell carcinoma in the late 90's at the New York Branch of the Ludwig Institute for Cancer Research (Chen, et al., PNAS USA, 94 (5):1914-1918 (1997); and U.S. Pat. No. 5,804,381, incorporated by reference).

The protein NY-ESO-1 is 180 amino acids in length and can be described as being composed of three regions:

| | |
|---|---|
| An N-terminal region | about or approximately amino acids 1 to 70, |
| A central region | about or approximately amino acids 71 to 134, and |
| A C-terminal region | about or approximately amino acids 135 to 180. |

A collagen-like region comprises about or approximately or about amino acids 15 to 73 of the N-terminal region (see FIG. 1).

The protein NY-ESO-1 has been found in a wide variety of tumours, including but not limited to ovarian cancer, lung cancer, breast cancer, prostrate, oesophageal cancer, bladder cancer and in melanomas. (Nicholaou T, et al, Immunol Cell Biol. 2006 June; 84 (3):303-17 and Jungbluth, et al. 2001, Int. J. Canc., 92 (6):856-860). Spontaneous humoral and cellular immune responses against this antigen have been described in patients with NY-ESO-1-positive tumours, and a number of HLA (Human Leukocyte Antigen) class I- and II-restricted peptides have been identified (Jager, et al., 1998 J. Exp. Med., 187 (2):265-270; Yamaguchi, et al., 2004 Clin. Canc. Res., 10 (3):890-961; and Davis, et al., 2004 Proc. Natl. Acad. Sci. USA, 101 (29):10697-10702). Exemplary of the patent literature are U.S. Pat. Nos. 6,140,050; 6,251,603; 6,242,052; 6,274,145; 6,338,947; 6,417,165; 6,525,177; 6,605,711; 6,689,742; 6,723,832; 6,756,044; and 6,800,730, all incorporated by reference.

In a clinical trial, three partially overlapping NY-ESO-1-derived peptides with binding motifs to HLA-A2 (157-167, 157-165 and 155-163) have been used in a vaccine to treat twelve patients with metastatic NY-ESO-1 expressing tumours. This study demonstrated that synthetic NY-ESO-1 peptides can be administered safely and are capable of generating potentially beneficial T cell responses (Jager, et al., 2000 PNAS USA, 97 (22):12198-12203).

A number of MHC (major histocompatibility complex) class I and II epitopes in the protein have been identified by different groups see, for example, FIG. 1. These epitopes are merely representative of epitopes reported for the protein and the list in FIG. 1 is not exhaustive. Furthermore, at least one or more of the epitopes reported and/or listed in FIG. 1 have not been confirmed by experimentation. The collagen-like region in the N-terminal contains at least one MHC class I epitope referred to herein as A31. The central region comprises several MHC class 2 epitopes referred to herein as DR1, DR2, DR4, DR7 and DP4. This region also contains several MHC class I epitopes referred to herein as B35, B51, Cw3 and Cw6. The C-terminal is believed to contain at least two class II epitopes (DR4 and DP4) and one class I epitope (A2).

LAGE-1. A further cancer testis antigen, LAGE-1, has also been identified. Two LAGE-1 transcripts have been described, LAGE-1a and LAGE1b. LAGE-1b is incompletely spliced and codes for a putative protein of approximately 210 amino acids residues, while the LAGE-1a gene product contains 180 amino acid residues (Sun et al. Cancer Immunol Immunother 2006: 55: 644-652).

The N-terminal regions of the LAGE-1 and NY-ESO-1 proteins are highly conserved and are thought to have more than 97% identity. However, LAGE-1 differs from NY-ESO-1 in the central regions which are only 62% identical. The C-terminals of NY-ESO-1 and LAGE-1a are highly conserved (more than 97% identity). However, the C-terminal of LAGE-1b is longer and not conserved and is thought to have less than 50% identity with the same region in LAGE-1a/NY-ESO-1.

General information relating to these proteins is available from the LICR web site (see www.cancerimmunity.org/CT-database).

SUMMARY OF THE INVENTION

The present invention provides an immunogenic fusion protein comprising:
(i) NY-ESO-1 or a fragment thereof, linked to
(ii) LAGE-1 or a fragment thereof,
in which at least one of NY-ESO-1 and/or LAGE-1 is truncated or partially truncated, or is a fragment including one or more epitopes of NY-ESO-1 or LAGE-1. The present invention also provides an immunogenic fusion protein comprising:
(i) LAGE-1 or a fragment thereof, linked to
(ii) NY-ESO-1 or a fragment thereof,
in which at least one of NY-ESO-1 and/or LAGE-1 is truncated or partially truncated, or is a fragment including one or more epitopes of NY-ESO-1 or LAGE-1. Thus, polypeptides and fusion proteins comprising truncated or partially truncated NY-ESO-1, or a fragment thereof, including one or more epitopes of NY-ESO-1 are also provided. Also provided are polypeptides and fusion proteins comprising truncated or partially truncated LAGE-1, or a fragment thereof, including one or more epitopes of LAGE-1. Compositions and methods involving such fusion proteins and polypeptides are also provided.

BRIEF DESCRIPTION OF THE FIGURES

Sheet 1/23.

Sheet 2/23.

Sheet 3/23.

Sheet 4/23.

Sheet 5/23.

Sheet 6/23.

Sheet 7/23.

Sheet 8/23.

Sheet 9/23.

Sheet 10/23.

Sheet 10/23.

Sheet 11/23.

Sheet 11/23.

Sheet 11/23.

Sheet 12/23.

Sheet 13/23.

Sheet 14/23.

Sheet 15/23.

Sheet 16/23, FIGS. 19 A-D summarizes B-16-NY-ESO-1 tumor growth in the control mice used in the 76-day trial.

Figure 20A:
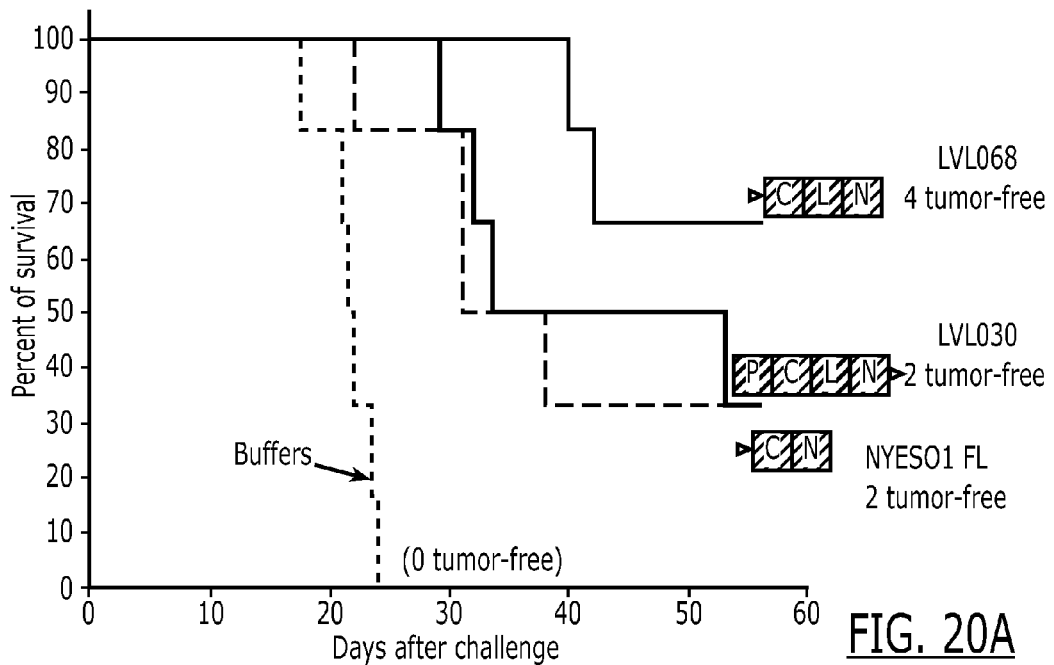
Figure 20B:
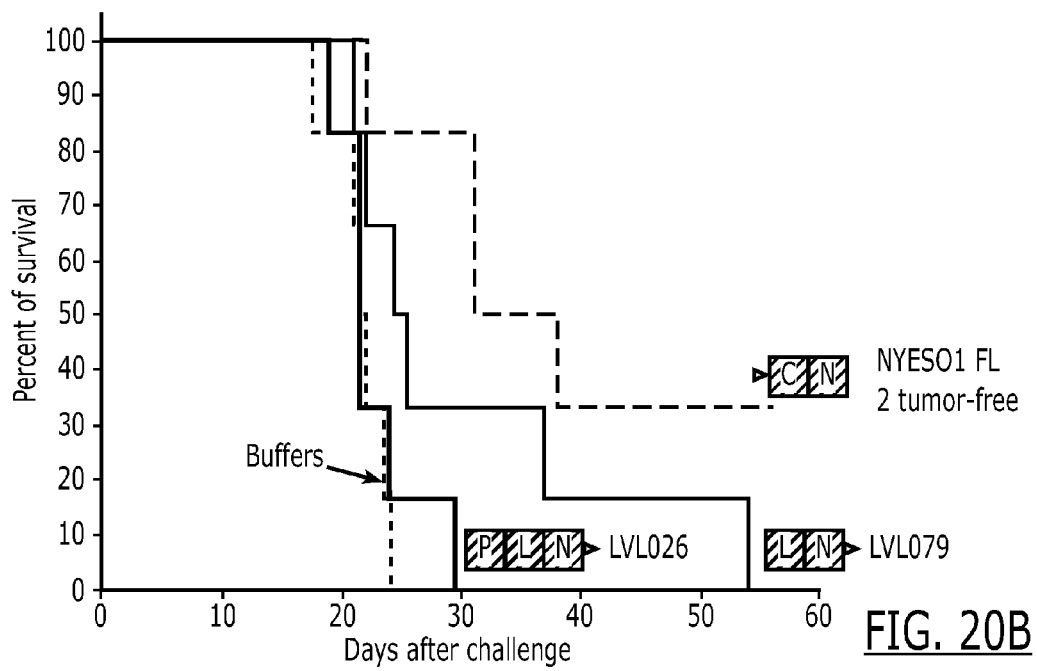

Sheet 17/23, FIGS. 20 A-B shows survival of mice immunized with full-length NY-ESO-1, LVL030, LVL068, LVL079, or LVL026.

Sheet 18/23, FIGS. 21 A-B summarizes the NY-ESO-1-specific immune responses as assessed by ELISA, FACS, and Western Blot and LAGE-1a(without the collagen like domain)-specific immune responses as assessed by ELISA and FACS.

Figure 22:
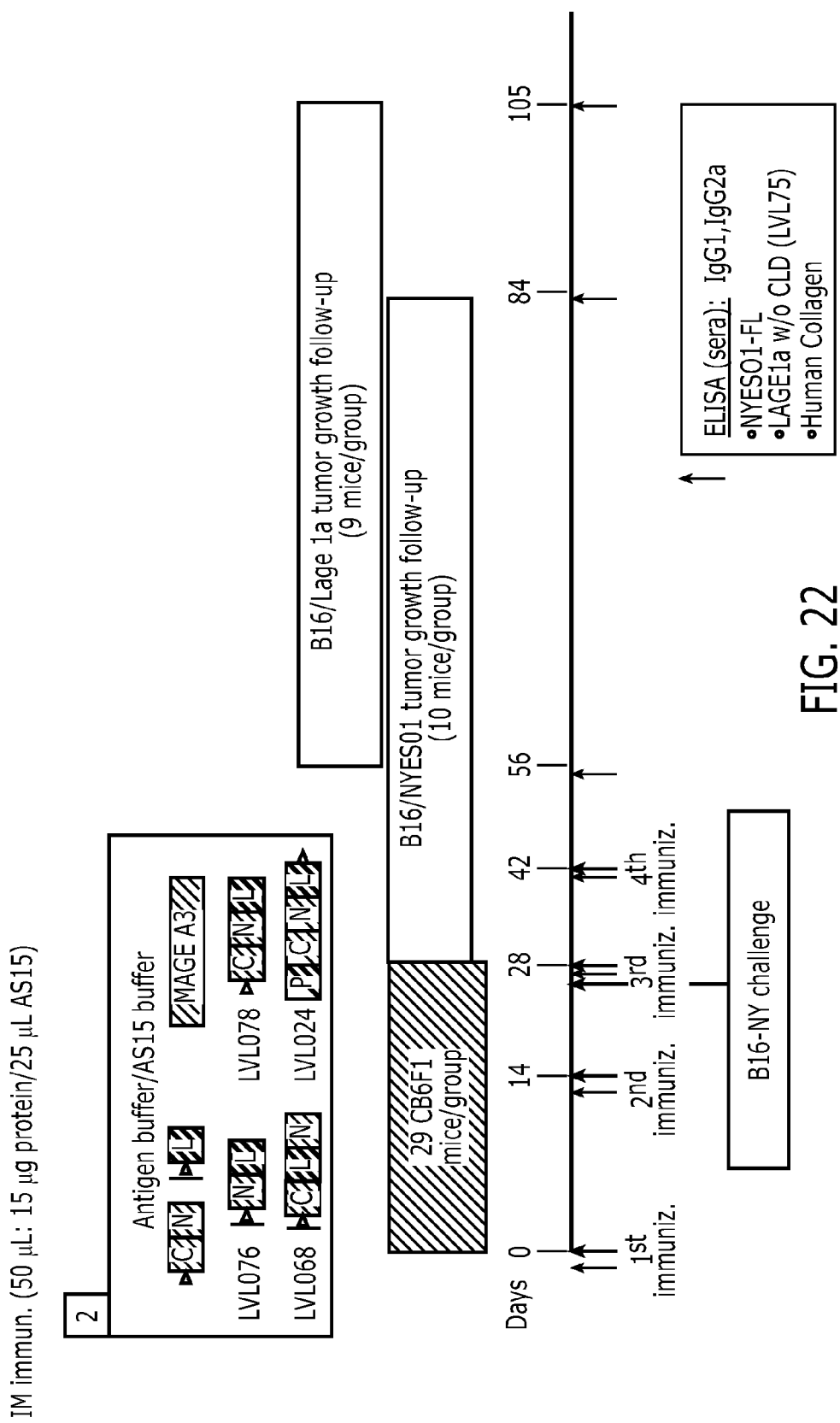

Sheet 19/23, FIG. 22 summarizes the experimental design of screening #2, a 105 day trial to determine whether intramuscular immunization with selected fusion proteins plus adjuvant confers protection against B16/NY-ESO-1 challenge and B16/LAGE-1a challenge. B16/NY-ESO-1 challenge is shown.

Figure 23:
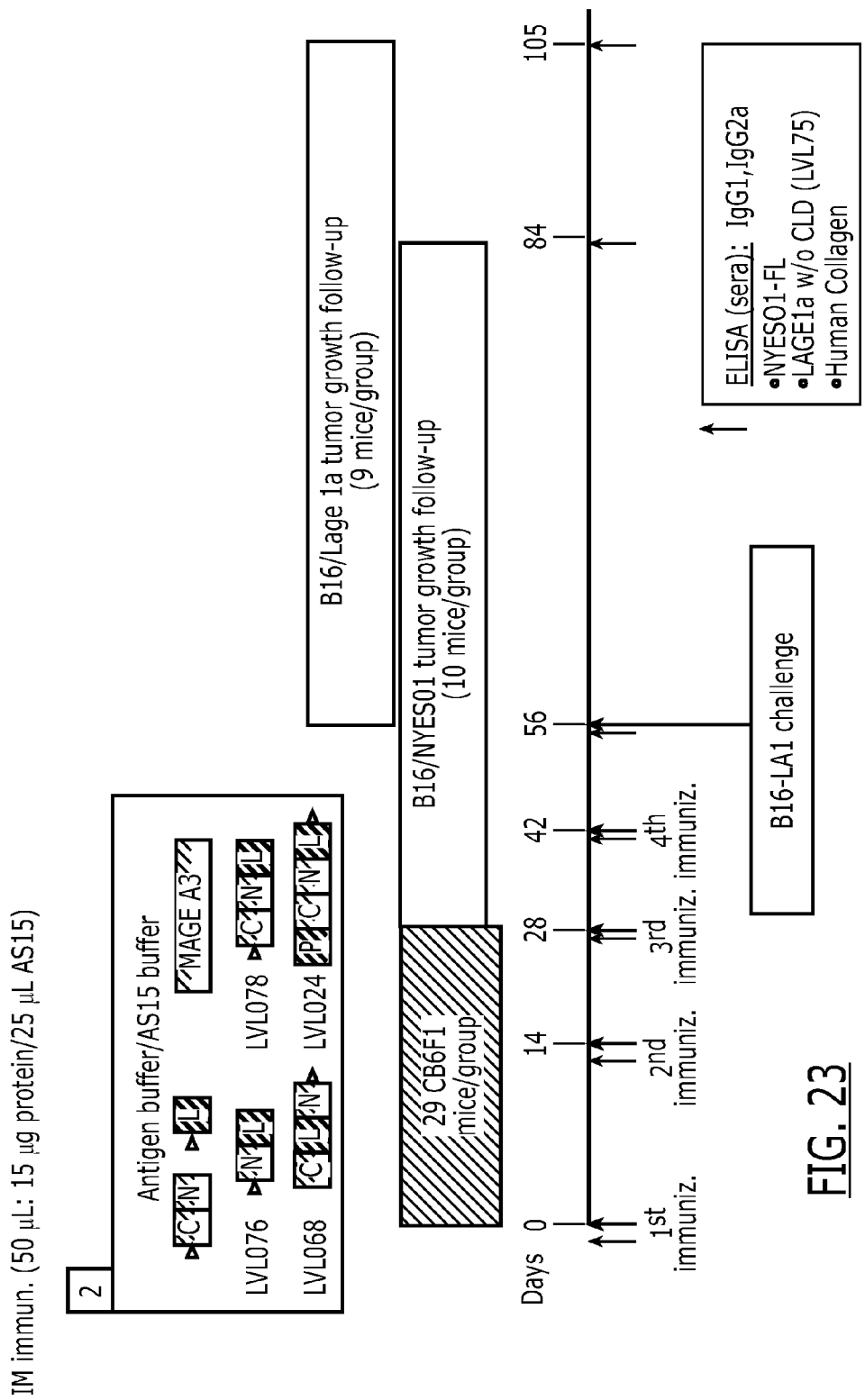

Sheet 20/23, FIG. 23 summarizes screening #2 and shows the B16/LAGE-1a challenge.

Figure 24A:
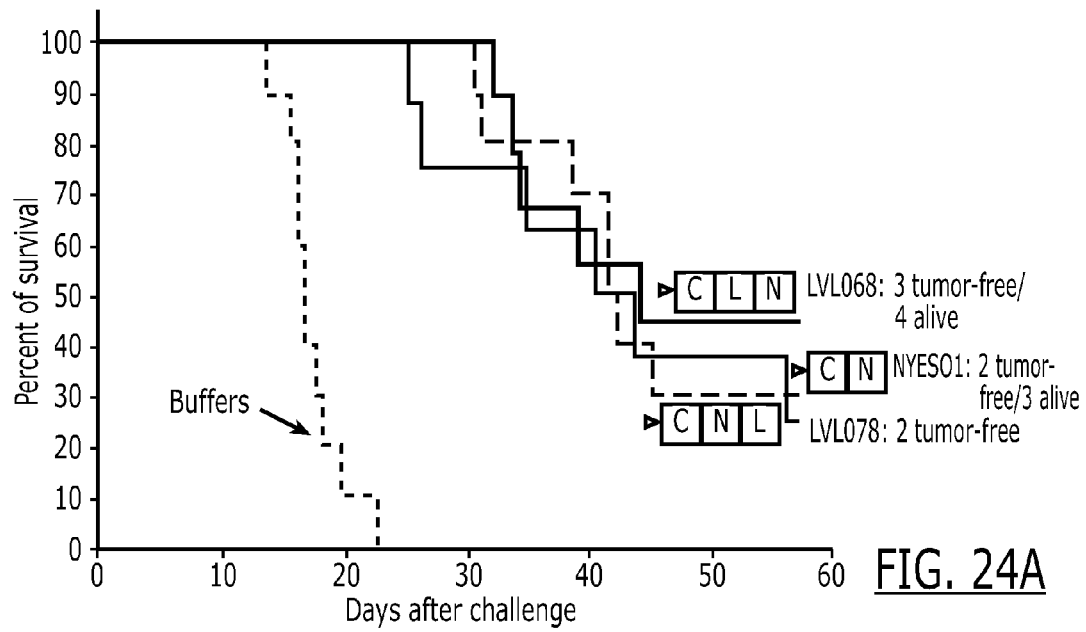
Figure 24B:
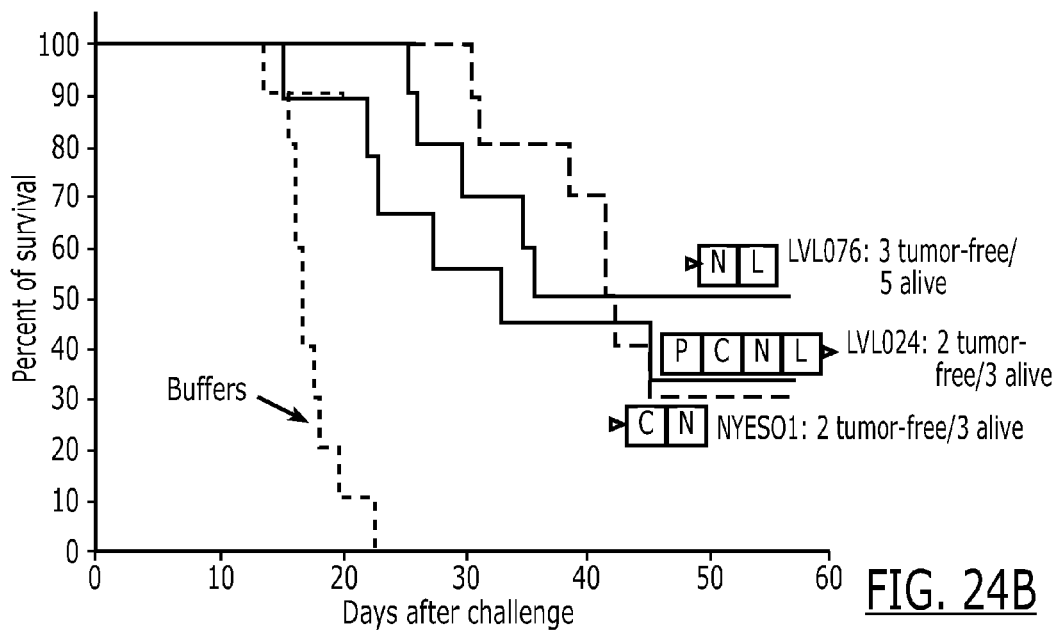

Sheet 21/23, FIGS. 24 A-B shows survival of mice immunized with LVL078, LVL068, full-length NY-ESO-1, LVL024, and LVL076 post-B16/NY-ESO-1 challenge. See FIG. 24.

Figure 25A:
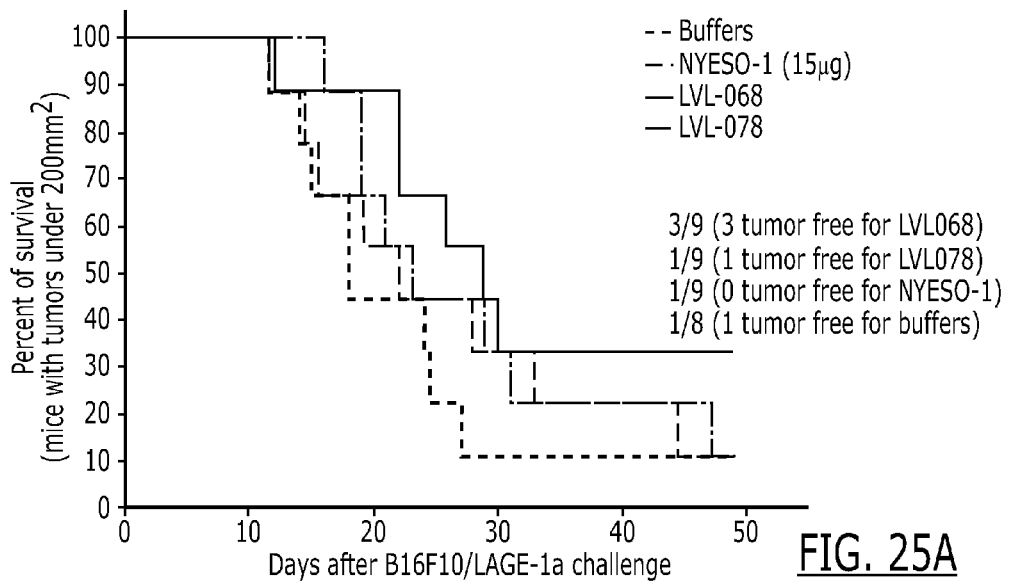
Figure 25B:
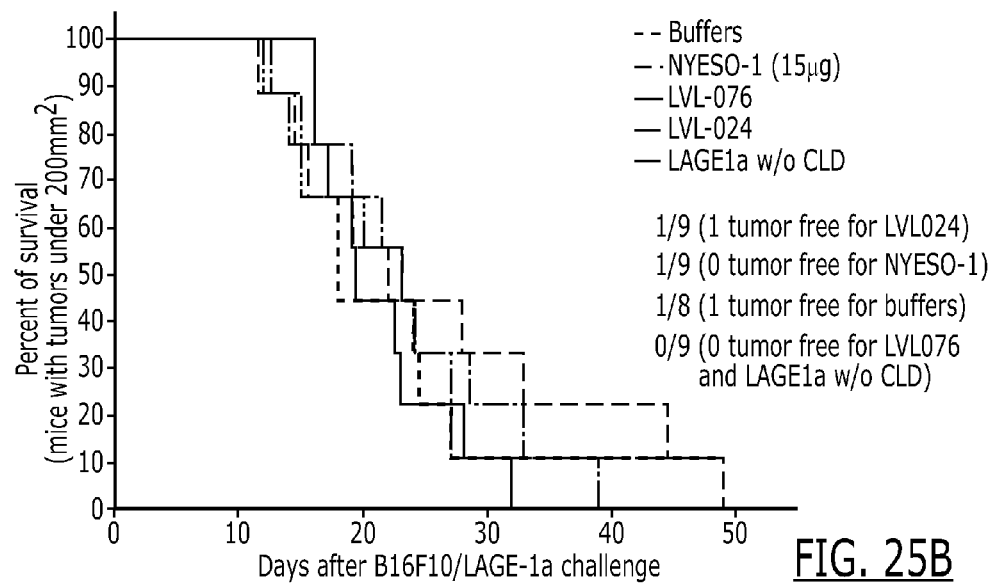

Sheet 22/23, FIGS. 25 A-B shows survival of mice immunized with LVL076, LAGE-1a without the collagen like region, LVL024, full-length NY-ESO-1, LVL078, or LVL068 post-B16/LAGE-1a challenge.

Figure 26:
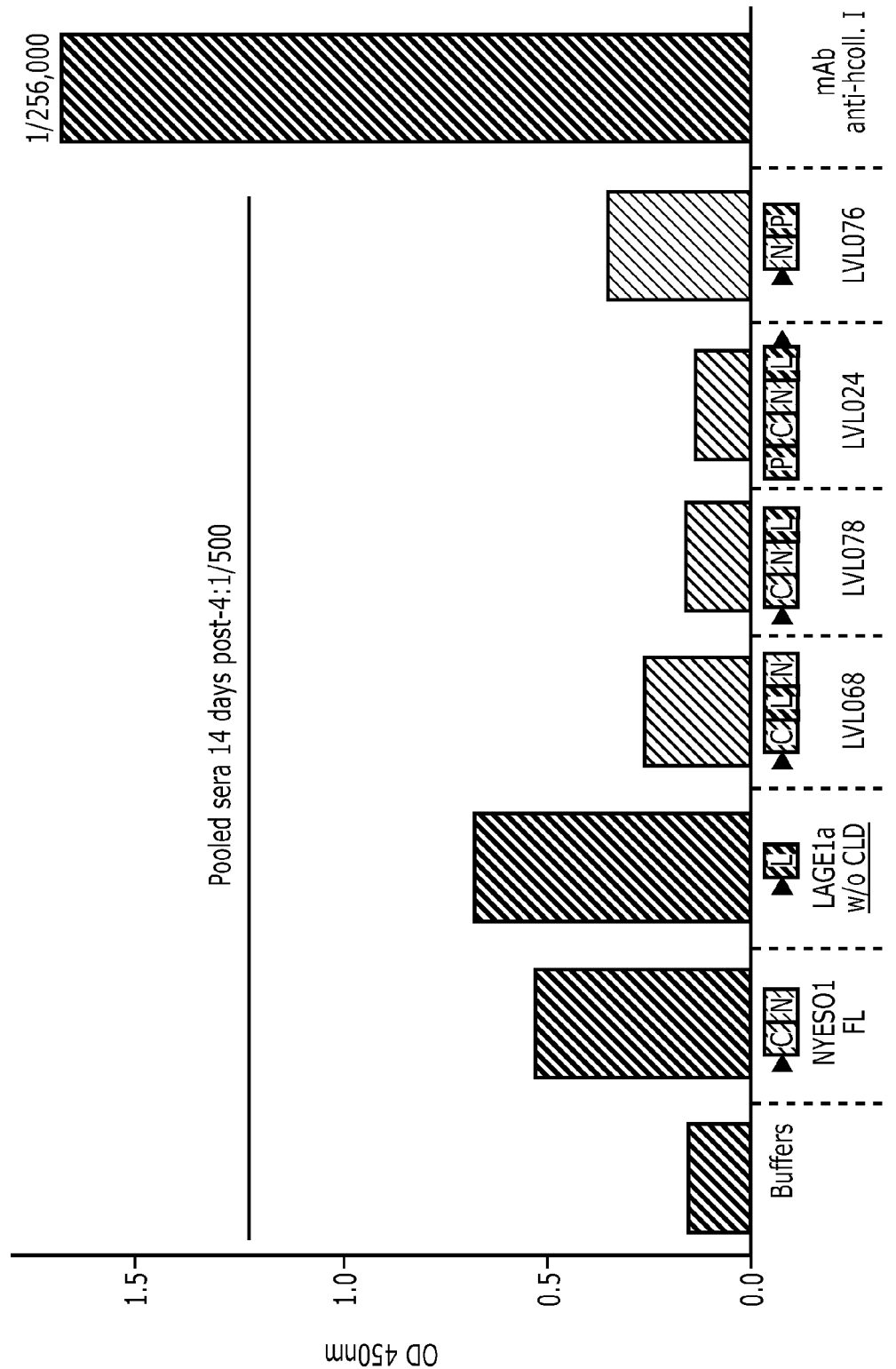

Sheet 23/23, FIG. 26. Columns 1-8, from left to right, show the results of ELISAs carried out to detect possible human collagen-specific immune responses in mice immunized with one of the following: (1) Buffers (control); (2) full-length NY-ESO-1; (3) LAGE-1a without the collagen like domain; (4) LVL068; (5) LVL078; (6) LVL024; (7) LVL076. Positive control (column 8) contains an anti-human collagen 1 monoclonal antibody (mAb anti-human collagen I).

DETAILED DESCRIPTION OF THE INVENTION

Fusion Proteins. The fusion proteins of the invention are useful for the treatment of cancers, and more specifically for the treatment of: melanoma; breast cancer; prostate cancer; bladder cancer including transitional cell carcinoma; lung cancer including non-small cell lung carcinoma (NSCLC); head and neck cancer including oesophageal carcinoma; squamous cell carcinoma; carcinoma of the gastrointestinal tract; liver cancer; brain tumours; leukemia; and various sarcomas.

Based on the expression profiles of LAGE-1 and NY-ESO-1 the fusion protein according to the invention has the potential to be effective in an estimated 37% of breast cancers. The treatment according to the present invention may also be particularly suitable for the treatment of patients not eligible for Her2/neu targeted therapy. The fusion protein of the invention is also predicted to be effective in approximately 35% of prostate cancer patients, 35% of bladder cancer patients, 40% of melanoma patients and 35% of patients with NSCLC (non-small cell lung carcinoma). In one embodiment, the fusion protein of the invention may enable a broader population of patients to be treated because patients having tumours that express both NY-ESO-1 and/or LAGE-1 (including LAGE-1a and LAGE-1b) may be given a fusion protein of the present invention.

The fusion protein according to the invention may also be more immunogenic than its individual component proteins, for the following reasons:
  removal of one or more of the collagen-like domains may reduce potential immunotolerance of the compound caused by its homology with natural endogenous collagen structure, or
  the optional addition of a heterologous fusion partner may further stimulate CD4 T-cell responses. Thus, the fusion proteins are useful for inducing an immunogenic response to a cancer antigen such as NY-ESO-1 or LAGE-1, or both.

The NY-ESO-1 employed in the invention may be full length, partially truncated or truncated NY-ESO-1 or any fragment thereof that includes one or more epitopes capable of raising an immune response to NY-ESO-1. Full length NY-ESO-1 protein in the context of this specification is intended to mean a protein of about or approximately 1 to 180 amino acids and at least 95, 96, 97, 98, 99% or 100% identical, to the naturally occurring protein (SEQ ID NO:49). As used herein, the term "LAGE-1" refers to one or more LAGE-1 family members such as LAGE-1a and LAGE 1b, as described in the lines below. "Full length LAGE-1a" protein is intended to mean a protein 95, 96, 97, 98, 99% or 100% identical to SEQ ID NO:58. Similarly, "full length LAGE-1b" protein is intended to mean a protein 95, 96, 97, 98, 99% or 100% identical to the naturally occurring protein (SEQ ID NO:71).

In one embodiment, the identity is over the full-length of the sequence. Thus, the invention also extends to said fusion proteins with conservative substitutions. Conservative substitutions are well known and are generally set up as the default scoring matrices in sequence alignment computer programs. These programs include PAM250 (Dayhoft M. O. et al., (1978), "A model of evolutionary changes in proteins", "Atlas of Protein sequence and structure" 5 (3) M. O. Dayhoft (ed.), 345-352), National Biomedical Research Foundation, Washington, and Blosum 62 (Steven Henikoft and Jorja G. Henikoft (1992), and "Amino acid substitution matrices from protein blocks"), Proc. Natl. Acad. Sci. USA 89 (Biochemistry): 10915-10919.

In general terms, substitution within the following groups are conservative substitutions, but substitutions between groups are considered non-conserved. The groups are:
  i) Aspartate/asparagine/glutamate/glutamine,
  ii) Serine/threonine,
  iii) Lysine/arginine, iv) Phenylalanine/tyrosine/tryptophane,
v) Leucine/isoleucine/valine/methionine,
vi) Glycine/alanine.

"Partially truncated" in the context of this specification is intended to mean NY-ESO-1 or LAGE-1 protein (as appropriate) in which the majority of the collagen-like has been region removed but still comprising or consisting of the epitope A31 found in this region.

In one embodiment, partially truncated NY-ESO-1 and/or LAGE-1 comprises or consists of a range of amino acids from amino acid 44, 45, 46, 47, 48, 49, 50, 51 or 52 to amino acid 175, 176, 177, 178, 179 or 180 or any combination of these amino acids, for example from amino acid 48 to amino acid 180 or from amino acid 46 to 178. In one embodiment partially truncated NY-ESO-1 or LAGE-1 comprises or consists of about or exactly amino acids 48 to 180 (or about or exactly amino acids 48-210 in the case of LAGE-1b). In one embodiment, the term "about" in this context may be taken to mean amino acids up to +/-10% of the total number of amino acids of the sequence are optionally added or deleted from the sequence. In one embodiment, partially truncated NY-ESO-1 comprises or consists of amino acids 48 to 180 of NY-ESO-1.

In one embodiment, partially truncated LAGE-1b comprises or consists of a range of amino acids from amino acid 44, 45, 46, 47, 48, 49, 50, 51 or 52 to amino acid 205, 206, 207, 208, 209 or 210 or any combination of these amino acids, for example from amino acid 48 to amino acid 210 or from amino acid 46 to 208. In one embodiment partially truncated LAGE-1b comprises or consists of about or exactly amino acids 48 to 210. In one embodiment, the term "about" in this context may be taken to mean amino acids up to +/-10% of the total number of amino acids of the sequence are optionally added or deleted from the sequence. In one embodiment, partially truncated LAGE-1b comprises or consists of amino acids 48 to 210 of LAGE-1b.

"Truncated" in the context of this specification is intended to mean NY-ESO-1 or LAGE-1 protein (as appropriate) in which the collagen-like region has been removed (including the removal of the A31 epitope). In one embodiment, truncated NY-ESO-1 and/or LAGE 1 comprises or consists of about or exactly amino acids 71-180 (or about or exactly amino acids 71-210 in the case of LAGE-1b).

In one embodiment, truncated NY-ESO-1 or LAGE-1 comprises or consists of a range of amino acids from amino acid 67, 68, 69, 70, 71, 72, 73, 74 or 75 to amino acid 175, 176, 177, 178, 179 or 180 or any combination of these amino acids, for example from amino acid 71 to amino acid 180 or from amino acid 69 to 178. In one embodiment truncated NY-ESO-1 or LAGE-1 comprises or consists of about or exactly amino acids 71 to 180 (or about or exactly amino acids 71-210 in the case of LAGE-1b).

In one embodiment, the term "about" in this context may be taken to mean amino acids up to +/-10% of the total number of amino acids of the sequence are optionally added or deleted from the sequence. In one embodiment, truncated NY-ESO-1 or LAGE-1 comprises or consists of amino acids 71 to 180 of NY-ESO-1 or LAGE-1.

In one embodiment, truncated LAGE-1b comprises or consists of a range of amino acids from amino acid 67, 68, 69, 70, 71, 72, 73, 74 or 75 to amino acid 205, 206, 207, 208, 209 or 210 or any combination of these amino acids, for example from amino acid 71 to amino acid 210 or from amino acid 69 to 208. In one embodiment truncated LAGE-1b comprises or consists of about or exactly amino acids 71 to 210. In one embodiment, the term "about" in this context may be taken to mean amino acids up to +/-10% of the total number of amino acids of the sequence are optionally added or deleted from the sequence. In one embodiment, truncated LAGE-1b comprises or consists of amino acids 71 to 210 of LAGE-1b.

By "other fragments" is intended those which, when incorporated into the fusion protein of the invention, result in a final protein with the desired properties and advantages of the fusion proteins of the invention.

NY-ESO-1. In accordance with the foregoing are provided modified antigens comprising an antigen derived from the tumor rejection antigen NY-ESO-1 wherein the collagen region is partially truncated or completely truncated. In some embodiments, more than the collagen region is removed. In some embodiments, the modified antigen is genetically modified. In some embodiments the modified antigen is recombinant. In some embodiments are provided polypeptides comprising an antigen as described in the preceding sentences. In some embodiments, exemplary polypeptides comprise a heterologous protein, such as protein D from Haemophilus influenzae type B or a fragment thereof. In some embodiments are provided constructs comprising a nucleotide sequence encoding the aforementioned polypeptides.

In some embodiments are provided an immunogenic polypeptide comprising NY-ESO-1 or a fragment thereof, wherein NY-ESO-1 does not include the collagen-like region. In others, NY-ESO-1 is partially truncated or truncated or comprises any fragment thereof that includes one or more epitopes. In some embodiments, such polypeptides have conservative substitutions. In some embodiments, such polypeptides and constructs are useful as a prophylactic for the prevention or substantial amelioration of cancer relapse.

Thus, in some embodiments one or more amino acids are removed from the collagen regions. More specifically, in some embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, or 73 amino acids are removed from the portion including the collagen region, i.e., roughly amino acids 1-73 of SEQ ID NO:49. The amino acids may be removed from adjacent positions in the collagen region or from positions that are not adjacent. In other words, in some embodiments, an amino acid is removed from any of positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, or 73 or any combination thereof, within that portion of SEQ ID NO:49. Those of skill in the art understand that in some embodiments, portions of the amino acid sequence are preserved such that particular epitopes therein are retained within a resulting polypeptide.

In some embodiments, a fragment of the NY-ESO-1 central region or C-terminal region is utilized. Thus, in some embodiments the polypeptide may comprise one or more fragments of the amino acid sequence set forth in SEQ ID NO:49, i.e., fragments which contain one or more of amino acid positions 74-75, 76-80, 81-85, 86-90, 91-95, 96-100, 101-105, 106-110, 111-115, 116-120, 121-125, 126-130, 131-135, 136-140, 141-145, 146-150, 151-155, 156-160, 161-165, 166-170, 171-175, 176-180, or any combination thereof. Those of skill in the art understand that in some embodiments, the amino acid sequence is preserved such that particular epitopes are retained within a resulting polypeptide.

LAGE-1. In some embodiments are provided a modified antigen comprising an antigen derived from the tumor rejection antigen LAGE-1 wherein the collagen region is partially truncated or completely truncated. In some embodiments, more than the collagen region is removed. In some embodiments, the modified antigen is genetically modified. In some embodiments, the modified antigen is recombinant. In some embodiments are provided polypeptides comprising an antigen as described in the preceding sentences. In some embodiments the antigen is derived from the tumor rejection antigen LAGE-1a. In some embodiments the antigen is derived from the tumor rejection antigen LAGE-1b. In other embodiments, exemplary fusion proteins comprise a heterologous protein, such as protein D from Haemophilus influenzae type B or a fragment thereof. In some embodiments are provided constructs comprising a nucleotide sequence encoding the aforementioned polypeptides.

In some embodiments are provided an immunogenic polypeptide comprising LAGE-1 or a fragment thereof, wherein LAGE-1 does not include the collagen-like region. In others, LAGE-1 is partially truncated or truncated or comprises any fragment thereof that includes one or more epitopes. In some embodiments, the polypeptide comprises a hybrid of the LAGE-1 polypeptide and the collagen like region of NY-ESO-1. In some embodiments, the polypeptide comprises part, or all, of the NY-ESO-1 collagen region joined to partially truncated or truncated LAGE-1. In some embodiments, such polypeptides have conservative substitutions. In some embodiments, such polypeptides and constructs are useful as a prophylactic for the prevention or substantial amelioration of cancer relapse.

Thus, in some embodiments one or more amino acids are removed from the collagen region, or even from the N-terminal amino acids. More specifically, in some embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, or 73 amino acids are removed from the collagen region or even the N-terminal amino acids, i.e., roughly amino acids 1-73 of SEQ ID NO:58 (LAGE-1a) or SEQ ID NO:71 (LAGE-1b). The amino acids may be removed from adjacent positions in this region or from positions that are not adjacent. In other words, in some embodiments, one or more amino acids are removed from any of positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, or 73 or any combination thereof, within SEQ ID NO:58 (LAGE-1a) or SEQ ID NO:71 (LAGE-1b). Those of skill in the art understand that in some embodiments, portions of the amino acid sequence are preserved such that particular epitopes therein are retained within a resulting polypeptide.

In some embodiments, a fragment of the LAGE-1 central region or C-terminal region is utilized. Thus, in some embodiments the polypeptide may comprise one or more fragments of the amino acid sequence set forth in SEQ ID NO:58 (LAGE-1a) or SEQ ID NO:71 (LAGE-1b), i.e., fragments which contain one or more of amino acid positions 74, 75, 76, 77, 78, 79, 80, 81-85, 86-90, 91-95, 96-100, 101-105, 106-110, 111-115, 116-120, 121-125, 126-130, 131-135, 136-140, 141-145, 146-150, 151-155, 156-160, 161-165, 166-170, 171-175, 176-180, or any combination thereof. Those of skill in the art understand that in some embodiments, the amino acid sequence is preserved such that particular epitopes are retained within a resulting polypeptide.

In one aspect the invention provides a fusion protein comprising full length NY-ESO-1.

In one aspect the invention provides a fusion protein comprising partially truncated NY-ESO-1.

In one aspect the invention provides a fusion protein comprising truncated NY-ESO-1.

In one aspect the invention provides a fusion protein comprising full length LAGE-1.

In one aspect the invention provides a fusion protein comprising partially truncated LAGE-1.

In one aspect the invention provides a fusion protein comprising truncated LAGE-1.

In one aspect the LAGE-1 employed in the invention is LAGE-1a.

In one aspect the LAGE-1 employed in the invention is LAGE-1b.

In one aspect of the invention the N-terminal of NY-ESO-1 is fused to the C-terminal of the LAGE-1.

In one aspect of the invention the C-terminal of NY-ESO-1 is fused to the N-terminal of the LAGE-1.

The immunogenicity of the fusion proteins of the invention may be further increased and/or the production properties of the protein further improved by incorporation of a fragment from a further heterologous antigen, for example protein D, a surface protein of the gram-negative bacterium, Haemophilus influenza B. Further information on immunological fusion partners derived from protein D can be obtained from WO 91/18926.

The proteins for inclusion in a fusion partner of the present invention may be chemically conjugated, or may be expressed as recombinant fusion proteins. In one embodiment, the fusion protein is expressed as a recombinant fusion protein.

The further heterologous fusion partner may assist in providing T helper epitopes (immunological fusion partner), or may assist in expressing the protein at higher yields (expression enhancer). In one embodiment, the further heterologous fusion partner may be both an immunological fusion partner and an expression enhancing partner.

In one embodiment, the protein D or derivative thereof comprises about or exactly the first ⅓ of the protein, for example about or exactly amino acids 1 to 109 of protein D. In this embodiment, amino acids 2-Lys and/or 3-Thr of the native protein D sequence may be substituted with the amino acids 2-Asp and/or 3-Pro. In a further embodiment, the protein D or derivative thereof comprises or consists of about or exactly amino acids 20 to 127 of protein D. In one embodiment, the protein D for use in the present invention does not include the secretion sequence of the protein. Generally, in fusion proteins of the present invention, the protein D derivative is not lipidated.

In one embodiment, the protein D further comprises the amino acids Met, Asp and Pro, for example fused to the N-terminus of the protein D fragment (ie the construct may comprise or consist of "MDP—20-127 protein D"). It is thought these three additional amino acids may aid the stability of the protein and/or increase the level of the protein expression thereof.

In one aspect the invention provides a fusion protein in which the N-terminal fragment (i.e the first third) of protein D (as described above) is fused to the N-terminus of a fusion protein of the invention or an immunogenic fragment thereof. More specifically, a fusion of protein D and the N-terminus of the fusion protein of the invention may be effected such that the latter replaces the C-terminal-fragment of protein D that has been excised. Thus the N-terminus of protein D becomes the N-terminus of the fusion protein.

Other heterologous fusion partners or fragments thereof may be included in the fusion protein of the invention, instead of or in addition to protein D, for example:

the non-structural protein from influenzae virus, NS1 (haemagglutinin). Typically, the N-terminal 81 amino acids may be used, although different fragments may be used provided they include T-helper epitopes;

LytA derived from Streptococcus pneumoniae, which synthesize an N-acetyl-L-alanine amidase LytA coded by the LytA gene (Gene, 43 (1986) page 265-272) such as the repeat portion of the LytA molecule found in the C terminal end, for example starting at residue 178 such as residues 188-305. In one embodiment, the heterologous fusion partner is CLytA. In a further embodiment, the heterologous fusion partner is CPC, a fusion protein comprising CLytA-P2-CLytA, as described in WO03/104272. Purification of hybrid proteins containing the C-LytA fragment at its amino terminus has been described in Biotechnology: 10, (1992) page 795-798.

Fusion proteins of the invention may further include an affinity tag, for example, a histidine tail (also known as a his-tag) comprising between 1 to 10, for example 6 or 10 histidine residues. These residues may, for example, be on the terminal portion, such as the N-terminal and/or the C-terminal portion of the protein. The affinity tag may be incorporated to further improve the purification of the protein.

Certain specific fusion proteins of the invention may, for example, be constructed as described in the Figures Each of the embodiments set forth in the Figures represent independent aspects of the invention. Further examples of constructs of fusion proteins according to the present invention are given in Tables 1-4 and in the Sequence Listing.

Nucleic Acids. The present invention also extends to the nucleic acids and polynucleic acids, such as DNA, encoding for fusion proteins of the invention. The processes of the invention may be performed by conventional recombinant techniques such as described in Maniatis et al., Molecular Cloning-A Laboratory Manual; Cold Spring Harbor, 1982-1989. In particular, a process may comprise the steps of:

i) preparing a replicable or integrating expression vector capable, in a host cell, of expressing a DNA polymer comprising a nucleotide sequence that encodes the fusion protein or an immunogenic derivative thereof;

ii) transforming a host cell with said vector;

iii) culturing said transformed host cell under conditions permitting expression of said DNA polymer to produce said protein; and iv) recovering said protein.

The term 'transforming' is used herein to mean the introduction of foreign DNA into a host cell. This can be achieved, for example by transformation, transfection or infection with an appropriate plasmid or viral vector using e.g. conventional techniques as described in Genetic Engineering; Eds. S. M. Kingsman and A. J. Kingsman; Blackwell Scientific Publications; Oxford, England, 1988. The term 'transformed' or 'transformant' will hereafter apply to the resulting host cell containing and expressing the foreign gene of interest. Expression vectors comprising nucleotide sequences encoding fusion proteins of the present invention are novel and also form part of the invention.

The replicable expression vectors may be prepared in accordance with the invention, by cleaving a vector compatible with the host cell to provide a linear DNA segment having an intact replicon, and combining said linear segment with one or more DNA molecules, which, together with said linear segment encode the desired product, such as the DNA polymer encoding the protein of the invention, or derivative thereof, under ligating conditions. Thus, the DNA polymer may be preformed or formed during the construction of the vector, as desired.

The choice of vector will be determined in part by the host cell, which may be prokaryotic or eukaryotic but are generally E. coli or CHO cells. Suitable vectors include plasmids for example TMCP14 or pET21 or pET26, pcDNA3, bacteriophages, cosmids and recombinant viruses. In one embodiment in which expression is in baculovirus, yeast or CHO host cells, one of the following vectors could be used: pEE14, pPICZA, pPICZB, pPICZC, pDMT-DEST48 and pAcSG2. The preparation of the replicable expression vector may be carried out conventionally with appropriate enzymes for restriction, polymerisation and ligation of the DNA, by procedures described in, for example, Maniatis et al. cited above.

The recombinant host cell is prepared, in accordance with the invention, by transforming a host cell with a replicable expression vector of the invention under transforming conditions. Suitable transforming conditions are conventional and are described in, for example, Maniatis et al. cited above, or "DNA Cloning" Vol. II, D. M. Glover ed., IRL Press Ltd, 1985. The choice of transforming conditions is determined by the host cell. Thus, a bacterial host such as E. coli may be treated with a solution of $CaCl_2$ (Cohen et al., Proc. Nat. Acad. Sci., 1973, 69, 2110) or with a solution comprising a mixture of RbCl, $MnCl_2$, potassium acetate and glycerol, and then with 3-[N-morpholino]-propane-sulphonic acid, RbCl and glycerol. Mammalian cells in culture may be transformed by calcium co-precipitation of the vector DNA onto the cells. The invention also extends to a host cell transformed with a replicable expression vector of the invention.

The DNA may be codon optimized by standard techniques to further facilitate expression of the relevant host.

Culturing the transformed host cell under conditions permitting expression of the DNA polymer is carried out conventionally, as described in, for example, Maniatis et al. and "DNA Cloning" cited above. Thus, preferably the cell is supplied with nutrient and cultured at a temperature below 50° C. The proteins of the present invention may be expressed in prokaryotes or eukaryotes such as yeast but are often expressed in E. coli. Particular strains of E. coli such as:

AR58: a cryptic λ lysogen derived from N99 that is gal E::Tn 10, Δ-8(chlD-pgl), Δ-H1(cro-chlA), N$^+$, and cI857 (ref: Proc. Natl. Acad. Sci. USA vol 82, pp. 88-92, January 1985 Biochemistry)

BLR (DE3) Novagen, WI, USA (catalogue number: 69053-4): BLR is a recA$^-$ derivative of BL21, may be employed. Generally a selection marker of, for example kanamycine resistance or ampicillin resistance is incorporated to facilitate identification of the successful incorporation of the recombinant gene/construct into the expression system.

The product is recovered by conventional methods according to the host cell and according to the localisation of the expression product (intracellular or secreted into the culture medium or into the cell periplasm). Thus, where the host cell is bacterial, such as E. coli it may, for example, be lysed physically, chemically or enzymatically and the protein product isolated from the resulting lysate. Where the host cell is mammalian, the product may generally be isolated from the nutrient medium or from cell free extracts. Conventional protein isolation techniques include selective precipitation, adsorption chromatography, and affinity chromatography including a monoclonal antibody affinity column.

The proteins of the present invention are provided either soluble in a liquid form or in a lyophilised form. The present invention also provides pharmaceutical composition such as a vaccine comprising a fusion protein of the present invention and a pharmaceutically acceptable excipient.

When administered, the therapeutic compositions of the present invention can be administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The amounts will depend, of course, on the particular condition being treated, the severity of the condition, the individual patient parameters including age, physical condition, size and weight, the duration of the treatment, the nature of concurrent therapy (if any), the specific route of administration and like factors, within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons. It is generally expected that each human dose will comprise 1 to 1000 µg of protein, and preferably 30-300 µg.

In one aspect the pharmaceutical compositions used to administer the fusion proteins of the invention will be a vaccine. The vaccine may optionally contain one or more other tumour-associated antigens, polypeptides and/or peptides. For example, members belonging to the MAGE, LAGE and GAGE families.

Combination of NY-ESO-1/LAGE-1 and MAGE. In one embodiment of the present invention there is provided a composition comprising (a) an antigen component comprising a NY-ESO-1 or LAGE-1 antigen or fusion protein as described herein and (b) an antigen component comprising a MAGE antigen or fusion protein. In one embodiment, the composition may further comprise an adjuvant as described herein.

The MAGE antigen for use in the combination may comprise the full length MAGE antigen. Alternatively, the MAGE antigen may comprise an immunogenic portion of MAGE in which 1, 2, 3, 4, 5, 6, 7, 8, 9, 10 or more amino acids may be deleted from or substituted in the amino acid sequence. In one embodiment of the present invention, 2 amino acids may be deleted from the N-terminus of the MAGE sequence. In one embodiment of the present invention in which the antigen is MAGE-A3 or an immunogenic portion thereof, the sequence of MAGE-A3 may be from amino acid 3 to 314 of MAGE-A3.

In one embodiment of the present invention there is provided a composition comprising an NY-ESO-1/LAGE-1 antigen and/or fusion protein as described herein and a fusion protein comprising a MAGE-A3 antigen. In an alternative embodiment, the fusion protein comprising the MAGE-A3 antigen comprises or consists of the MAGE-A3 antigen and a fusion partner protein comprising about or approximately or about the first 109 amino acids of protein D, in which one or two or more amino acids from protein D are optionally substituted, and in which the signal sequence of protein D is optionally present, in addition to the first 109 amino acids of protein D.

The fusion proteins of the present invention may additionally optionally comprise one or more amino acids as "linkers" between the sequences of the antigen and the fusion partners or fusion partner proteins or between the antigen and a His tail, if present. The amino acids may be unrelated to the sequences of the antigen and/or fusion partner.

Fusion proteins of the present invention, as described herein, may additionally comprise amino acids Met-Asp-Pro at the N-terminal end of the fusion protein sequence. The Met amino acid may be from the original protein D sequence or may be from an unrelated sequence.

In one embodiment, the sequence of a fusion protein comprising MAGE-A3 and protein D for use in combinations of the present invention is shown in SEQ ID NO:98. SEQ ID NO:98, from the N-terminus, comprises the following features:

| | |
|---|---|
| Amino acids 1-18 | signal sequence of Protein D including 1-Met and the substitutions 2-Asp and 3-Pro for the native aa 2-Lys and 3-Thr of protein D |
| Amino acids 19-127 | inclusive of amino acids 20 to 127 of Protein D |
| Amino acids 128-129 | unrelated amino acids Met-Asp at aa 128-129 to create a cloning site |
| Amino acids 130-441 | fragment of MAGE3 (amino acids 3-314 of MAGE3) |
| Amino acids 442-443 | unrelated amino acids Gly-Gly |
| Amino acids 444-451 | 7 his tail |

The present invention also extends to methods of preparing said vaccines/compositions and to fusion proteins and vaccines/compositions obtained by or obtainable by the methods described.

Vaccine preparation is generally described in Vaccine Design ("The subunit and adjuvant approach" (eds. Powell M. F. & Newman M. J). (1995) Plenum Press New York). Encapsulation within liposomes is described by Fullerton, U.S. Pat. No. 4,235,877.

The fusion proteins of the present invention may be adjuvanted in a vaccine formulation of the invention. Suitable adjuvants include an aluminium salt such as aluminium hydroxide gel (alum) or aluminium phosphate, but may also be a salt of calcium, iron or zinc, or may be an insoluble suspension of acylated tyrosine, or acylated sugars, cationically or anionically derivatised polysaccharides, or polyphosphazenes. Other known adjuvants include CpG containing oligonucleotides. The oligonucleotides are characterised in that the CpG dinucleotide is unmethylated. Such oligonucleotides are well known and are described in, for example WO 96/02555.

In the formulation of the inventions it may be desirable that the adjuvant composition induces an immune response preferentially of the TH1 type. In one embodiment there is provided an adjuvant system including, for example, a combination of monophosphoryl lipid A, preferably 3-de-O-acylated monophosphoryl lipid A (3D-MPL) together with an aluminium salt. CpG oligonucleotides may also induce a TH1 response and may also be included.

In one embodiment there is provided a composition comprising a fusion protein as described herein and an adjuvant composition comprising the combination of a monophosphoryl lipid A and a saponin derivative, particularly the combination of QS21 and 3D-MPL as disclosed in WO 94/00153, or a less reactogenic composition where the QS21 is quenched with cholesterol as disclosed in WO 96/33739. One formulation that may be used comprises QS21, 3D-MPL & tocopherol in, for example, an oil in water emulsion is described in WO 95/17210. Another adjuvant formulation for use in the present invention may comprise QS21, 3D-MPL & CpG or equivalent thereof, for example, in an oil in water emulsion or as a liposomal formulation. Accordingly in one embodiment of the present invention there is provided a vaccine comprising a fusion protein of the invention and an adjuvant, for example as described above. The present invention also extends to methods of preparing vaccines and compositions comprising fusion proteins as described herein.

The present invention also contemplates delivery of nucleic acids, polypeptides or peptides as described herein for vaccination. Delivery of polypeptides and peptides can be accomplished according to standard vaccination protocols which are well known in the art. In another embodiment, the delivery of nucleic acid may be accomplished by ex vivo methods, i.e. by removing a cell from a subject, genetically engineering the cell to include a cancer associated antigen, and reintroducing the engineered cell into the subject. In general, this may involve introduction in vitro of a functional copy of a gene into a cell(s) of a subject, and returning the genetically engineered cell(s) to the subject. The functional copy of the gene is under operable control of regulatory elements, which permit expression of the gene in the genetically engineered cell(s). Numerous transfection and transduction techniques as well as appropriate expression vectors are well known to those of ordinary skill in the art, some of which are described in PCT application WO 95/00654. In vivo nucleic acid delivery using vectors such as viruses and targeted liposomes also is contemplated according to the invention.

Abbreviations

CO collagen-like region

W/Ocoll without collagen-like region (collagen-like domain)

PD1/3 protein D first third

Exemplary embodiments of fusion proteins and the nucleotide sequence encoding same are provided in Tables 1-3.

TABLE 1

Exemplary embodiments of fusion proteins and the nucleotide sequence encoding same are provided. Each nucleotide sequence is described by subject matter, identified by unique nucleotide sequence identifier (SEQ ID NO:), and set forth in the sequence listing. Each fusion protein is described by subject matter, identified by unique amino acid sequence identifier (SEQ ID NO:), and set forth in the sequence listing.

| SEQ ID NO: | TABLE 1 CONSTRUCT DESCRIPTION | SEQUENCE COMPONENTS |
|---|---|---|
| | Hybrid Collagen NY-ESO-1/LAGE1a without collagen | |
| 1 | Embodiment A - nucleotide sequence Hybrid Coll NY-ESO-1/LAGE1a WO coll (codon optimised) | |
| | Collagen like domain | 1-210bp |
| | NY-ESO-1 | 1-537bp |
| | Linker | 538-543bp |
| | LAGE1a | 544-846bp |
| | His-tag | 847-864bp |
| | Stop | 865-867bp |
| 2 | Embodiment B - nucleotide sequence ⅓ protein D/Hybrid Coll NY-ESO-1/LAGE1a WO coll (codon optimised) | |
| | MDP initiation sequence | 1-9bp |
| | ⅓ protein D | 10-333bp |
| | Collagen like domain | 334-540bp |
| | NY-ESO-1 | 334-867bp |
| | Linker | 868-873bp |
| | LAGE1a | 874-1176bp |
| | His-tag | 1177-1194bp |
| | Stop | 1195-1197bp |
| 3 | Embodiment A - amino acid sequence Hybrid Coll NY-ESO-1/LAGE1a WO coll with His-tag | |
| | Collagen like domain | 1-70aa |
| | NY-ESO-1 | 1-179aa |
| | Linker | 180-181aa |
| | LAGE1a | 182-282aa |
| | His-tag | 283-288aa |
| 4 | Embodiment B - amino acid sequence ⅓ protein D/Hybrid Coll NY-ESO-1/LAGE1a WO coll with His-tag | |
| | MDP initiation sequence | 1-3aa |
| | ⅓ protein D | 4-111aa |
| | Collagen like domain | 112-180aa |
| | NY-ESO-1 | 112-289aa |
| | Linker | 290-291aa |
| | LAGE1a | 292-392aa |
| | His-tag | 393-398aa |
| | Hybrid Collagen truncated NY-ESO-1/LAGE1a without collagen | |
| 5 | Embodiment C - Hybrid Coll trunc NY-ESO-1/LAGE1a WO coll (codon optimised) | |
| | Collagen like domain | 1-72bp |
| | NY-ESO-1 | 1-399bp |
| | Linker | 400-405bp |
| | LAGE1a | 406-708bp |
| | His-tag | 709-726bp |
| | Stop | 727-729bp |
| 6 | Embodiment D - nucleotide sequence-- ⅓ protein D/Hybrid Coll trunc NY-ESO-1/LAGE1a WO coll (codon optimised) | |
| | MDP initiation sequence | 1-9bp |
| | ⅓ protein D | 10-333bp |
| | Collagen like domain | 334-402bp |
| | NY-ESO-1 | 334-729bp |
| | Linker | 730-735bp |
| | LAGE1a | 736-1038bp |
| | His-tag | 1039-1056bp |
| | Stop | 1057-1059bp |
| 7 | Embodiment C - Hybrid Coll trunc NY-ESO-1/LAGE1a WO coll with His-tag | |
| | Collagen like domain | 1-24aa |
| | NY-ESO-1 | 1-133aa |
| | Linker | 134-135aa |
| | LAGE1a | 136-236aa |
| | His-tag | 237-242aa |
| 8 | Embodiment D - amino acid sequence ⅓ protein D/Hybrid Coll trunc NY-ESO-1/LAGE1a WO coll with His-tag | |
| | MDP initiation sequence | 1-3aa |
| | ⅓ protein D | 4-111aa |
| | Collagen like domain | 112-134aa |
| | NY-ESO-1 | 112-243aa |
| | Linker | 244-245aa |
| | LAGE1a | 246-346aa |
| | His-tag | 347-352aa |
| | Hybrid NY-ESO-1/LAGE1a without collagen like domain and contiguous cystein rich region (8aa) | |
| 9 | Embodiment E - nucleotide sequence Hybrid NY-ESO-1/LAGE1a WO coll (codon optimised) | |
| | NY-ESO-1 | 1-306bp |
| | Linker | 307-312bp |
| | LAGE1a | 313-615bp |
| | His-tag | 616-633bp |
| | Stop | 634-636bp |
| 10 | Embodiment F - nucleotide sequence ⅓ protein D/Hybrid NY-ESO-1/LAGE1a WO coll (codon optimised) | |
| | MDP initiation sequence | 1-9bp |
| | ⅓ protein D | 10-333bp |
| | NY-ESO-1 | 334-636bp |
| | Linker | 637-642bp |
| | LAGE1a | 643-945bp |
| | His-tag | 946-963bp |
| | Stop | 964-966bp |

TABLE 1-continued

Exemplary embodiments of fusion proteins and the nucleotide sequence encoding same are provided. Each nucleotide sequence is described by subject matter, identified by unique nucleotide sequence identifier (SEQ ID NO:), and set forth in the sequence listing. Each fusion protein is described by subject matter, identified by unique amino acid sequence identifier (SEQ ID NO:), and set forth in the sequence listing.

| SEQ ID NO: | TABLE 1 CONSTRUCT DESCRIPTION | SEQUENCE COMPONENTS |
|---|---|---|
| 11 | Embodiment E - amino acid sequence Hybrid NY-ESO-1/LAGE1a WO coll with His-tag | |
| | NY-ESO-1 | 1-102aa |
| | Linker | 103-104aa |
| | LAGE1a | 105-205aa |
| | His-tag | 206-211aa |
| 12 | Embodiment F - amino acid sequence ⅓ protein D/Hybrid NY-ESO-1/LAGE1a WO coll with His-tag | |
| | MDP initiation sequence | 1-3aa |
| | ⅓ protein D | 4-111aa |
| | NY-ESO-1 | 112-212aa |
| | Linker | 213-214aa |
| | LAGE1a | 215-315aa |
| | His-tag | 316-321aa |
| Hybrid Collagen LAGE1a/NY-ESO-1 without collagen | | |
| 13 | Embodiment G - nucleotide sequence Hybrid Coll LAGE1a/NY-ESO-1 WO coll (codon optimised) | |
| | Collagen like domain of NY-ESO-1 | 1-210bp |
| | LAGE1a | 211-540bp |
| | Linker | 541-546bp |
| | NY-ESO-1 | 547-849bp |
| | His-tag | 850-867bp |
| | Stop | 868-870bp |
| 14 | ⅓ protein D/Hybrid Coll LAGE1a/NY-ESO-1 WO coll (codon optimised) | |
| | MDP initiation sequence | 1-9bp |
| | ⅓ protein D | 10-333bp |
| | Collagen like domain of NY-ESO-1 | 334-540bp |
| | LAGE1a | 541-870bp |
| | Linker | 871-876bp |
| | NY-ESO-1 | 877-1179bp |
| | His-tag | 1180-1197bp |
| | Stop | 1198-1200bp |
| 15 | Embodiment G - amino acid sequence Hybrid Coll LAGE1a/NY-ESO-1 WO coll with His-tag | |
| | Collagen like domain of NY-ESO-1 | 1-70aa |
| | LAGE1a | 71-180aa |
| | Linker | 181-182aa |
| | NY-ESO-1 | 183-283aa |
| | His-tag | 284-289aa |
| 16 | ⅓ protein D/Hybrid Coll LAGE1a/NY-ESO-1 WO coll with His-tag (encoded by SEQ ID NO: 14) | |
| | MDP initiation sequence | 1-3aa |
| | ⅓ protein D | 4-111aa |
| | Collagen like domain of NY-ESO-1 | 112-180aa |
| | LAGE1a | 181-290aa |
| | Linker | 291-292aa |
| | NY-ESO-1 | 293-393aa |
| | His-tag | 394-399aa |
| Hybrid Collagen truncated LAGE1a/NY-ESO-1 without collagen | | |
| 17 | Hybrid Coll trunc LAGE1a/NY-ESO-1 WO coll (codon optimised) | |
| | Collagen like domain of NY-ESO-1 | 1-72bp |
| | LAGE1a | 73-402bp |
| | Linker | 403-408bp |
| | NY-ESO-1 | 409-711bp |
| | His-tag | 712-729bp |
| | Stop | 730-732bp |
| 18 | ⅓ protein D/Hybrid Coll trunc LAGE1a/NY-ESO-1 WO coll (codon optimised) | |
| | MDP initiation sequence | 1-9bp |
| | ⅓ protein D | 10-333bp |
| | Collagen like domain of NY-ESO-1 | 334-402bp |
| | LAGE1a | 403-732bp |
| | Linker | 733-738bp |
| | NY-ESO-1 | 739-1041bp |
| | His-tag | 1042-1059bp |
| | Stop | 1060-1062bp |
| 19 | Hybrid Coll trunc LAGE1a/NY-ESO-1 WO coll with His-tag (encoded by SEQ ID NO: 17) | |
| | Collagen like domain of NY-ESO-1 | 1-24aa |
| | LAGE1a | 25-134aa |
| | Linker | 135-136aa |
| | NY-ESO-1 | 137-237aa |
| | His-tag | 238-243aa |
| 20 | ⅓ protein D/Hybrid Coll trunc LAGE1a/NY-ESO-1 WO coll with His-tag (encoded by SEQ ID NO: 18) | |
| | MDP initiation sequence | 1-3aa |
| | ⅓ protein D | 4-111aa |
| | Collagen like domain of NY-ESO-1 | 112-134aa |
| | LAGE1a | 135-244aa |
| | Linker | 245-246aa |
| | NY-ESO-1 | 247-347aa |
| | His-tag | 348-353aa |
| Hybrid LAGE1a/NY-ESO-1 without collagen like domain and contiguous cystein rich region (8aa) | | |
| 21 | Embodiment E' - nucleotide sequence Hybrid LAGE1a/NY-ESO-1 WO coll (codon optimised) | |
| | LAGE1a | 1-309bp |
| | Linker | 310-315bp |
| | NY-ESO-1 | 316-618bp |
| | His-tag | 619-636bp |
| | Stop | 637-639bp |
| 22 | ⅓ protein D/Hybrid LAGE1a/NY-ESO1 WO coll (codon optimised) | |
| | MDP initiation sequence | 1-9bp |
| | ⅓ protein D | 10-333bp |
| | LAGE1a | 334-639bp |
| | Linker | 640-645bp |
| | NY-ESO-1 | 646-948bp |
| | His-tag | 949-966bp |
| | Stop | 967-969bp |
| 23 | Embodiment E' - amino acid sequence Hybrid LAGE1a/NY-ESO-1 WO coll with His-tag | |
| | LAGE1a | 1-103aa |
| | Linker | 104-105aa |
| | NY-ESO-1 | 106-206aa |
| | His-tag | 207-212aa |
| 24 | ⅓ protein D/Hybrid LAGE1a/NY-ESO-1 WO coll with His-tag (encoded by SEQ ID NO: 22) | |
| | MDP initiation sequence | 1-3aa |
| | ⅓ protein D | 4-111aa |
| | LAGE1a | 112-213aa |
| | Linker | 214-215aa |
| | NY-ESO-1 | 216-316aa |
| | His-tag | 317-322aa |
| His N-terminal Hybrid NY-ESO-1/Lage1a without collagen and contiguous cystein rich region (8aa) | | |
| 25 | His-Enterokinase site-NY-ESO-1/LAGE1a (codon optimised) | |
| | His-tag sequence | 1-36bp |
| | Enterokinase site | 37-72bp |
| | NY-ESO-1 | 73-375bp |
| | Linker | 376-381bp |
| | LAGE1a | 382-684bp |
| | Stop | 685-687bp |
| 26 | His-Enterokinase site-NY-ESO-1/LAGE1a (encoded by SEQ ID NO: 25) | |
| | His-tag (10 His) | 1-12aa |
| | Enterokinase site | 13-24aa |
| | NY-ESO-1 | 25-125aa |
| | Linker | 126-127aa |
| | LAGE1a | 128-228aa |

TABLE 1-continued

Exemplary embodiments of fusion proteins and the nucleotide sequence encoding same are provided. Each nucleotide sequence is described by subject matter, identified by unique nucleotide sequence identifier (SEQ ID NO:), and set forth in the sequence listing. Each fusion protein is described by subject matter, identified by unique amino acid sequence identifier (SEQ ID NO:), and set forth in the sequence listing.

| SEQ ID NO: | TABLE 1 CONSTRUCT DESCRIPTION | SEQUENCE COMPONENTS |
|---|---|---|
| 27 | His-NY-ESO-1/LAGE1a (codon optimised) | |
| | His-tag sequence | 1-21bp |
| | NY-ESO-1 | 22-324bp |
| | Linker | 325-330bp |
| | LAGE1a | 331-633bp |
| | Stop | 634-636bp |
| 28 | His-NY-ESO-1/LAGE1a (encoded by SEQ ID NO: 26) | |
| | His-tag (6 His) | 1-7aa |
| | NY-ESO-1 | 8-108aa |
| | Linker | 109-110aa |
| | LAGE1a | 111-211aa |
| | His-N-terminal Hybrid Collagen truncated NY-ESO-1/LAGE1a without collagen | |
| 29 | His-Enterokinase site-Coll trunc-NY-ESO-1/LAGE1a (codon optimised) | |
| | His-tag sequence | 1-36bp |
| | Enterokinase site | 37-72bp |
| | Collagen like domain | 73-141bp |
| | NY-ESO-1 | 73-468bp |
| | Linker | 469-474bp |
| | LAGE1a | 475-777bp |
| | Stop | 778-780bp |
| 30 | His-Enterokinase site-Coll trunc-NY-ESO-1/LAGE1a (encoded by SEQ ID NO: 29) | |
| | His-tag (10 His) | 1-12aa |
| | Enterokinase site | 13-24aa |
| | Collagen like domain | 25-47aa |
| | NY-ESO-1 | 25-156aa |
| | Linker | 157-158aa |
| | LAGE1a | 159-259aa |
| 31 | His-Coll trunc-NY-ESO-1/LAGE1a (codon optimised) | |
| | His-tag sequence | 1-21bp |
| | Collagen like domain | 22-90bp |
| | NY-ESO-1 | 22-417bp |
| | Linker | 418-423bp |
| | LAGE1a | 424-726bp |
| | Stop | 727-729bp |
| 32 | His-Coll trunc-NY-ESO-1/LAGE1a (encoded by SEQ ID NO: 31) | |
| | His-tag (6 His) | 1-7aa |
| | Collagen like domain | 8-30aa |
| | NY-ESO-1 | 31-139aa |
| | Linker | 140-141aa |
| | LAGE1a | 142-242aa |
| | His N-terminal Hybrid collagen NY-ESO-1/LAGE1a without collagen like domain | |
| 33 | His-Enterokinase site-Coll-NY-ESO-1/LAGE1a (codon optimised) | |
| | His-tag sequence | 1-36bp |
| | Enterokinase site | 37-72bp |
| | Collagen like domain | 73-279bp |
| | NY-ESO-1 | 73-606bp |
| | Linker | 607-612bp |
| | LAGE1a | 613-915bp |
| | Stop | 916-918bp |
| 34 | His-Enterokinase site-Coll-NY-ESO-1/LAGE1a (encoded by SEQ ID NO: 33) | |
| | His-tag (10 His) | 1-12aa |
| | Enterokinase site | 13-24aa |
| | Collagen like domain | 25-93aa |
| | NY-ESO-1 | 25-202aa |
| | Linker | 203-204aa |
| | LAGE1a | 205-305aa |
| 35 | His-Coll-NY-ESO-1/LAGE1a (codon optimised) | |
| | His-tag sequence | 1-21bp |
| | Collagen like domain | 22-228bp |
| | NY-ESO-1 | 22-555bp |
| | Linker | 556-561bp |
| | LAGE1a | 562-864bp |
| | Stop | 865-867bp |
| 36 | His-Coll-NY-ESO-1/LAGE1a (encoded by SEQ ID NO: 35) | |
| | His-tag (6 His) | 1-7aa |
| | Collagen like domain | 8-76aa |
| | NY-ESO-1 | 77-185aa |
| | Linker | 186-187aa |
| | LAGE1a | 188-288aa |
| | His-N-terminal Hybrid Lage1a/NY-ESO-1 without collagen and contiguous cystein rich region (8aa) | |
| 37 | His-Enterokinase site-LAGE1a/NY-ESO-1 (codon optimised) | |
| | His-tag sequence | 1-36bp |
| | Enterokinase site | 37-72bp |
| | LAGE1a | 73-378bp |
| | Linker | 379-384bp |
| | NY-ESO-1 | 385-687bp |
| | Stop | 688-690bp |
| 38 | His-Enterokinase site-LAGE1a/NY-ESO-1 (encoded by SEQ ID NO: 37) | |
| | His-tag (10 His) | 1-12aa |
| | Enterokinase site | 13-24aa |
| | LAGE1a | 25-126aa |
| | Linker | 127-128aa |
| | NY-ESO-1 | 129-229aa |
| 39 | His-LAGE1a/NY-ESO-1 (codon optimised) | |
| | His-tag sequence | 1-21bp |
| | LAGE1a | 22-327bp |
| | Linker | 328-333bp |
| | NY-ESO-1 | 334-636bp |
| | Stop | 637-639bp |
| 40 | His-LAGE1a/NY-ESO-1 (encoded by SEQ ID NO: 39) | |
| | His-tag (6 His) | 1-7aa |
| | LAGE1a | 8-109aa |
| | Linker | 110-111aa |
| | NY-ESO-1 | 112-212aa |
| | His-N-terminal Hybrid Collagen truncated LAGE1a/NY-ESO-1 without collagen | |
| 41 | His-Enterokinase site-Coll trunc-LAGE1a/NY-ESO-1 (codon optimised) | |
| | His-tag sequence | 1-36bp |
| | Enterokinase site | 37-72bp |
| | Collagen like domain of NY-ESO-1 | 73-141bp |
| | LAGE1a | 142-471bp |
| | Linker | 472-477bp |
| | NY-ESO-1 | 478-780bp |
| | Stop | 781-783bp |
| 42 | His-Enterokinase site-Coll trunc-LAGE1a/NY-ESO-1 (encoded by SEQ ID NO: 41) | |
| | His-tag (10 His) | 1-12aa |
| | Enterokinase site | 13-24aa |
| | Collagen like domain of NY-ESO-1 | 25-47aa |
| | LAGE1a | 48-157aa |
| | Linker | 158-159aa |
| | NY-ESO-1 | 160-260aa |
| 43 | His-Coll trunc-LAGE1a/NY-ESO-1 (codon optimised) | |
| | His-tag sequence | 1-21bp |
| | Collagen like domain of NY-ESO-1 | 22-90bp |
| | LAGE1a | 91-420bp |
| | Linker | 421-426bp |
| | NY-ESO-1 | 427-729bp |
| | Stop | 730-732bp |
| 44 | His-Coll trunc-LAGE1a/NY-ESO-1 (encoded by SEQ ID NO: 43) | |
| | His-tag (6 His) | 1-7aa |
| | Collagen like domain of NY-ESO-1 | 8-30aa |
| | LAGE1a | 31-140aa |

TABLE 1-continued

Exemplary embodiments of fusion proteins and the nucleotide sequence encoding same are provided. Each nucleotide sequence is described by subject matter, identified by unique nucleotide sequence identifier (SEQ ID NO:), and set forth in the sequence listing. Each fusion protein is described by subject matter, identified by unique amino acid sequence identifier (SEQ ID NO:), and set forth in the sequence listing.

| SEQ ID NO: | TABLE 1 CONSTRUCT DESCRIPTION | SEQUENCE COMPONENTS |
|---|---|---|
| | Linker | 141-142aa |
| | NY-ESO-1 | 143-243aa |
| | His N-terminal Hybrid collagen LAGE1a/NY-ESO-1 without collagen like domain | |
| 45 | His-Enterokinase site-Coll-LAGE1a/NY-ESO-1 (codon optimised) | |
| | His-tag sequence | 1-36bp |
| | Enterokinase site | 37-72bp |
| | Collagen like domain of NY-ESO-1 | 73-279bp |
| | LAGE1a | 280-609bp |
| | Linker | 610-615bp |
| | NY-ESO-1 | 616-918bp |
| | Stop | 919-921bp |
| 46 | His-Enterokinase site-Coll-LAGE1a/NY-ESO-1 (encoded by SEQ ID NO: 45) | |
| | His-tag (10 His) | 1-12aa |
| | Enterokinase site | 13-24aa |
| | Collagen like domain of NY-ESO-1 | 25-93aa |
| | LAGE1a | 94-203aa |
| | Linker | 204-205aa |
| | NY-ESO-1 | 206-306aa |
| 47 | His-Coll-LAGE1a/NY-ESO-1 (codon optimised) | |
| | His-tag sequence | 1-21bp |
| | Collagen like domain of NY-ESO-1 | 22-228bp |
| | LAGE1a | 229-558bp |
| | Linker | 559-564bp |
| | NY-ESO-1 | 565-867bp |
| | Stop | 868-870bp |
| 48 | His-Coll-LAGE1a/NY-ESO-1 (encoded by SEQ ID NO: 47) | |
| | His-tag (6 His) | 1-7aa |
| | Collagen like domain of NY-ESO-1 | 8-76aa |
| | LAGE1a | 77-186aa |
| | Linker | 187-188aa |
| | NY-ESO-1 | 189-289aa |

TABLE 2

Additional exemplary embodiments of fusion proteins and the nucleotide sequences encoding same are provided. Each nucleotide sequence is described by subject matter, identified by unique nucleotide sequence identifier (SEQ ID NO:), and set forth in the sequence listing. Each fusion protein is described by subject matter, identified by unique amino acid sequence identifier (SEQ ID NO:), and set forth in the sequence listing.

| SEQ ID NO: | TABLE 2. CONSTRUCT DESCRIPTION | SEQUENCE COMPONENTS |
|---|---|---|
| | Partially truncated collagen NY-ESO-1 | |
| 50 | Coll trunc NY-ESO-1 (codon optimised) | |
| | Collagen like domain | 1-72bp |
| | NY-ESO-1 | 1-399bp |
| | His-tag | 400-417bp |
| | Stop | 418-420bp |
| 51 | Coll trunc NY-ESO-1 with His-tag (encoded by SEQ ID NO: 50) | |
| | Collagen like domain | 1-24aa |
| | NY-ESO-1 | 1-133aa |
| | His-tag | 134-139aa |
| 52 | ⅓ protein D/Coll trunc NY-ESO-1 (codon optimised) | |
| | MDP initiation sequence | 1-9bp |
| | ⅓ protein D | 10-333bp |
| | Collagen like domain | 334-402bp |
| | NY-ESO-1 | 334-729bp |
| | His-tag | 730-747bp |
| | Stop | 748-750bp |
| 53 | ⅓ protein D/Coll trunc NY-ESO-1 with His-tag (encoded by SEQ ID NO: 52) | |
| | MDP initiation sequence | 1-3aa |
| | ⅓ protein D | 4-111aa |
| | Collagen like domain | 112-134aa |
| | NY-ESO-1 | 112-243aa |
| | His-tag | 244-249aa |
| | NY-ESO-1 WO coll | |
| 54 | NY-ESO-1 WO coll (codon optimised) | |
| | NY-ESO-1 | 1-306bp |
| | His-tag | 307-324bp |
| | Stop | 325-327bp |
| 55 | NY-ESO-1 WO coll with His-tag (encoded by SEQ ID NO: 54) | |
| | NY-ESO-1 | 1-102aa |
| | His-tag | 103-108aa |
| 56 | ⅓ protein D/NY-ESO-1 WO coll (codon optimised) | |
| | MDP initiation sequence | 1-9bp |
| | ⅓ protein D | 10-333bp |
| | NY-ESO-1 | 334-636bp |
| | His-tag | 637-654bp |
| | Stop | 655-657bp |
| 57 | ⅓ protein D/NY-ESO-1 WO coll with His-tag (encoded by SEQ ID NO: 56) | |
| | MDP initiation sequence | 1-3aa |
| | ⅓ protein D | 4-111aa |
| | NY-ESO-1 | 112-212aa |
| | His-tag | 213-218aa |

TABLE 3

Additional exemplary embodiments of fusion proteins and the nucleotide sequence encoding same are provided. Each nucleotide sequence is described by subject matter, identified by unique nucleotide sequence identifier (SEQ ID NO:), and set forth in the sequence listing. Each fusion protein is described by subject matter, identified by unique amino acid sequence identifier (SEQ ID NO:), and set forth in the sequence listing.

| SEQ ID NO: | TABLE 3 DESCRIPTION | SEQUENCE COMPONENTS |
|---|---|---|
| | Hybrid Collagen LAGE-1a without LAGE-1a collagen-like domain | |
| 59 | Hybrid Coll LAGE-1a WO coll (codon optimised) | |
| | Collagen like domain of NY-ESO-1 | 1-210bp |
| | LAGE-1a | 211-540bp |
| | His-tag | 541-558bp |
| | Stop | 559-561bp |
| 60 | Hybrid Coll LAGE-1a WO coll with His-tag (encoded by SEQ ID NO: 59) | |
| | Collagen like domain of NY-ESO-1 | 1-70aa |
| | LAGE-1a | 71-180aa |
| | His-tag | 181-186aa |

TABLE 3-continued

Additional exemplary embodiments of fusion proteins and the nucleotide sequence encoding same are provided. Each nucleotide sequence is described by subject matter, identified by unique nucleotide sequence identifier (SEQ ID NO:), and set forth in the sequence listing. Each fusion protein is described by subject matter, identified by unique amino acid sequence identifier (SEQ ID NO:), and set forth in the sequence listing.

| SEQ ID NO: | TABLE 3 DESCRIPTION | SEQUENCE COMPONENTS |
|---|---|---|
| 61 | ⅓ protein D/Hybrid Coll LAGE-1a WO coll with His-tag (codon optimised) | |
| | MDP initiation sequence | 1-9bp |
| | ⅓ protein D | 10-333bp |
| | Collagen like domain of NY-ESO-1 | 334-540bp |
| | LAGE-1a | 541-870bp |
| | His-tag | 871-888bp |
| | Stop | 889-891bp |
| 62 | ⅓ protein D/Hybrid Coll LAGE-1a WO coll with His-tag (encoded by SEQ ID NO: 61) | |
| | MDP initiation sequence | 1-3aa |
| | ⅓ protein D | 4-111aa |
| | Collagen like domain of NY-ESO-1 | 112-180aa |
| | LAGE-1a | 181-290aa |
| | His-tag | 291-296aa |
| Hybrid Collagen truncated LAGE-1a without collagen-like domain | | |
| 63 | Hybrid Collagen truncated LAGE-1a without collagen-like domain | |
| | Collagen like domain of NY-ESO-1 | 1-72bp |
| | LAGE-1a | 73-402bp |
| | His-tag | 403-420bp |
| | Stop | 421-423bp |
| 64 | Hybrid Coll trunc LAGE-1a WO coll with His-tag (encoded by SEQ ID NO: 63) | |
| | Collagen like domain of NY-ESO-1 | 1-24aa |
| | LAGE-1a | 25-134aa |
| | His-tag | 135-140aa |
| 65 | ⅓ protein D/Hybrid Coll trunc LAGE-1a WO coll with His-tag (codon optimised) | |
| | MDP initiation sequence | 1-9bp |
| | ⅓ protein D | 10-333bp |
| | Collagen like domain of NY-ESO-1 | 334-402bp |
| | LAGE-1a | 403-732bp |
| | His-tag | 733-750bp |
| | Stop | 751-753bp |
| 66 | ⅓ protein D/Hybrid Coll trunc LAGE-1a WO coll with His-tag (encoded by SEQ ID NO: 65) | |
| | MDP initiation sequence | 1-3aa |
| | ⅓ protein D | 4-111aa |
| | Collagen like domain of NY-ESO-1 | 112-134aa |
| | LAGE-1a | 135-244aa |
| | His-tag | 245-250aa |
| LAGE-1a without collagen like domain and contiguous cystein rich region (8aa) | | |
| 67 | LAGE-1a WO coll (codon optimised) | |
| | LAGE-1a | 1-309bp |
| | His-tag | 310-327bp |
| | Stop | 328-330bp |
| 68 | LAGE-1a WO coll with His-tag (encoded by SEQ ID NO: 67) | |
| | LAGE-1a | 1-103aa |
| | His-tag | 104-109aa |
| 69 | ⅓ protein D/LAGE-1a WO coll (codon optimised) | |
| | MDP initiation sequence | 1-9bp |
| | ⅓ protein D | 10-333bp |
| | LAGE-1a | 334-639bp |
| | His-tag | 640-657bp |
| | Stop | 6578-660bp |
| 70 | ⅓ protein D/LAGE-1a WO coll with His-tag (encoded by SEQ ID NO: 69) | |
| | MDP initiation sequence | 1-3aa |
| | ⅓ protein D | 4-111aa |
| | LAGE-1a | 112-213aa |
| | His-tag | 214-219aa |

TABLE 4

The fusion proteins discussed in the Examples and the nucleotide sequences encoding same are provided. Each nucleotide sequence is described by subject matter, identified by unique nucleotide sequence identifier (SEQ ID NO:), and set forth in the sequence listing. Each fusion protein is described by subject matter, identified by unique amino acid sequence identifier (SEQ ID NO:), and set forth in the sequence listing.

| CONSTRUCT NAME | NUCLEOTIDE SEQUENCE | AMINO ACID SEQUENCE |
|---|---|---|
| LVL020 | SEQ ID NO: 72 | SEQ ID NO: 73 |
| LVL024 | SEQ ID NO: 74 | SEQ ID NO: 75 |
| LVL026 | SEQ ID NO: 76 | SEQ ID NO: 77 |
| LVL030 | SEQ ID NO: 78 | SEQ ID NO: 79 |
| LVL068 | SEQ ID NO: 80 | SEQ ID NO: 81 |
| LVL076 | SEQ ID NO: 82 | SEQ ID NO: 83 |
| LVL078 | SEQ ID NO: 84 | SEQ ID NO: 85 |
| LVL079 | SEQ ID NO: 86 | SEQ ID NO: 87 |
| LVL106 | SEQ ID NO: 88 | SEQ ID NO: 89 |
| LVL151 | SEQ ID NO: 90 | SEQ ID NO: 91 |
| LVL155 | SEQ ID NO: 92 | SEQ ID NO: 93 |
| LVL156 | SEQ ID NO: 94 | SEQ ID NO: 95 |
| LVL157 | SEQ ID NO: 96 | SEQ ID NO: 97 |

As will be evident from the sequence listing, many of the constructs of Table 4 have similar designs to one or more embodiment set forth in the preceding tables. For example, LVL068 shares the same design as the embodiment set forth as SEQ ID NO:45, Table 1. LVL076 shares the same design as the embodiment set forth as SEQ ID NO:25, Table 1. LVL078 shares the same design as the embodiment set forth as SEQ ID NO:33, Table 1. LVL079 shares the same design as the embodiment set forth as SEQ ID NO:37, Table 1.

In addition, several of the fusion protein constructs set forth in Table 4, namely LVL155, LVL106, LVL156, LVL157, LVL151, were generated by routine modifications of other fusion protein sequences set forth in Table 4, namely LVL068, LVL030, LVL076, LVL078, LVL024, respectively. Such modifications include the removal of the amino acid residues between protein D and the beginning of the chimers (i.e., the portion derived from either of NY-ESO-1 and LAGE-1) and the removal of the amino acids between the his-tag and the beginning of the chimer. Thus, certain of the fusion proteins of Table 4 correspond closely to other fusion proteins in Table 4. The correspondence between these fusion proteins is set forth in Table 5 and described in greater detail in Example 4.

TABLE 5

Correspondence between LVL068, LVL030, LVL076, LVL078, LVL024 and the modified LVL155, LVL106, LVL156, LVL157, LVL151.

TABLE 5

| FUSION PROTEIN CONSTRUCT | CORRESPONDS TO | FUSION PROTEIN CONSTRUCT |
|---|---|---|
| LVL068 | | LVL155 |
| LVL030 | | LVL106 |
| LVL076 | | LVL156 |
| LVL078 | | LVL157 |
| LVL024 | | LVL151 |

EXAMPLES

Example 1

NY-LA1 Chimeric Protein Design and Production

Figure 1:
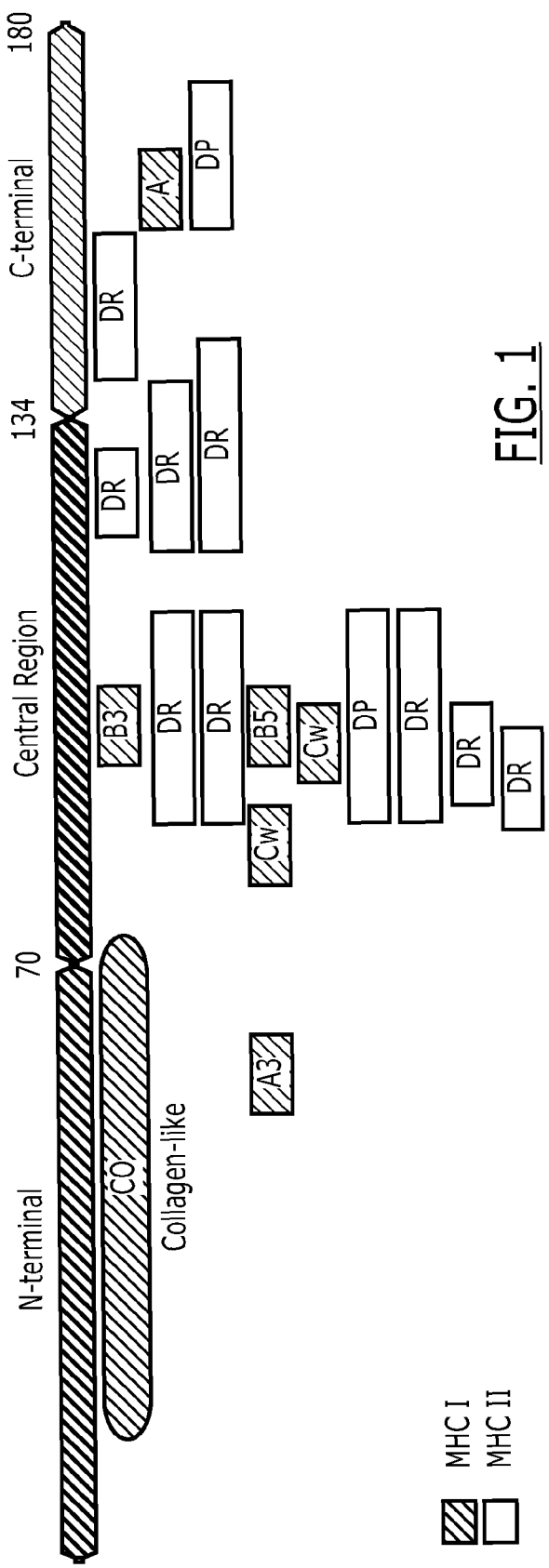
FIG. 1 shows a number MHC (major histocompatibility complex) class I and II epitopes on the NY-ESO-1 protein that have been identified by different groups. These epitopes are merely representative of epitopes reported for the protein thus the list in FIG. 1 is not exhaustive. Furthermore, at least one or more of the epitopes reported and/or listed in FIG. 1 have not been confirmed by experimentation. The reported amino acid sequence for NY-ESO-1 is found herein in SEQ ID NO:49.
Figure 2:
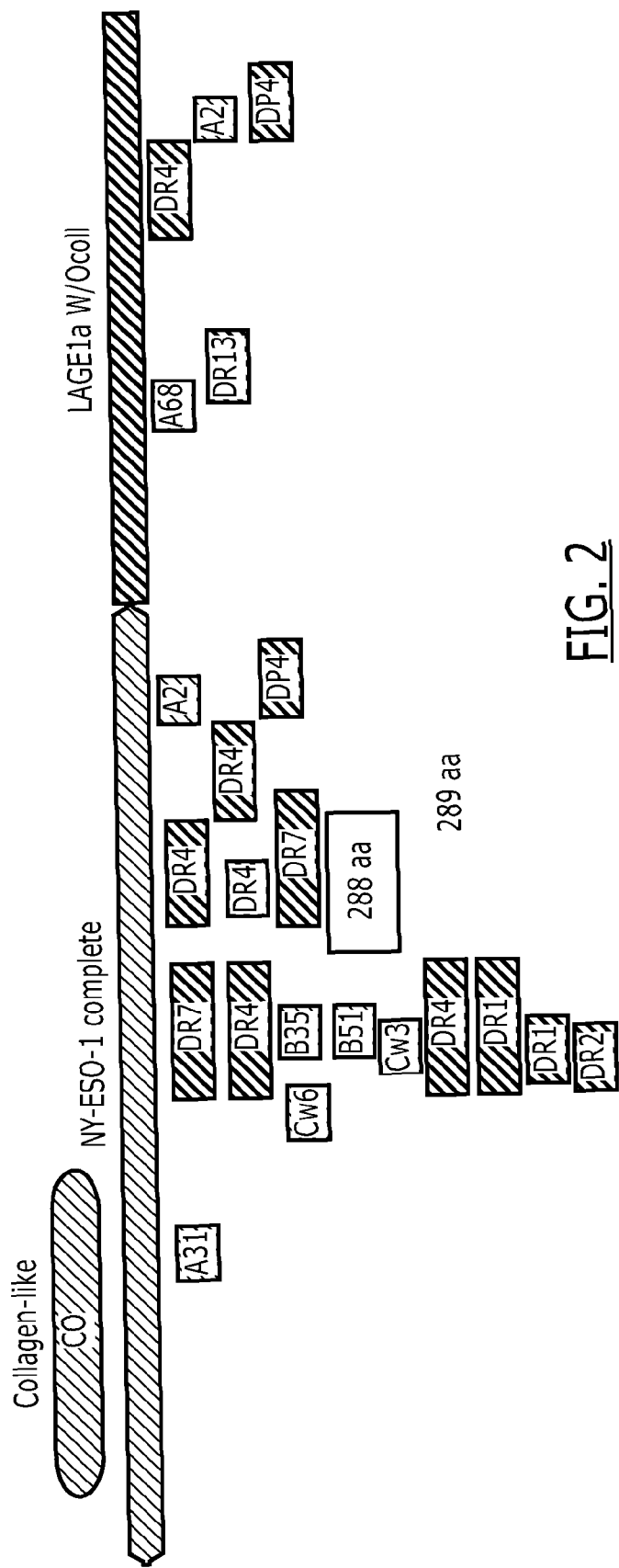
FIG. 2 shows construct A, a fusion protein comprising full length NY-ESO-1 and truncated LAGE-1, such as LAGE-1a. In this embodiment, the C-terminus of the NY-ESO-1 is fused to the N-terminus of truncated LAGE-1, together with a Histidine affinity tag to provide a fusion protein of 288 amino acids in length. Further details of construct A are given in Table 1 (SEQ ID NO:1; SEQ ID NO:3).
Figure 3:
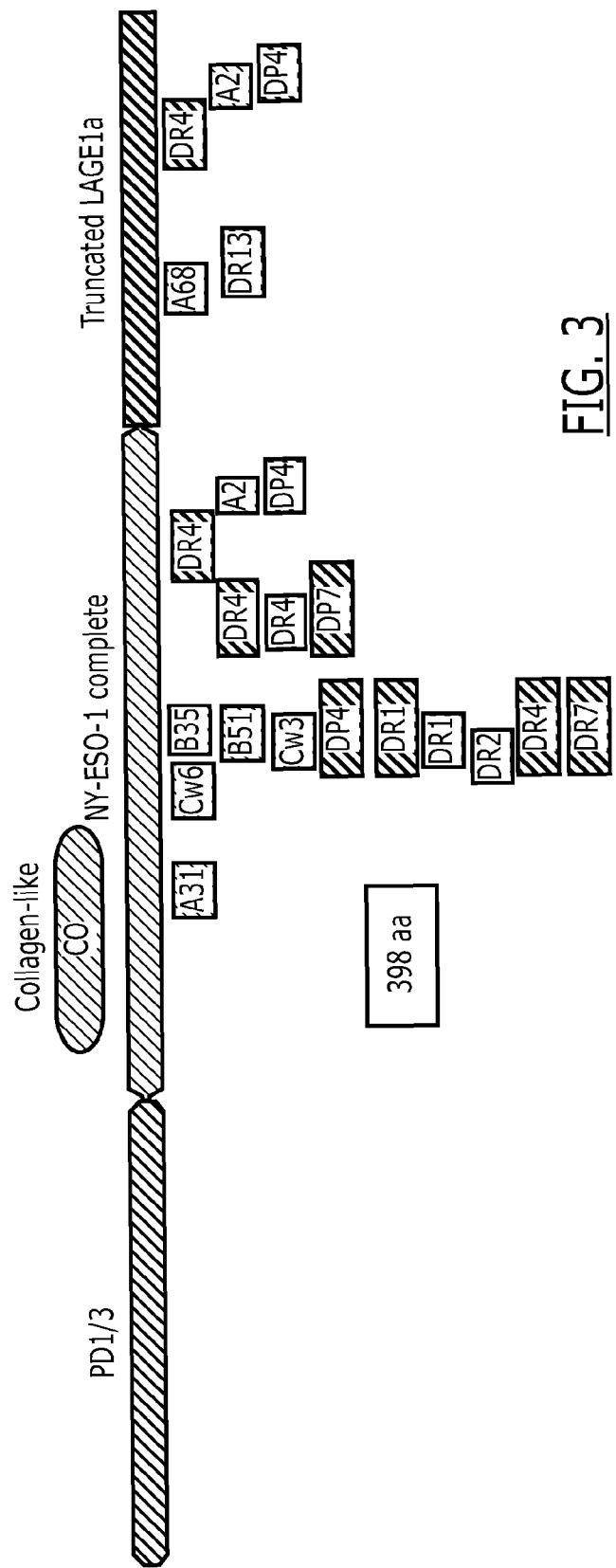
FIG. 3 shows construct B, a fusion protein comprising the first third of protein D without its secretion signal (for example amino acids 20 to 127), full length NY-ESO-1 and truncated LAGE-1, such as LAGE-1a. In this embodiment, amino acid 127 of protein D is fused to the N-terminus of NY-ESO-1, the C-terminus thereof being fused to the N-terminus of truncated LAGE-1, to provide a fusion protein of 398 amino acids in length. Further details of construct B are given in Table 1 in section 1.6 (SEQ ID NO:2; SEQ ID NO:4).
Figure 4:
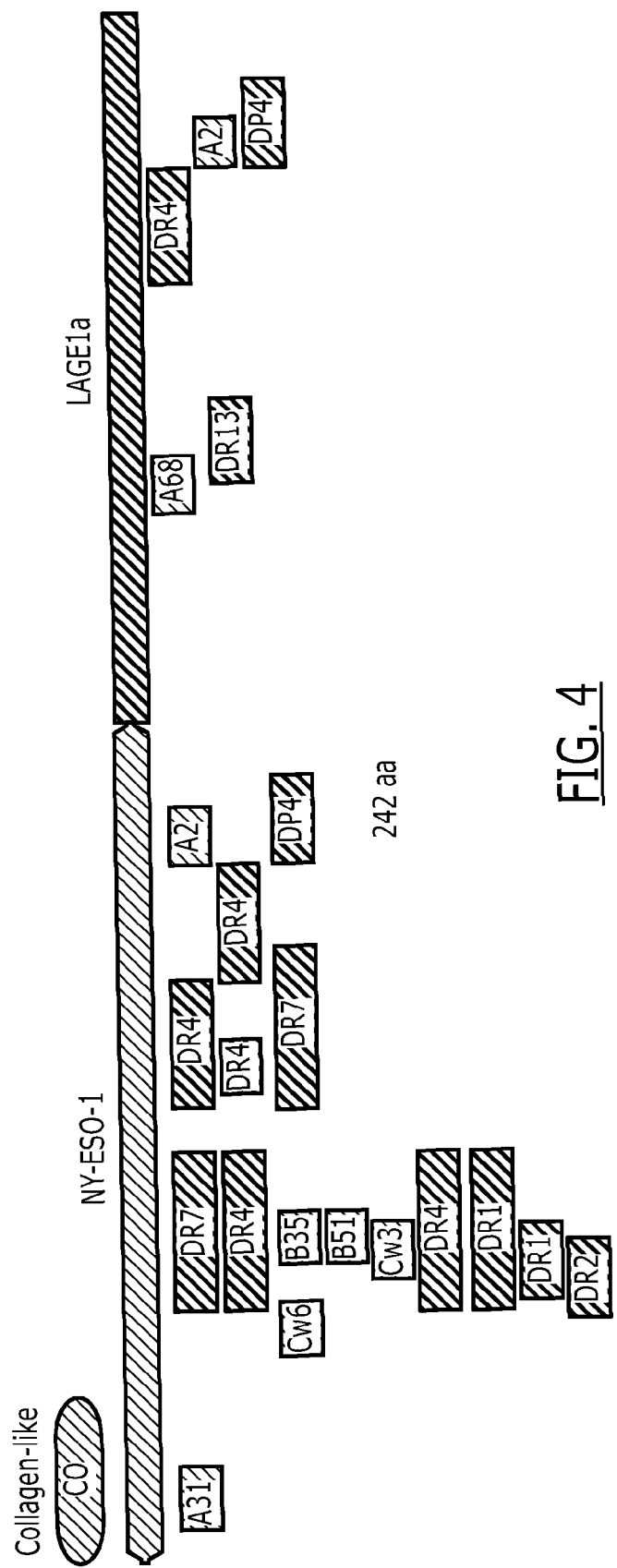
FIG. 4 shows construct C, a fusion protein comprising partially truncated NY-ESO-1 and truncated LAGE-1, such as LAGE-1 a. In this embodiment, the C-terminus of partially truncated NY-ESO-1 is fused to the N-terminus of truncated LAGE-1, to provide a fusion protein of 242 amino acids in length. Further details of construct C are given in Table 1 (SEQ ID NO:5; SEQ ID NO:7).
Figure 5:
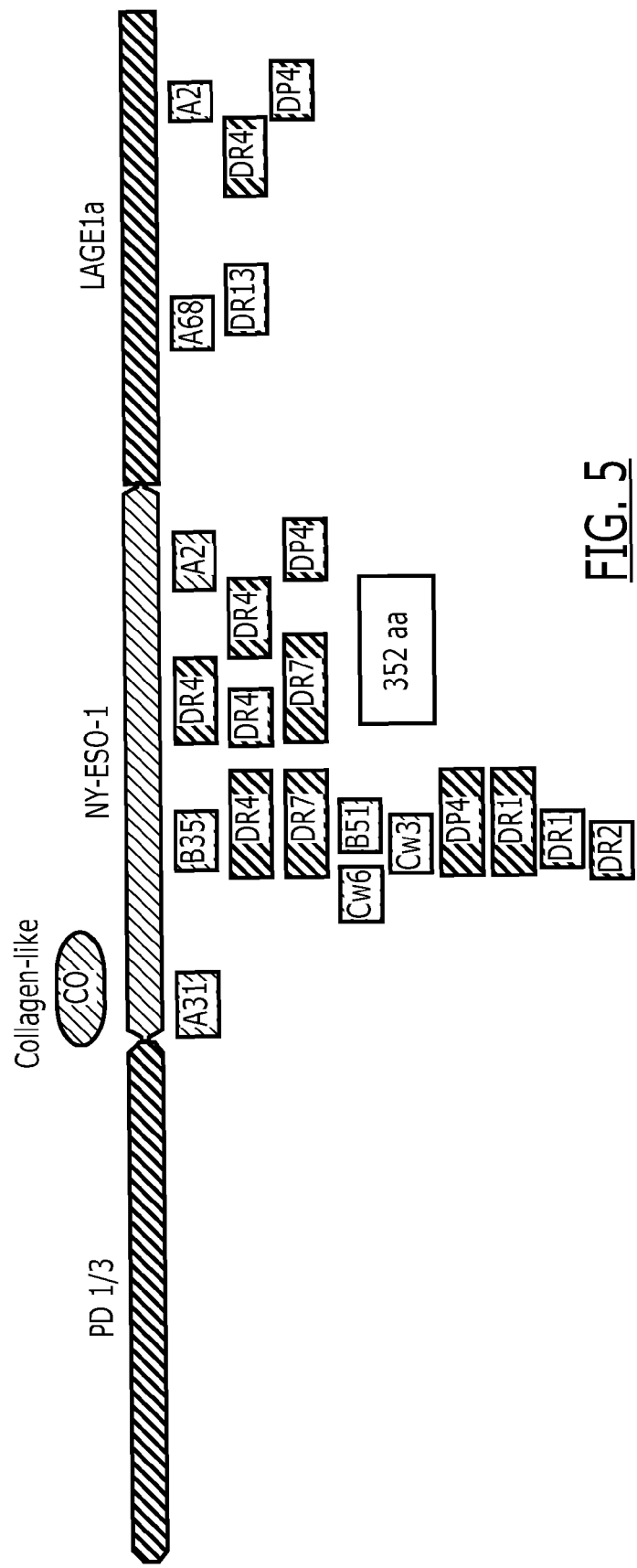
FIG. 5 shows construct D, a fusion protein comprising the first third of protein D without its secretion signal (for example amino acids 20 to about or approximately 127), partially truncated NY-ESO-1 and truncated LAGE-1, such as LAGE-1a. In this embodiment, amino acid 127 of protein D is fused to the N-terminus of partially truncated NY-ESO-1, the C-terminus thereof being fused to the N-terminus of the truncated LAGE-1, to provide a fusion protein of 352 amino acids in length. Further details of this embodiment are given in Table 1 (SEQ ID NO:6; SEQ ID NO:8).
Figure 6:
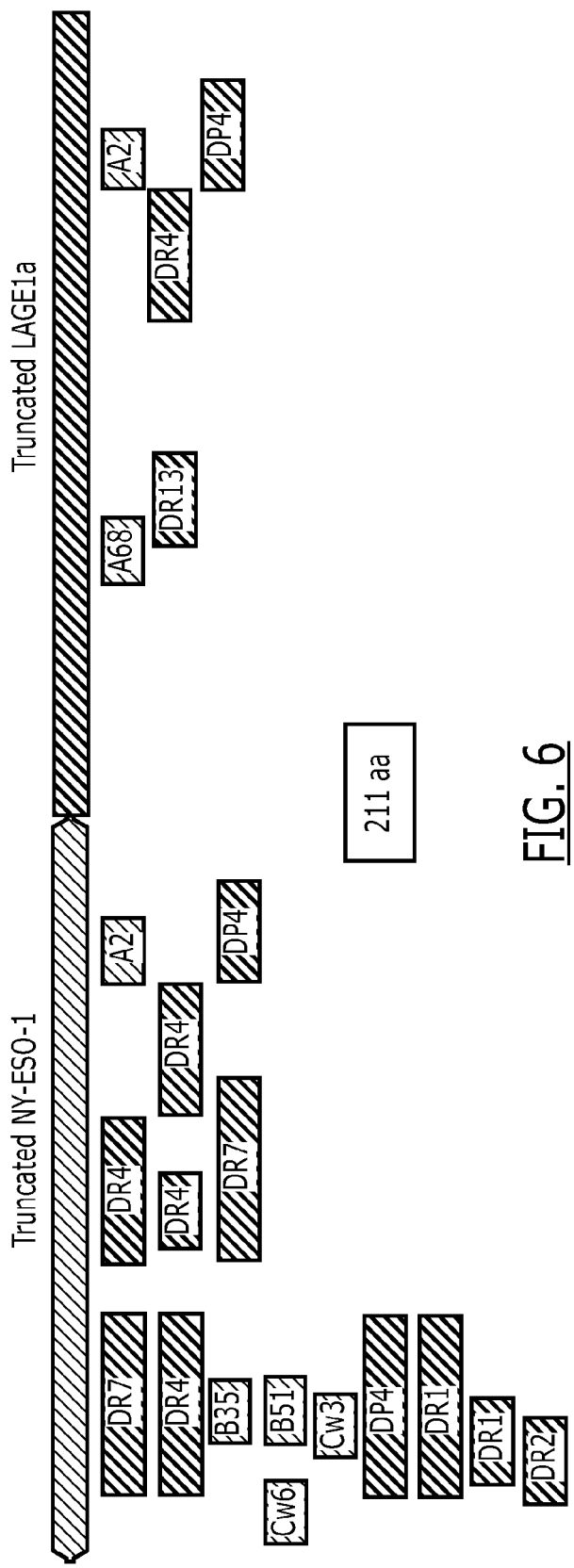
FIG. 6 shows construct E, a fusion protein comprising truncated NY-ESO-1 and truncated LAGE-1, such as LAGE-1a. In this embodiment, the C-terminus of truncated NY-ESO-1 is fused to the N-terminus of truncated LAGE-1, to provide a fusion protein of 211 amino acids in length. Further details of construct E are given in Table 1 (SEQ ID NO:9; SEQ ID NO:11).
Figure 7:
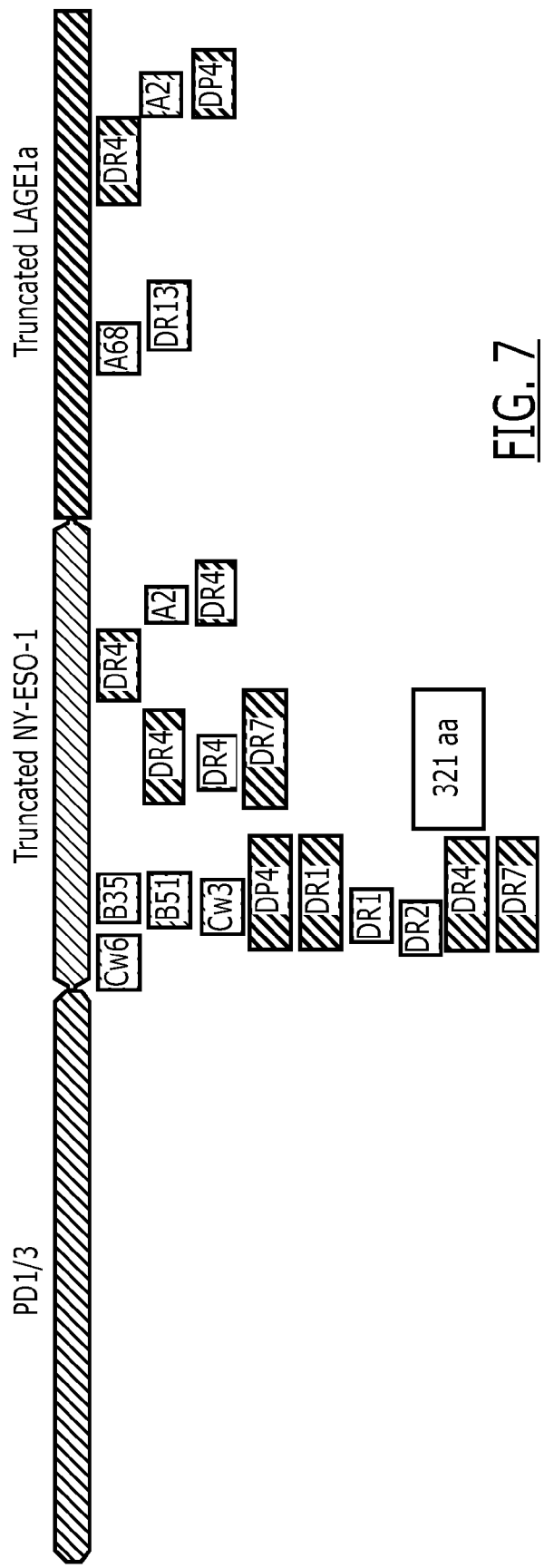
FIG. 7 shows construct F, a fusion protein comprising the first third of protein D without its secretion signal (for example amino acids 20 to about or approximately 127), truncated NY-ESO-1 and truncated LAGE-1, such as LAGE-1a. In this embodiment, amino acid 127 of protein D is fused to the N-terminus of truncated NY-ESO-1, the C-terminus thereof being fused to the N-terminus of truncated LAGE-1, to provide a fusion protein of 321 amino acids in length. Further details of construct F are given in Table 1 (SEQ ID NO:10; SEQ ID NO:12).
Figure 8:
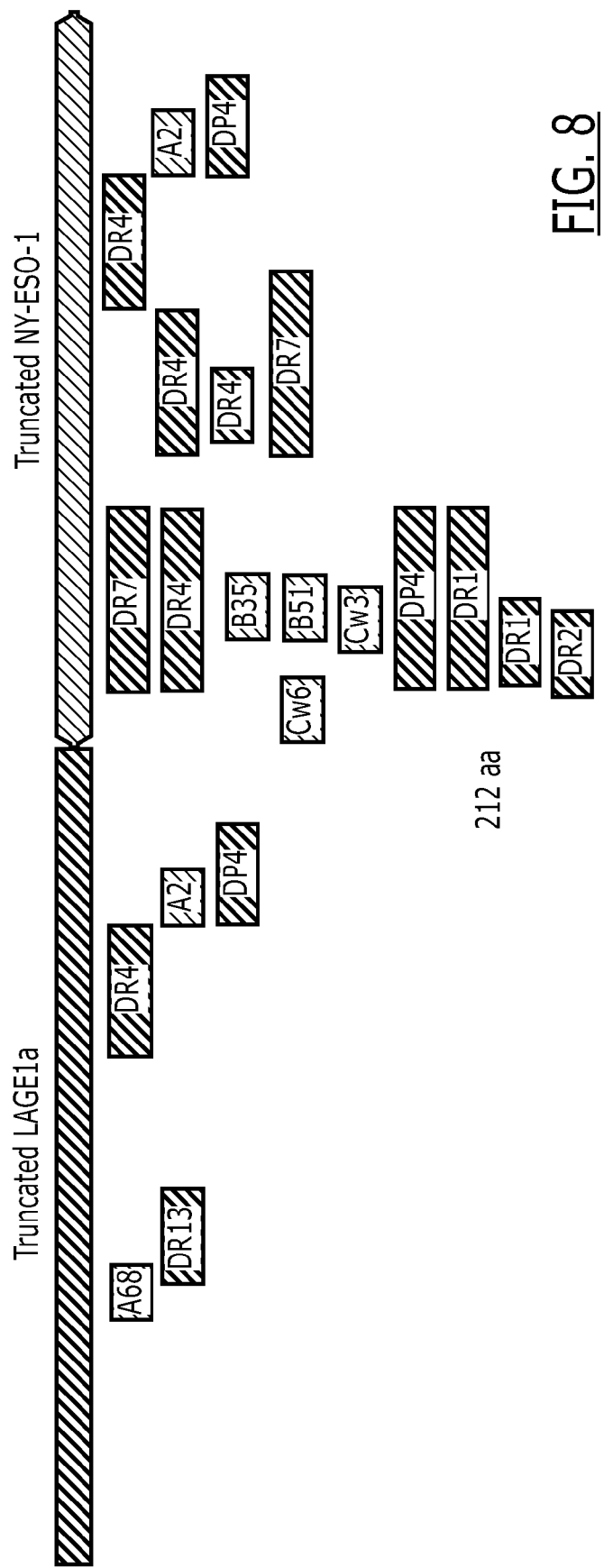
FIG. 8 shows an alternative embodiment of construct E, namely E', in which the C-terminus of truncated LAGE-1 is fused to the N-terminus of truncated NY-ESO-1, to provide a fusion protein of 212 amino acids in length. Further details of this embodiment, construct E', are given in Table 1 (SEQ ID NO:21; SEQ ID NO:23).
Figure 9:
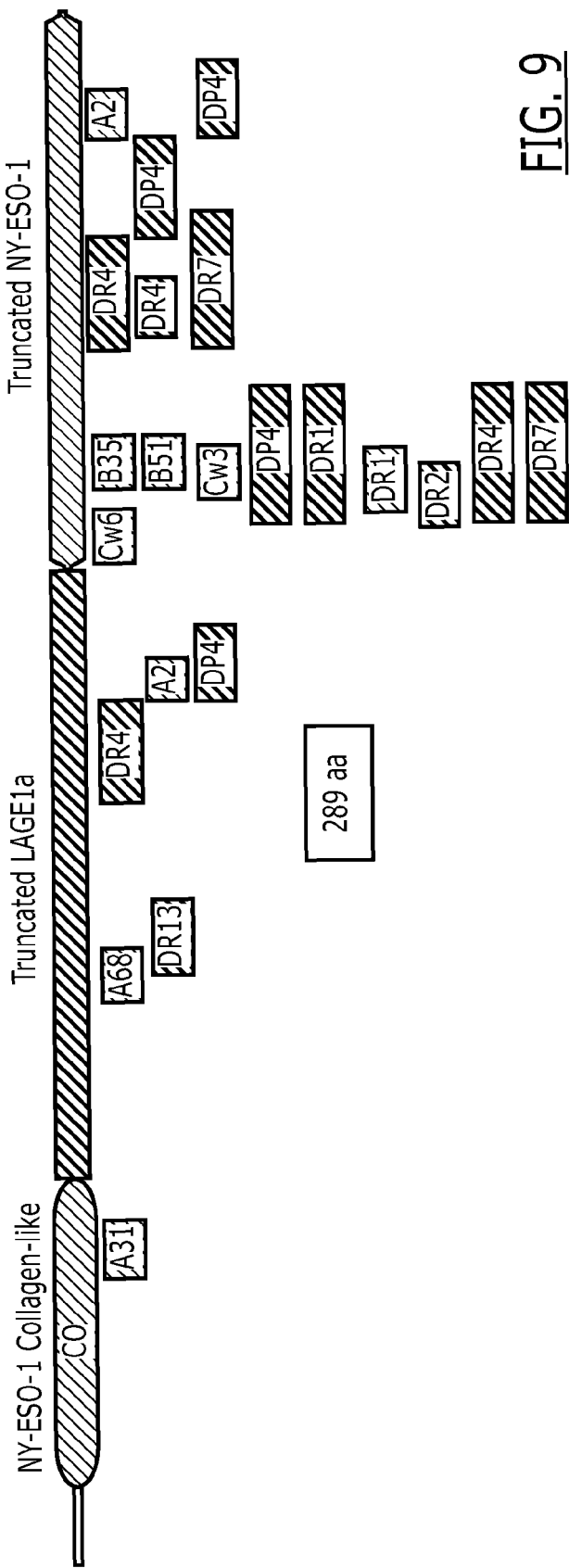
FIG. 9 shows construct G, a fusion protein comprising truncated NY-ESO-1, truncated LAGE-1, such as LAGE-la and the collagen-like region, such as the collagen region from NY-ESO-1. In this embodiment, the C-terminus of the collagen-like region is, for example, fused to the N-terminus of truncated LAGE-1. In turn the C-terminus of the truncated LAGE-1 is fused to the N-terminus of truncated NY-ESO-1, to provide a fusion protein of 289 amino acids in length. Further details of construct G are given in Table 1 (SEQ ID NO:13; SEQ ID NO:15).
Figure 10:
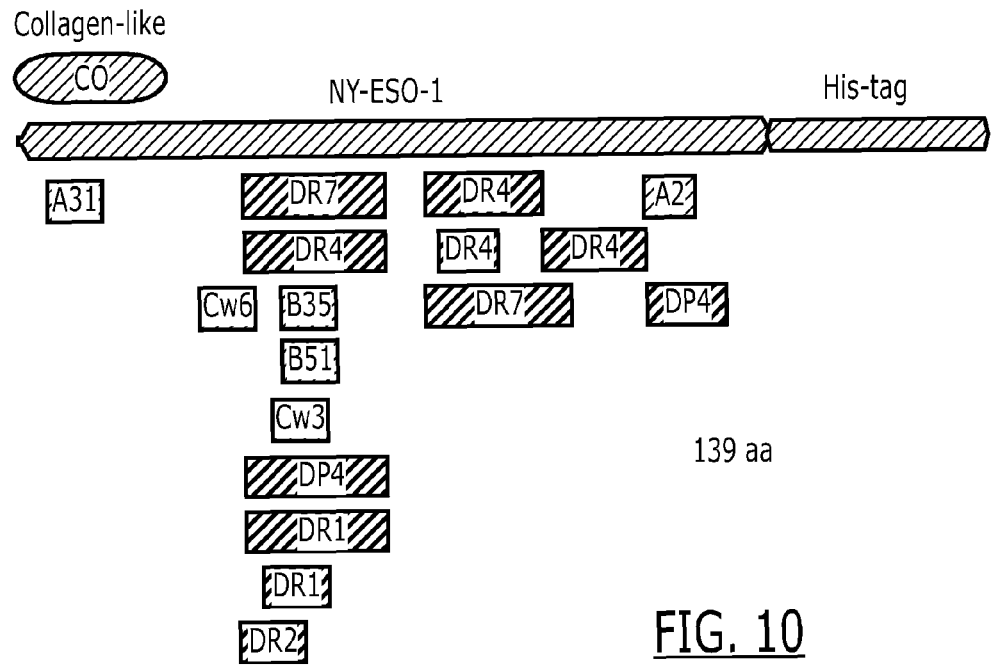
FIG. 10 shows a schematic of an exemplary recombinant polypeptide comprising NY-ESO-1 with a partially truncated collagen like domain. The epitopes shown in FIGS. 10-13 are merely representative of epitopes reported for the protein and have not been confirmed by experimentation.
Figure 11:
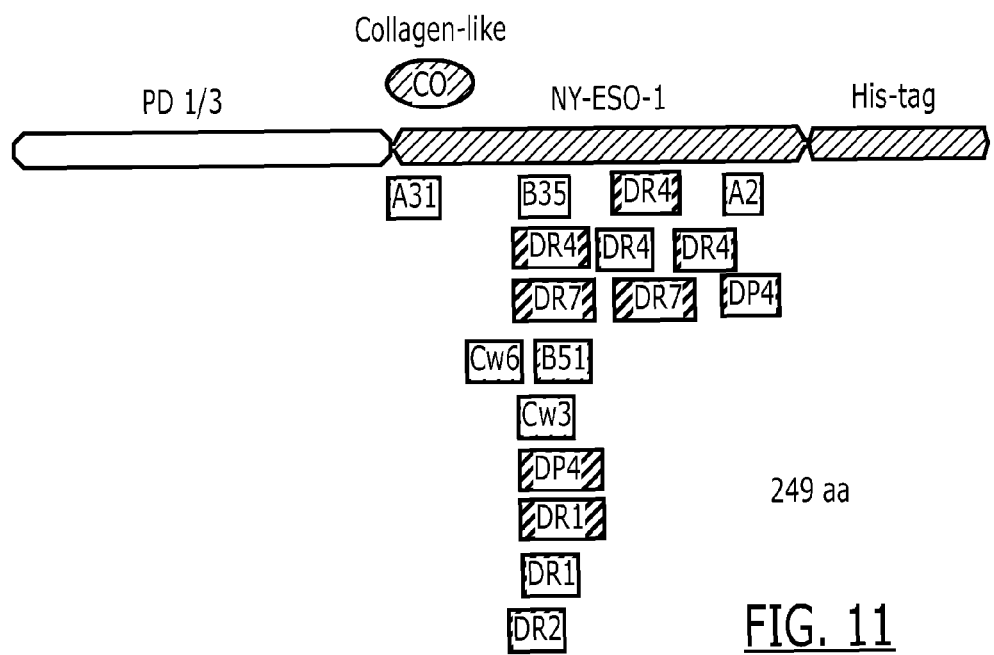
FIG. 11 shows a schematic of an exemplary fusion protein comprising the first third of protein D without its secretion signal (for example amino acids 20 to about or approximately 127) and NY-ESO-1 with a partially truncated collagen-like domain.
Figure 12:
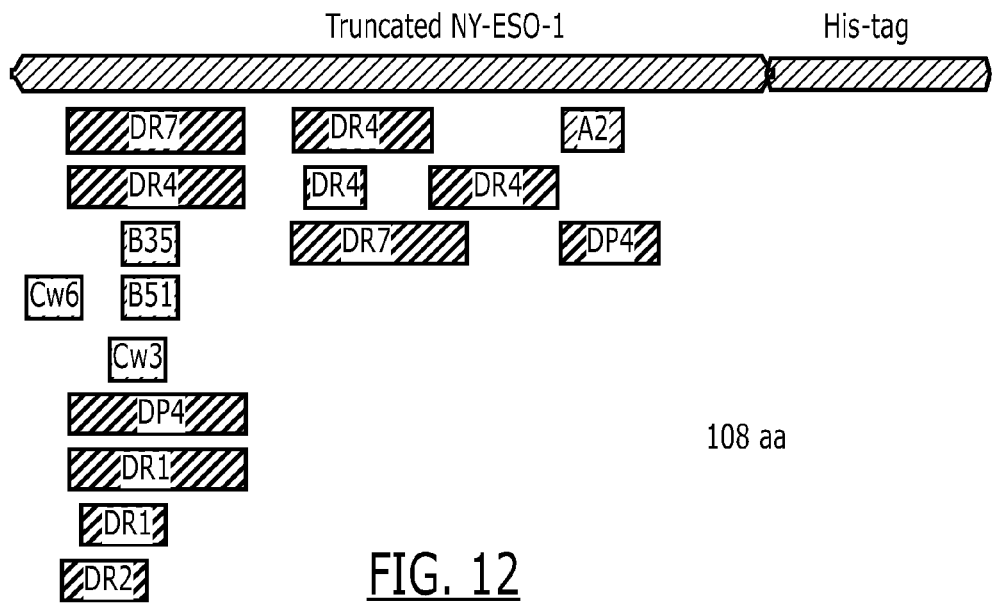
FIG. 12 shows a schematic of an exemplary recombinant polypeptide comprising NY-ESO-1 with a partially truncated collagen-like domain.
Figure 13:
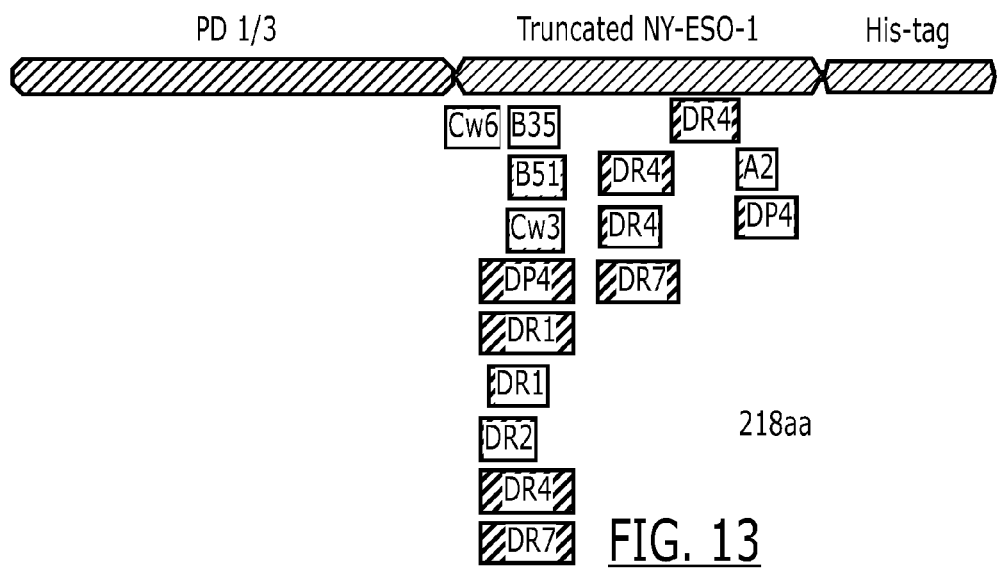
FIG. 13 shows a schematic of an exemplary fusion protein comprising the first third of protein D without its secretion signal (for example amino acids 20 to about or approximately 127) and NY-ESO-1 with a truncated collagen-like domain.
Figure 14:
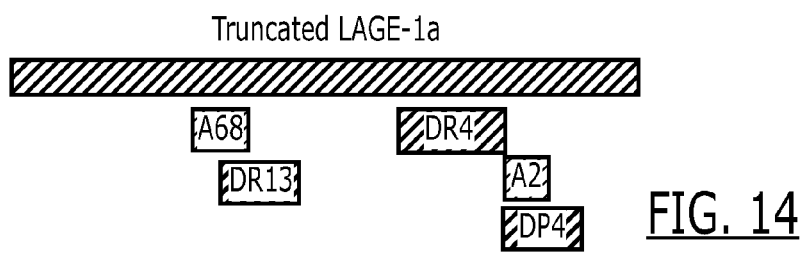
FIG. 14 is a schematic that shows a number of epitopes identified within the truncated LAGE-1 a protein. These epitopes are merely representative of epitopes reported for the protein thus the list is not exhaustive. For the avoidance of doubt, the epitopes reported and/or listed in the figures may or may not have not been confirmed by experimentation (i.e., they may have been predicted, etc.), unless otherwise stated herein. The complete LAGE-1a amino acid sequence is set forth in the sequence listing as SEQ ID NO:58. The complete LAGE-1b amino acid sequence (LAGE-1b not depicted in this Figure) is set forth in the sequence listing as SEQ ID NO:71.
Figure 15:
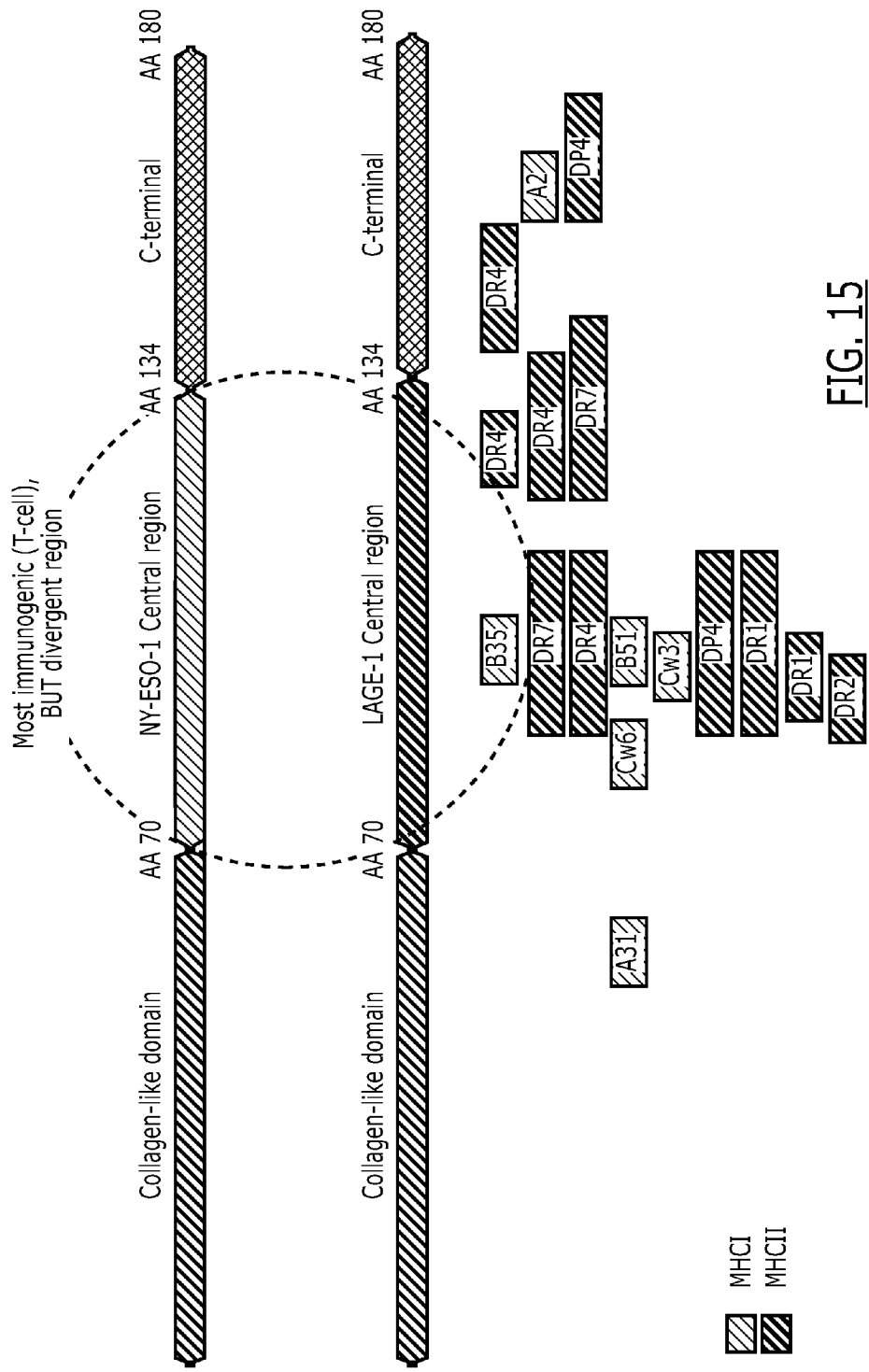
FIG. 15 shows a schematic of both NY-ESO-1 and LAGE-1, as well as a number of MHC (major histocompatibility complex) class I and II epitopes. These epitopes are merely representative of epitopes reported for the protein thus the list is not exhaustive; one or more of the epitopes reported and/or listed have not been confirmed by experimentation.
Figure 16:
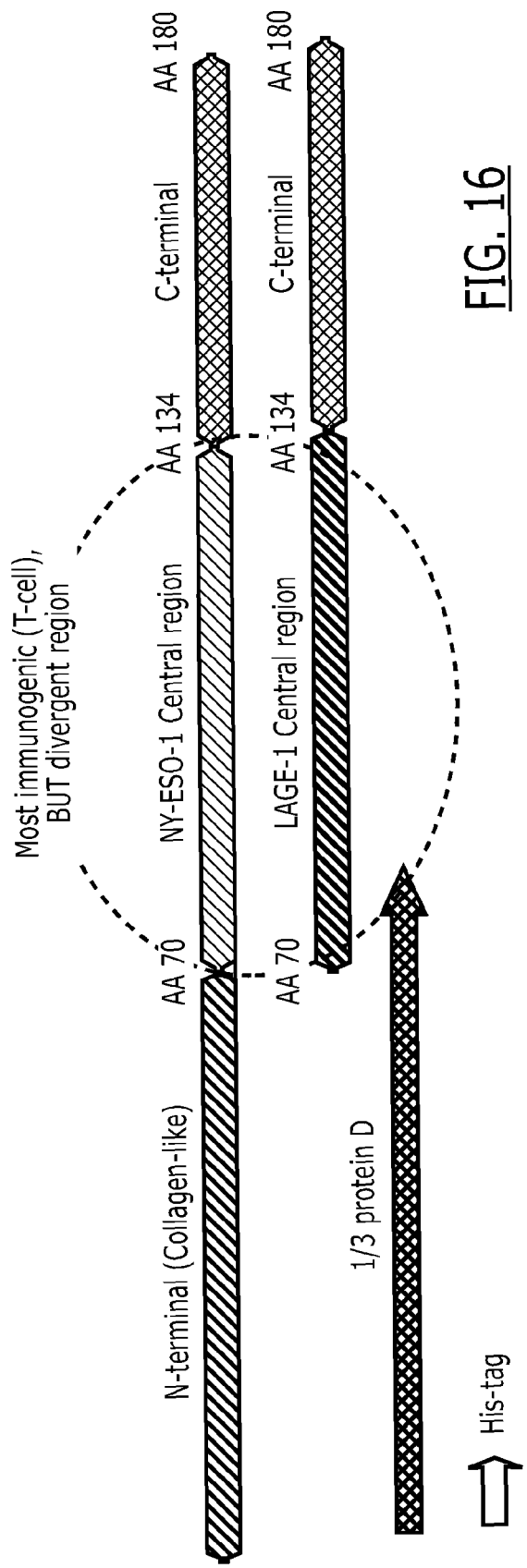
FIG. 16 shows a schematic of the NY-ESO-1/LAGE-1 fusion design.
Figure 17:
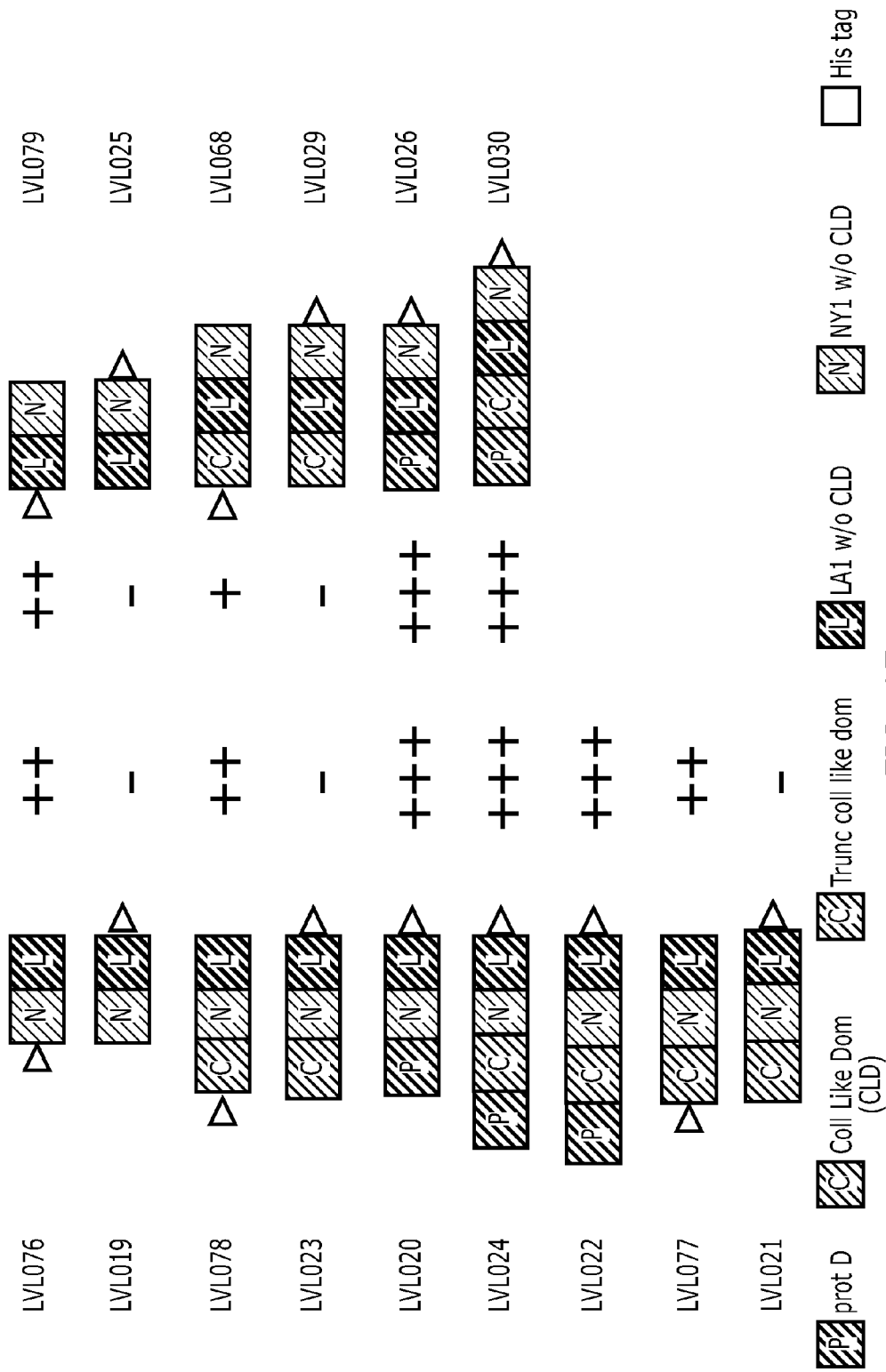
FIG. 17 summarizes in schematic fashion fifteen constructs and their production levels. P =protein D; C (grey box) =NY-ESO-1 collagen-like domain; C (white box) = truncated collagen like domain; L =Lage 1 without the collagen like domain; N =NY-ESO-1 without the collagen like domain; black arrow =poly histidine tag; (−) =low production; (+) =some production; (++) =high production; (+++) = best production. The amino acid sequences for eight of the constructs and the nucleotide sequences encoding them are summarized in Table 4 and the sequence listing.

Several NY-ESO-1/LAGE-1 fusion proteins were designed with and without the collagen-Like domain, and with and without the end terminus of protein D as summarized in FIG. 17. The designed constructs were codon optimized for expression in *Escherichia coli*. The synthetic gene was assembled from oligonucleotides and/or PCR products. The fragment was cloned into pGA4 backbone (AmpR) using Kpnl and Sacl restriction sites with the addition of Ndel and Xhol sites in the 5' end and the 3' end of the optimized gene respectively.

The plasmid DNA was purified from transformed bacteria and concentration determined by UV spectrometry. The final construct was verified by sequencing. The optimized coding sequence for the different NY/LAGE chimeric constructs was subcloned directly into pET19 (AmpR) multiple cloning site using Ndel and Xhol restriction sites to get the NY/LAGE chimer expression plasmids. For cloning into pET26, PCR primers were designed in order to ad N-terminal Histidine-tail. This amplification resulted in the addition of the 6 Histidines tail in phase with the coding region of the different constructs. This amplified fragment was enzymatically digested with Ndel/Xhol restriction enzymes and the different NY/LAGE chimeric constructs were subsequently cloned into pET26 (KanR) multiple cloning site to get the expression plasmid. The final constructs were verified by sequencing.

Shake-Flask Production. Growth and Induction of Bacterial Host Strain

Culture

Bacteria were grown on 800 ml of Luria-Bertani (LB) broth (BD)+1% (w/v) glucose (Laboratoire MAT, catalogue number: GR-0101)+antibiotic (Carbenicillin 100 μg/ml for pET19, kanamycin 40 μg/ml for pET26), in 2.5 L shaking flask. Cultures were incubated at 37° C. for BLR (DE3) cells until an $O.D._{600nm}$ around 0.8.

Induction

At $O.D._{600nm}$ around 0.8, the cultures BLR (DE3) were induced at 1 mM isopropyl β-D-1-thiogalactopyranoside (IPTG; EMD Chemicals Inc., catalogue number: 5815) and incubated for 16-18 hours at 16° C. 5 to 15 mg of specific protein/800 ml have been obtained with construct LVL106, 151, 155 and 157. The protein production for each construct is summarized in FIG. 17.

Example 2

Summary of Preliminary Purification and Stability

Extraction and Purification of the Protein

Cells are harvested by centrifugation then disrupted by physical or chemical means and the resulting crude extract retained to isolate the polypeptide of interest.

Purification

The expressed recombinant proteins were solubilized with guanidine hydrochloride solution and loaded on an Immobilized Metal Affinity Chromatography (IMAC) resin. Proteins were then washed on column with 8M and 4M urea solutions before elution by increasing imidazole concentration. Proteins were then desalted in the final 4M urea buffer, pH 7.0 for further use. Purification was evaluated by SDS PAGE and Western Blot, to verify the purity and the identity of the proteins.

Stability Test of Purified Fusion Protein

Stability assays were performed at 37° C. and proteins were evaluated by SDS-PAGE. Preliminary stability assay did not reveal major issue.

Preliminary Solubilization Assay

The solubility of the proteins was evaluated as summarized in the following Chart.

CHART 1

Fusion Protein Solubility.

| BUFFER | CONSTRUCT | | | | | | | |
|---|---|---|---|---|---|---|---|---|
| | LVL076 | LVL079 | LVL78 | LVL68 | LVL020 | LVL26 | LVL024 | LVL30 |
| PBS 1X; 1 mM TCEP; 1 mM EDTA, pH 7.03 | p | S | S | P | P | P | NT | P |
| 20 mM Bicine; 138 mM NaCl; 1 mM TCEP; 1 mM EDTA, pH 8.68 | p | S | P | P | P | P | NT | P |
| 20 mM imidazole; 138 mM NaCl; 1 mM TCEP; 1 mM EDTA, pH 5.99 | p | S | P | P | P | P | NT | P |
| 10 mM Sodium Ac; 5 mM NaCl; 1 mM TCEP; 1 mM EDTA, pH 4.99 | S | S | S | S | S | S | NT | S |

CHART 1-continued

Fusion Protein Solubility.

| BUFFER | CONSTRUCT | | | | | | | |
|---|---|---|---|---|---|---|---|---|
| | LVL076 | LVL079 | LVL78 | LVL68 | LVL020 | LVL26 | LVL024 | LVL30 |
| 10 mM citrate acid; 5 mM NaCl; 1 mM TCEP; 1 mM EDTA, pH 3.7 | NT | NT | S | S | NT | NT | NT | S |

Key:
P precipate;
S no precipitate;
NT not tested.

Example 3

IM Immunization With Fusion Proteins

The fusion proteins were evaluated preclinically in a mouse model involving a series of intramuscular immunizations screening experiments, as described below. The mouse model chosen was CB6F1, a first generation resulting from the cross of C57BL6 mice and Balb/c mice. Such mice are commercially available from Charles River Laboratories, Inc., 251 Ballardvale Street, Wilmington, Mass. 01887-1000. The chosen tumor cell line was B16 (Mouse melanoma cell line), a transplantable murine melanoma commercially available for the study of cancer therapies.

Screening #1

Experimental Design. In a 76-day trial, CB6F1 mice were used to assess each of LVL076, LVL079, LVL078, LVL068, LVL020, LVL026, LVL024, LVL030 to determine whether intramuscular immunization with the fusion protein plus adjuvant conferred protection against subcutaneous challenge with transplanted tumor cells (B16/NYESO1). As planned, mice were to be immunized intramuscularly with 50 µL injections containing 15 µg protein and an adjuvant. The adjuvant selected was AS15. AS15 is a liposomal adjuvant formulation comprising QS21, 3D-MPL and CpG.

In this particular trial, protein concentrations were determined spectrophotometrically using standard procedures (Table 6, COLUMN A) and the volumes estimated to contain 15 µg of each protein were computed accordingly (COLUMN B). Subsequent to the immunization of the mice, protein concentration was retested using a bicinchoninic acid (BCA) assay from a commercial supplier using the manufacturer's instructions (COLUMN C). Based on the BCA assay results, the µg of protein per immunization were recomputed (COLUMN D). Due to the variance between the spectrophotometrically-determined concentration values and those obtained by BCA, it was decided to use the BCA assay for all further concentration determinations.

TABLE 6

| Protein | COLUMN A Concentration by Spectro-photometry µg/mL | COLUMN B Computed volume protein solution/ mouse for immunization mL | COLUMN C Con-centration by BCA µg/mL | COLUMN D Dose of protein injected per mouse re-computed via BCA assay µg |
|---|---|---|---|---|
| NY-ESO-1 | 1220 | 12.3 | 1821 | 22.4 |
| LVL075 | 1569 | 9.6 | 849 | 8.2 |
| LVL076 | 852 | 17.6 | 665 | 11.7 |
| LVL078 | 708 | 21.2 | 770 | 16.3 |
| LVL020 | 698 | 21.5 | 416 | 8.9 |
| LVL024 | 1399 | 10.7 | 1076 | 11.5 |
| LVL079 | 491 | 30.5 | 309 | 9.4 |
| LVL068 | 1181 | 12.7 | 975 | 12.4 |
| LVL026 | 1471 | 14.8 | 1077 | 15.9 |
| LVL030 | 1116 | 11.6 | 862 | 10.0 |

Trials were carried out with fusion proteins set forth in 1A and 1 B, below. Mice were divided into groups of 15 mice/group. Mice were immunized on day 0 and again on day 14 as follows:

Trial 1A
LVL079
LVL026
LVL068
LVL030
Trial 1B
LVL076
LVL020
LVL078
LVL024
Controls
Antigen buffer/AS15 buffer
Full length NY-ESO-1
LAGE-1a without the collagen-like domain (CLD)
MAGE A3

Figure 18:
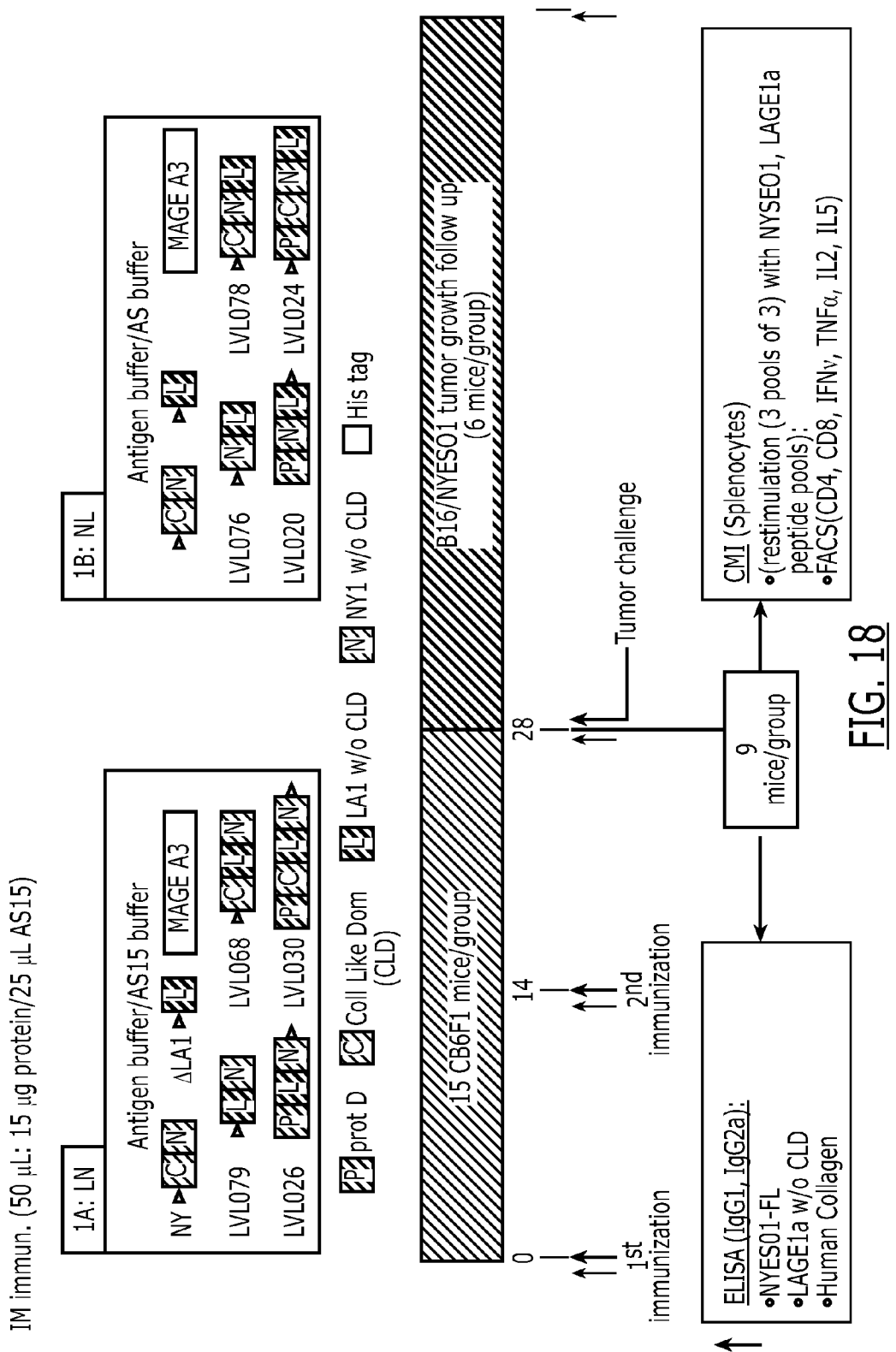
FIG. 18 summarizes screening #1, a 76-day trial using CB6F1 mice to assess each of LVL076, LVL079, LVL78, LVL68, LVL020, LVL26, LVL024, LVL30 to determine whether intramuscular immunization with the fusion protein plus adjuvant conferred protection against subcutaneous challenge with transplanted tumors (B16/NYES01).

Six mice/group were challenged with subcutaneous transplanted B16/NY-ESO-1 tumors on day 28. Antibody response to NY-ESO-1 full-length, LAGE-1a without collagen like domain, and human collagen was assessed at day 0, 14, 28, and 76 by ELISA (IgG1 and IgG2a). Cell-mediated response was assessed by FACS at day 28 using harvested splenocytes (restimulation—3 pools of 3—with NY-ESO-1 and LAGE-1a peptide pools). The experimental design of screening #1 is summarized in FIG. 18.

Results. Of the four controls, only full-length NY-ESO-1 conferred some protection compared with buffer. See FIG. 19. Of the groups of mice receiving either full-length NY-ESO-1 or LVL030, two from each group were tumor free at the end of the trial. Of the mice receiving LVL068, four were tumor free at the end of the study. LVL068 and LVL078 conferred longer survival compared with mice that received buffers. See FIG. 20. NY-ESO-1-specific immune responses were assessed by ELISA, FACS, and Western blot. LAGE-1a (without the collagen like domain)-specific immune responses were assessed by ELISA and FACS. See FIG. 21. These results are summarized in the following Chart.

CHART 2

Specific Immunity Summary.

| Immunogen | B16/NY-ESO-1 Protection | NY-ESO-1 Specific Immunity | LAGE1a Specific Immunity |
|---|---|---|---|
| LVL068 | ++ | ++ | ++ |
| LVL078 | + | ++ | ++ |
| LVL076 | + | ++ | + |
| LVL024 | + | ++ | + |
| LVL030 | + | ++ | + |
| LVL020 | + | + | + |
| LVL079 | − | + | + |
| LVL026 | − | + | + |

Key:
(−) - lowest response;
(+) - medium response;
(++) - highest response.

Screening #2

Experimental Design. In a 105-day trial, CB6F1 mice were used to assess each of LVL076, LVL078, LVL068, and LVL024 to determine whether intramuscular immunization with the fusion protein plus adjuvant conferred protection against subcutaneous challenge with B16/NYESO1 transplanted tumor cells (after two immunizations) or with B16/LAGE-1a tumor cells (after four immunizations). Specifically, mice were immunized intramuscularly with 50 µL injections containing 15 µg protein and 25 µL of AS15 adjuvant. Note: Protein concentrations were determined for this and subsequent experiments via a commercially available BCA assay (using the manufacturer's instructions).

Mice were divided into groups of 29 mice/group. Mice were immunized on day 0, 14, 28, and 42 as follows:
Trial
LVL076
LVL068
LVL078
LVL024
Controls
Antigen buffer/AS15 buffer
Full length NY-ESO-1
LAGE-1a without the collagen-like domain (CLD)
MAGE A3

Ten mice/group were challenged with subcutaneous transplanted B16/NY-ESO-1 tumor cells on day 28. Nine mice/group were challenged with subcutaneous transplanted B16/LAGE-1A tumor cells on day 56. Sera was taken and antibody response to (i) NY-ESO-1 full-length, (ii) LAGE-1a without collagen like domain, and (ii) human collagen was assessed at day 0, 14, 28, 42 56, 84 and 105 by ELISA (IgG1 and IgG2a). The experimental design of screening #2 is summarized in FIGS. 22 and 23.

Results

B16-NYESO1 Tumor Challenge.

Of the mice receiving LVL078, two were tumor free for over 50 days post B16-NY-ESO-1 challenge. Of the mice receiving either full-length NY-ESO-1 or LVL024, two from each group were tumor free for over 50 days, three were alive. Of the mice receiving LVL068, three were tumor free and four were alive. Of the mice receiving LVL076, 3 were tumor free and five were alive. See FIG. 24.

B16-LAGE1a Tumor Challenge.

All of the mice receiving LVL076 or LAGE-1a without the collagen like region were dead earlier than day 40 post challenge. Of the mice receiving buffer alone, one survived tumor free to the end of the study. Of the mice receiving LVL024, one was tumor free at the end of the study. Of the mice receiving full-length NY-ESO-1, none were tumor free, but one was still alive at the end of the study. Of the mice receiving LVL078, one was tumor free. Of the mice receiving LVL068, three were tumor free. Of the mice receiving LVL076, three were tumor free at the end of the study. See FIG. 25. These results are summarized in the following Chart.

CHART 3

Protection versus B16-LAGE1a Tumor Challenge.

| | NY-ESO-1 | | LAGE-1a | |
|---|---|---|---|---|
| Immunogen | Protection | Specific Immunity | Protection | Specific Immunity |
| LVL068 | ++ | ++ | ++ | ++ |
| LVL078 | ++ | ++ | ++ | ++ |
| LVL024 | ± | ++ | − | + |
| LVL076 | + | + | − | + |

Key:
(−) - lowest;
(±) - next lowest response;
(+) - medium response;
(++) - highest response.

Human Collagen-Specific Immune Responses

To study whether the collagen like domain of NY-ESO-1 stimulated human collagen-specific immune responses, sera was collected and pooled 14 days post-inoculation from mice immunized with one of the following: (1) Buffers (control); (2) full-length NY-ESO-1; (3) LAGE-1a without the collagen like domain; (4) LVL068; (5) LVL078; (6) LVL024; (7) LVL076. ELISAs were carried out for each of these seven sera pools, as well as for a positive control containing mAb anti-human collagen I. The collagen like domain did not stimulate mouse anti-human collagen I antibody production. See FIG. 26. Similar studies (results not shown) were carried out for collagen III and collagen VI; neither mouse anti-human collagen III nor mouse anti-human collagen VI antibody production were detected.

Example 4

Refined Constructs

Modifications were carried out using routine cloning techniques on some of the constructs listed in Table 4. Specifically, LVL068, LVL030, LVL076, LVL078, LVL024 were modified to yield LVL155, LVL106, LVL156, LVL157, LVL151. There were two kinds of modifications, first the removal of 5 amino acid residues between protein D and the beginning of the chimers. For example, this modification was carried out with LVL024 (SEQ ID NO:74; SEQ ID NO:75) to yield LVL151 (SEQ ID NO:90; SEQ ID NO:91). Thus, LVL024 corresponds with LVL 151. The second type of modification was the removal of the amino acids between the his-tag and the beginning of the chimer. This modification was carried out with LVL068 (SEQ ID NO:80; SEQ ID NO:81) to yield LVL155 (SEQ ID NO:92; SEQ ID NO:93). Thus, LVL068 corresponds with LVL 151. Each fusion protein construct that was modified and the fusion protein construct to which it corresponds is set forth in Table 5 of the Description.

As is understood, the modifications described above are not expected to result in functional differences between a fusion protein and its corresponding modified fusion protein. Thus, it is expected that one may utilize each modified fusion protein listed on the right side of the Table 5 interchangeably with its corresponding fusion protein listed on the left hand side of the chart.

Example 5

Experimental Design. In a 105-day trial, CB6F1 mice are used to assess each of LVL068, LVL030, LVL076, LVL078, LVL024 and the modified LVL155, LVL106, LVL156, LVL157, LVL151 to study intramuscular immunization with the fusion protein plus adjuvant against subcutaneous challenge with B16/NYESO1 transplanted tumor cells (after two immunizations) or with B16/LAGE-1a tumor cells (after four immunizations). Specifically, mice are immunized intramuscularly with 50 µL injections containing 15 µg protein and 25 µL of AS15 adjuvant.

Mice are divided into groups of 29 mice/group. Mice are immunized on day 0, 14, 28, and 42 as follows:
Trial
LVL068
LVL030
LVL076
LVL078
LVL024
LVL155
LVL106
LVL156
LVL157
LVL151
Controls
Antigen buffer/AS15 buffer
Full length NY-ESO-1
LAGE-1a without the collagen domain
MAGE A3

Ten mice/group are challenged with subcutaneous transplanted B16/NY-ESO-1 tumor cells on day 28. Nine mice/group are challenged with subcutaneous transplanted B16/LAGE-1A tumor cells on day 56. To monitor specific immune response, sera can be taken and antibody response measured to (i) NY-ESO-1 full-length, (ii) LAGE-1a without collagen like domain, and (ii) human collagen at day 0, 14, 28, 42 56, 84 and 105 by ELISA (IgG1 and IgG2a).

The preceding examples are provided by way of illustration, not by way of limitation.

Within the present application, the article "a" and "an" are used herein to refer to one or more than one (i.e., to at least one) of the grammatical object of the article. By way of example, "an element" means one or more element. The terms "approximately" and "about" as used herein are intended to be optionally deletable or replaceable with the term "exactly", if required by the applicant, in every instance.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

We claim:

1. A fusion protein comprising an amino acid sequence selected from the group consisting of SEQ ID NO:79; SEQ ID NO:89; SEQ ID NO:81; SEQ ID NO:93; SEQ ID NO:85, and SEQ ID NO:97.

2. A composition comprising the fusion protein of claim 1, additionally comprising an adjuvant.

3. A composition comprising the fusion protein of claim 1, additionally comprising a pharmaceutically acceptable excipient.

4. A method for making the composition of claim 2 comprising formulating the fusion protein with an adjuvant.

5. A method for making the composition of claim 3 comprising formulating the fusion protein with a pharmaceutically acceptable excipient.

* * * * *

SEQUENCE LISTING

```
<160> NUMBER OF SEQ ID NOS: 98

<210> SEQ ID NO 1
<211> LENGTH: 867
<212> TYPE: DNA
<213> ORGANISM: Artificial Sequence
<220> FEATURE:
<223> OTHER INFORMATION: NY-ESO-1/LAGE construct

<400> SEQUENCE: 1
atgcaggcgg aaggccgtgg caccggtggt agcaccggcg atgcggatgg tccgggcggt      60
ccgggtattc cggacgggcc tggtggtaat gcgggtgggc caggtgaagc gggtgcgacc     120
ggtggtcgtg gtccgcgggg ggcaggcgca gcacgtgcat ctggtccggg tggtggtgca     180
ccgcgcggtc cgcatggtgg tgcggcgagc ggcctgaatg gttgctgccg ttgcggtgcg     240
cgtggtccgg aaagccgtct gctggaattt tatctggcca tgccgtttgc gaccccgatg     300
gaagcggaac tggcccgtcg tagcctggct caagatgcac cgccgctgcc ggttccgggc     360
gtgctgctga agaatttac cgtgagcggc aacattctga ccattcgtct gacggcggca     420
gaccatcgtc agctgcaact gagcattagc agctgcctgc aacagctgtc tctgctgatg     480
tggattaccc agtgctttct gccggtgttt ctggcccagc cgccgtctgg tcaacgtggt     540
ggcgcgcgtc gtccggattc tcgcctgctg gaactgcata ttaccatgcc gttcagctct     600
```

```
ccaatggagg ccgaattagt gcgtcgcatt ctgagccgtg atgcggcacc gctgccgcgt    660
ccaggtgcgg ttctgaaaga cttcaccgta tctggcaacc tgctgtttat ccgtctgacc    720
gcagcggacc accgccaatt acaattatct atcagctctt gtttacaaca actgtcgctg    780
ttaatgtgga tcactcaatg tttcctgcca gtattcctgg ctcaggcccc gagcggtcag    840
cgtcgtcacc accaccacca ccactaa                                        867
```

<210> SEQ ID NO 2
<211> LENGTH: 1197
<212> TYPE: DNA
<213> ORGANISM: Artificial Sequence
<220> FEATURE:
<223> OTHER INFORMATION: NY-ESO-1/LAGE construct

<400> SEQUENCE: 2

```
atggatccaa gcagccattc atcaaatatg gcgaataccc aaatgaaatc agacaaaatc     60
attattgctc accgtggtgc tagcggttat ttaccagagc atacgttaga atctaaagca    120
cttgcgtttg cacaacaggc tgattattta gagcaagatt tagcaatgac taaggatggt    180
cgtttagtgg ttattcacga tcactttttta gatggcttga ctgatgttgc gaaaaaattc    240
ccacatcgtc atcgtaaaga tggccgttac tatgtcatcg actttacctt aaaagaaatt    300
caaagtttag aaatgacaga aactttgaa acccaggcgg aaggccgtgg caccggtggt    360
agcaccggcg atgcggatgg tccgggcggt ccgggtattc cggacgggcc tggtggtaat    420
gcgggtgggc aggtgaagc gggtgcgacc ggtggtcgtg gtccgcgggg ggcaggcgca    480
gcacgtgcat ctggtccggg tggtggtgca ccgcgcggtc cgcatggtgg tgcggcgagc    540
ggcctgaatg gttgctgccg ttgcggtgcg cgtggtccgg aaagccgtct gctggaattt    600
tatctggcca tgccgtttgc gaccccgatg gaagcggaac tggcccgtcg tagcctggct    660
caagatgcac cgccgctgcc ggttccgggc gtgctgctga aagaattcac cgtgagcggc    720
aacattctga ccattcgtct gacggcggca gaccatcgtc agctgcaact gagcattagc    780
agctgcctgc aacagctgtc tctgctgatg tggattaccc agtgctttct gccggtgttt    840
ctggcccagc cgccgtctgg tcaacgtggt ggcgcgcgtc gtccggattc tcgcctgctg    900
gaactgcata ttaccatgcc gttcagctct ccaatggagg ccgaattagt gcgtcgcatt    960
ctgagccgtg atgcggcacc gctgccgcgt ccaggtgcgg ttctgaaaga cttcaccgta   1020
tctggcaacc tgctgtttat ccgtctgacc gcagcggacc accgccaatt acaattatct   1080
atcagctctt gtttacaaca actgtcgctg ttaatgtgga tcactcaatg tttcctgcca   1140
gtattcctgg ctcaggcccc gagcggtcag cgtcgtcacc accaccacca ccactaa     1197
```

<210> SEQ ID NO 3
<211> LENGTH: 288
<212> TYPE: PRT
<213> ORGANISM: Artificial Sequence
<220> FEATURE:
<223> OTHER INFORMATION: NY-ESO-1/LAGE construct

<400> SEQUENCE: 3

```
Met Gln Ala Glu Gly Arg Gly Thr Gly Gly Ser Thr Gly Asp Ala Asp
 1               5                   10                  15

Gly Pro Gly Gly Pro Gly Ile Pro Asp Gly Pro Gly Gly Asn Ala Gly
                20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Gly Gly Gly Ala Pro Arg Gly Pro
```

-continued

```
                  50                  55                  60
His Gly Gly Ala Ala Ser Gly Leu Asn Gly Cys Cys Arg Cys Gly Ala
 65                  70                  75                  80

Arg Gly Pro Glu Ser Arg Leu Leu Glu Phe Tyr Leu Ala Met Pro Phe
                 85                  90                  95

Ala Thr Pro Met Glu Ala Glu Leu Ala Arg Arg Ser Leu Ala Gln Asp
                100                 105                 110

Ala Pro Pro Leu Pro Val Pro Gly Val Leu Leu Lys Glu Phe Thr Val
                115                 120                 125

Ser Gly Asn Ile Leu Thr Ile Arg Leu Thr Ala Ala Asp His Arg Gln
130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Gly Gly Ala Arg Arg Pro Asp Ser Arg Leu Leu Glu Leu
                180                 185                 190

His Ile Thr Met Pro Phe Ser Ser Pro Met Glu Ala Glu Leu Val Arg
                195                 200                 205

Arg Ile Leu Ser Arg Asp Ala Ala Pro Leu Pro Arg Pro Gly Ala Val
                210                 215                 220

Leu Lys Asp Phe Thr Val Ser Gly Asn Leu Leu Phe Ile Arg Leu Thr
225                 230                 235                 240

Ala Ala Asp His Arg Gln Leu Gln Leu Ser Ile Ser Ser Cys Leu Gln
                245                 250                 255

Gln Leu Ser Leu Leu Met Trp Ile Thr Gln Cys Phe Leu Pro Val Phe
                260                 265                 270

Leu Ala Gln Ala Pro Ser Gly Gln Arg Arg His His His His His His
                275                 280                 285

<210> SEQ ID NO 4
<211> LENGTH: 398
<212> TYPE: PRT
<213> ORGANISM: Artificial Sequence
<220> FEATURE:
<223> OTHER INFORMATION: NY-ESO-1/LAGE construct

<400> SEQUENCE: 4

Met Asp Pro Ser Ser His Ser Ser Asn Met Ala Asn Thr Gln Met Lys
  1               5                  10                  15

Ser Asp Lys Ile Ile Ile Ala His Arg Gly Ala Ser Gly Tyr Leu Pro
                 20                  25                  30

Glu His Thr Leu Glu Ser Lys Ala Leu Ala Phe Ala Gln Gln Ala Asp
                 35                  40                  45

Tyr Leu Glu Gln Asp Leu Ala Met Thr Lys Asp Gly Arg Leu Val Val
 50                  55                  60

Ile His Asp His Phe Leu Asp Gly Leu Thr Asp Val Ala Lys Lys Phe
 65                  70                  75                  80

Pro His Arg His Arg Lys Asp Gly Arg Tyr Tyr Val Ile Asp Phe Thr
                 85                  90                  95

Leu Lys Glu Ile Gln Ser Leu Glu Met Thr Glu Asn Phe Glu Thr Gln
                100                 105                 110

Ala Glu Gly Arg Gly Thr Gly Gly Ser Thr Gly Asp Ala Asp Gly Pro
                115                 120                 125

Gly Gly Pro Gly Ile Pro Asp Gly Pro Gly Gly Asn Ala Gly Gly Pro
                130                 135                 140
```

```
Gly Glu Ala Gly Ala Thr Gly Gly Arg Gly Pro Arg Gly Ala Gly Ala
145                 150                 155                 160

Ala Arg Ala Ser Gly Pro Gly Gly Ala Pro Arg Gly Pro His Gly
            165                 170                 175

Gly Ala Ala Ser Gly Leu Asn Gly Cys Cys Arg Cys Gly Ala Arg Gly
            180                 185                 190

Pro Glu Ser Arg Leu Leu Glu Phe Tyr Leu Ala Met Pro Phe Ala Thr
            195                 200                 205

Pro Met Glu Ala Glu Leu Ala Arg Arg Ser Leu Ala Gln Asp Ala Pro
210                 215                 220

Pro Leu Pro Val Pro Gly Val Leu Leu Lys Glu Phe Thr Val Ser Gly
225                 230                 235                 240

Asn Ile Leu Thr Ile Arg Leu Thr Ala Ala Asp His Arg Gln Leu Gln
                245                 250                 255

Leu Ser Ile Ser Ser Cys Leu Gln Gln Leu Ser Leu Leu Met Trp Ile
            260                 265                 270

Thr Gln Cys Phe Leu Pro Val Phe Leu Ala Gln Pro Pro Ser Gly Gln
            275                 280                 285

Arg Gly Gly Ala Arg Arg Pro Asp Ser Arg Leu Leu Glu Leu His Ile
290                 295                 300

Thr Met Pro Phe Ser Ser Pro Met Glu Ala Glu Leu Val Arg Arg Ile
305                 310                 315                 320

Leu Ser Arg Asp Ala Ala Pro Leu Pro Arg Pro Gly Ala Val Leu Lys
            325                 330                 335

Asp Phe Thr Val Ser Gly Asn Leu Leu Phe Ile Arg Leu Thr Ala Ala
            340                 345                 350

Asp His Arg Gln Leu Gln Leu Ser Ile Ser Ser Cys Leu Gln Gln Leu
            355                 360                 365

Ser Leu Leu Met Trp Ile Thr Gln Cys Phe Leu Pro Val Phe Leu Ala
            370                 375                 380

Gln Ala Pro Ser Gly Gln Arg Arg His His His His His
385                 390                 395

<210> SEQ ID NO 5
<211> LENGTH: 729
<212> TYPE: DNA
<213> ORGANISM: Artificial Sequence
<220> FEATURE:
<223> OTHER INFORMATION: NY-ESO-1/LAGE construct

<400> SEQUENCE: 5
atggcaggcg cagcacgtgc atctggtccg ggtggtggtg caccgcgcgg tccgcatggt      60
ggtgcggcga gcggcctgaa tggttgctgc cgttgcggtg cgcgtggtcc ggaaagccgt     120
ctgctggaat ttatctggc catgccgttt gcgaccccga tggaagcgga actggcccgt     180
cgtagcctgg ctcaagatgc accgccgctg ccggttccgg gcgtgctgct gaaagaattt     240
accgtgagcg gcaacattct gaccattcgt ctgacggcgg cagaccatcg tcagctgcaa     300
ctgagcatta gcagctgcct gcaacagctg tctctgctga tgtggattac ccagtgcttt     360
ctgccggtgt ttctggccca gccgccgtct ggtcaacgtg gtggcgcgcg tcgtccggat     420
tctcgcctgc tggaactgca tattaccatg ccgttcagct ctccaatgga ggccgaatta     480
gtgcgtcgca ttctgagccg tgatgcggca ccgctgccgc gtccaggtgc ggttctgaaa     540
gacttcaccg tatctggcaa cctgctgttt atccgtctga ccgcagcgga ccaccgccaa     600
ttacaattat ctatcagctc ttgtttacaa caactgtcgc tgttaatgtg gatcactcaa     660
```
tgtttcctgc cagtattcct ggctcaggcc ccgagcggtc agcgtcgtca ccaccaccac    720
caccactaa                                                             729

<210> SEQ ID NO 6
<211> LENGTH: 1059
<212> TYPE: DNA
<213> ORGANISM: Artificial Sequence
<220> FEATURE:
<223> OTHER INFORMATION: NY-ESO-1/LAGE construct

<400> SEQUENCE: 6
atggatccaa gcagccattc atcaaatatg gcgaataccc aaatgaaatc agacaaaatc     60
attattgctc accgtggtgc tagcggttat ttaccagagc atacgttaga atctaaagca    120
cttgcgtttg cacaacaggc tgattattta gagcaagatt tagcaatgac taaggatggt    180
cgtttagtgg ttattcacga tcactttta gatggcttga ctgatgttgc gaaaaaattc    240
ccacatcgtc atcgtaaaga tggccgttac tatgtcatcg actttacctt aaaagaaatt    300
caaagtttag aaatgacaga aaactttgaa accgcaggcg cagcacgtgc atctggtccg    360
ggtggtggtg caccgcgcgg tccgcatggt ggtgcgcgca cggcctgaa tggttgctgc    420 cgttgcggtg cgcgtggtcc ggaaagccgt ctgctggaat tatctggc catgccgttt    480 gcgaccccga tggaagcgga actggcccgt cgtagcctgg ctcaagatgc accgccgctg    540
ccggttccgg gcgtgctgct gaaagaattt accgtgagcg gcaacattct gaccattcgt    600
ctgacggcgg cagaccatcg tcagctgcaa ctgagcatta gcagctgcct gcaacagctg    660
tctctgctga tgtggattac ccagtgcttt ctgccggtgt ttctggccca gccgccgtct    720
ggtcaacgtg tggcgcgcg tcgtccggat tctcgcctgc tggaactgca tattaccatg    780
ccgttcagct ctccaatgga ggccgaatta gtgcgtcgca ttctgagccg tgatgcggca    840
ccgctgccgc gtccaggtgc ggttctgaaa gacttcaccg tatctggcaa cctgctgttt    900
atccgtctga ccgcagcgga ccaccgccaa ttacaattat ctatcagctc ttgtttacaa    960
caactgtcgc tgttaatgtg gatcactcaa tgtttcctgc cagtattcct ggctcaggcc   1020
ccgagcggtc agcgtcgtca ccaccaccac caccactaa                          1059

<210> SEQ ID NO 7
<211> LENGTH: 242
<212> TYPE: PRT
<213> ORGANISM: Artificial Sequence
<220> FEATURE:
<223> OTHER INFORMATION: NY-ESO-1/LAGE construct

<400> SEQUENCE: 7

Met Ala Gly Ala Ala Arg Ala Ser Gly Pro Gly Gly Gly Ala Pro Arg
 1               5                  10                  15

Gly Pro His Gly Gly Ala Ala Ser Gly Leu Asn Gly Cys Cys Arg Cys
            20                  25                  30

Gly Ala Arg Gly Pro Glu Ser Arg Leu Leu Glu Phe Tyr Leu Ala Met
        35                  40                  45

Pro Phe Ala Thr Pro Met Glu Ala Glu Leu Ala Arg Arg Ser Leu Ala
    50                  55                  60

Gln Asp Ala Pro Pro Leu Pro Val Pro Gly Val Leu Leu Lys Glu Phe
65                  70                  75                  80

Thr Val Ser Gly Asn Ile Leu Thr Ile Arg Leu Thr Ala Ala Asp His
                85                  90                  95

Arg Gln Leu Gln Leu Ser Ile Ser Ser Cys Leu Gln Gln Leu Ser Leu

```
            100                 105                 110
Leu Met Trp Ile Thr Gln Cys Phe Leu Pro Val Phe Leu Ala Gln Pro
            115                 120                 125

Pro Ser Gly Gln Arg Gly Gly Ala Arg Arg Pro Asp Ser Arg Leu Leu
        130                 135                 140

Glu Leu His Ile Thr Met Pro Phe Ser Ser Pro Met Glu Ala Glu Leu
145                 150                 155                 160

Val Arg Arg Ile Leu Ser Arg Asp Ala Ala Pro Leu Pro Arg Pro Gly
                165                 170                 175

Ala Val Leu Lys Asp Phe Thr Val Ser Gly Asn Leu Leu Phe Ile Arg
            180                 185                 190

Leu Thr Ala Ala Asp His Arg Gln Leu Gln Leu Ser Ile Ser Ser Cys
        195                 200                 205

Leu Gln Gln Leu Ser Leu Leu Met Trp Ile Thr Gln Cys Phe Leu Pro
    210                 215                 220

Val Phe Leu Ala Gln Ala Pro Ser Gly Gln Arg Arg His His His His
225                 230                 235                 240

His His

<210> SEQ ID NO 8
<211> LENGTH: 352
<212> TYPE: PRT
<213> ORGANISM: Artificial Sequence
<220> FEATURE:
<223> OTHER INFORMATION: NY-ESO-1/LAGE construct

<400> SEQUENCE: 8

Met Asp Pro Ser Ser His Ser Ser Asn Met Ala Asn Thr Gln Met Lys
1               5                   10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Ala
            100                 105                 110

Gly Ala Ala Arg Ala Ser Gly Pro Gly Gly Gly Ala Pro Arg Gly Pro
        115                 120                 125

His Gly Gly Ala Ala Ser Gly Leu Asn Gly Cys Cys Arg Cys Gly Ala
    130                 135                 140

Arg Gly Pro Glu Ser Arg Leu Leu Glu Phe Tyr Leu Ala Met Pro Phe
145                 150                 155                 160

Ala Thr Pro Met Glu Ala Glu Leu Ala Arg Arg Ser Leu Ala Gln Asp
                165                 170                 175

Ala Pro Pro Leu Pro Val Pro Gly Val Leu Leu Lys Glu Phe Thr Val
            180                 185                 190

Ser Gly Asn Ile Leu Thr Ile Arg Leu Thr Ala Ala Asp His Arg Gln
        195                 200                 205

Leu Gln Leu Ser Ile Ser Ser Cys Leu Gln Gln Leu Ser Leu Leu Met
    210                 215                 220
```

| Trp | Ile | Thr | Gln | Cys | Phe | Leu | Pro | Val | Phe | Leu | Ala | Gln | Pro | Pro | Ser |
| 225 | | | | 230 | | | | | 235 | | | | | 240 | |

Gly Gln Arg Gly Gly Ala Arg Arg Pro Asp Ser Arg Leu Leu Glu Leu
                245                 250                 255

His Ile Thr Met Pro Phe Ser Ser Pro Met Glu Ala Glu Leu Val Arg
            260                 265                 270

Arg Ile Leu Ser Arg Asp Ala Ala Pro Leu Pro Arg Pro Gly Ala Val
            275                 280                 285

Leu Lys Asp Phe Thr Val Ser Gly Asn Leu Leu Phe Ile Arg Leu Thr
    290                 295                 300

Ala Ala Asp His Arg Gln Leu Gln Leu Ser Ile Ser Ser Cys Leu Gln
305                 310                 315                 320

Gln Leu Ser Leu Leu Met Trp Ile Thr Gln Cys Phe Leu Pro Val Phe
                325                 330                 335

Leu Ala Gln Ala Pro Ser Gly Gln Arg Arg His His His His His His
            340                 345                 350

<210> SEQ ID NO 9
<211> LENGTH: 636
<212> TYPE: DNA
<213> ORGANISM: Artificial Sequence
<220> FEATURE:
<223> OTHER INFORMATION: NY-ESO-1/LAGE construct

<400> SEQUENCE: 9

```
atgggtgcgc gtggtccgga aagccgtctg ctggaatttt atctggccat gccgtttgcg    60
accccgatgg aagcggaact ggcccgtcgt agcctggctc aagatgcacc gccgctgccg   120
gttccgggcg tgctgctgaa agaatttacc gtgagcggca cattctgac cattcgtctg    180
acggcggcag accatcgtca gctgcaactg agcattagca gctgcctgca acagctgtct   240
ctgctgatgt ggattaccca gtgctttctg ccggtgtttc tggcccagcc gccgtctggt   300
caacgtggtg gcgcgcgtcg tccggattct cgcctgctgg aactgcatat taccatgccg   360
ttcagctctc caatggaggc cgaattagtg cgtcgcattc tgagccgtga tgcggcaccg   420
ctgccgcgtc caggtgcggt tctgaaagac ttcaccgtat ctggcaacct gctgtttatc   480
cgtctgaccg cagcggacca ccgccaatta caattatcta tcagctcttg tttacaacaa   540
ctgtcgctgt taatgtggat cactcaatgt ttcctgccag tattcctggc tcaggccccg   600
agcggtcagc gtcgtcacca ccaccaccac cactaa                              636
```

<210> SEQ ID NO 10
<211> LENGTH: 966
<212> TYPE: DNA
<213> ORGANISM: Artificial Sequence
<220> FEATURE:
<223> OTHER INFORMATION: NY-ESO-1/LAGE construct

<400> SEQUENCE: 10

```
atggatccaa gcagccattc atcaaatatg gcgaataccc aaatgaaatc agacaaaatc    60
attattgctc accgtggtgc tagcggttat ttaccagagc atacgttaga atctaaagca   120
cttgcgtttg cacaacaggc tgattattta gagcaagatt tagcaatgac taaggatggt   180
cgtttagtgg ttattcacga tcactttttta gatggcttga ctgatgttgc gaaaaaattc   240
ccacatcgtc atcgtaaaga tggccgttac tatgtcatcg actttacctt aaaagaaatt   300
caaagtttag aaatgacaga aactttgaa accggtgcgc gtggtccgga aagccgtctg   360
ctggaatttt atctggccat gccgtttgcg accccgatgg aagcggaact ggcccgtcgt   420
```

```
agcctggctc aagatgcacc gccgctgccg gttccgggcg tgctgctgaa agaatttacc    480
gtgagcggca acattctgac cattcgtctg acggcggcag accatcgtca gctgcaactg    540
agcattagca gctgcctgca acagctgtct ctgctgatgt ggattaccca gtgctttctg    600
ccggtgtttc tggcccagcc gccgtctggt caacgtggtg cgcgcgtcg tccggattct      660
cgcctgctgg aactgcatat accatgccg ttcagctctc caatggaggc cgaattagtg    720
cgtcgcattc tgagccgtga tgcggcaccg ctgccgcgtc aggtgcggt tctgaaagac    780
ttcaccgtat ctggcaacct gctgtttatc cgtctgaccg cagcggacca ccgccaatta    840
caattatcta tcagctcttg tttacaacaa ctgtcgctgt taatgtggat cactcaatgt    900
ttcctgccag tattcctggc tcaggccccg agcggtcagc gtcgtcacca ccaccaccac    960
cactaa                                                                  966

<210> SEQ ID NO 11
<211> LENGTH: 211
<212> TYPE: PRT
<213> ORGANISM: Artificial Sequence
<220> FEATURE:
<223> OTHER INFORMATION: NY-ESO-1/LAGE construct

<400> SEQUENCE: 11

Met Gly Ala Arg Gly Pro Glu Ser Arg Leu Leu Glu Phe Tyr Leu Ala
  1               5                  10                  15

Met Pro Phe Ala Thr Pro Met Glu Ala Glu Leu Ala Arg Arg Ser Leu
                 20                  25                  30

Ala Gln Asp Ala Pro Pro Leu Pro Val Pro Gly Val Leu Leu Lys Glu
             35                  40                  45

Phe Thr Val Ser Gly Asn Ile Leu Thr Ile Arg Leu Thr Ala Ala Asp
         50                  55                  60

His Arg Gln Leu Gln Leu Ser Ile Ser Ser Cys Leu Gln Gln Leu Ser
 65                  70                  75                  80

Leu Leu Met Trp Ile Thr Gln Cys Phe Leu Pro Val Phe Leu Ala Gln
                 85                  90                  95

Pro Pro Ser Gly Gln Arg Gly Ala Arg Arg Pro Ser Arg Leu
            100                 105                 110

Leu Glu Leu His Ile Thr Met Pro Phe Ser Ser Pro Met Glu Ala Glu
        115                 120                 125

Leu Val Arg Arg Ile Leu Ser Arg Asp Ala Ala Pro Leu Pro Arg Pro
    130                 135                 140

Gly Ala Val Leu Lys Asp Phe Thr Val Ser Gly Asn Leu Leu Phe Ile
145                 150                 155                 160

Arg Leu Thr Ala Ala Asp His Arg Gln Leu Gln Leu Ser Ile Ser Ser
                165                 170                 175

Cys Leu Gln Gln Leu Ser Leu Leu Met Trp Ile Thr Gln Cys Phe Leu
            180                 185                 190

Pro Val Phe Leu Ala Gln Ala Pro Ser Gly Gln Arg Arg His His His
        195                 200                 205

His His His
    210

<210> SEQ ID NO 12
<211> LENGTH: 321
<212> TYPE: PRT
<213> ORGANISM: Artificial Sequence
<220> FEATURE:
<223> OTHER INFORMATION: NY-ESO-1/LAGE construct
```

<400> SEQUENCE: 12

```
Met Asp Pro Ser Ser His Ser Ser Asn Met Ala Asn Thr Gln Met Lys
 1               5                  10                  15

Ser Asp Lys Ile Ile Ile Ala His Arg Gly Ala Ser Gly Tyr Leu Pro
             20                  25                  30

Glu His Thr Leu Glu Ser Lys Ala Leu Ala Phe Ala Gln Gln Ala Asp
         35                  40                  45

Tyr Leu Glu Gln Asp Leu Ala Met Thr Lys Asp Gly Arg Leu Val Val
 50                  55                  60

Ile His Asp His Phe Leu Asp Gly Leu Thr Asp Val Ala Lys Lys Phe
 65                  70                  75                  80

Pro His Arg His Arg Lys Asp Gly Arg Tyr Tyr Val Ile Asp Phe Thr
                 85                  90                  95

Leu Lys Glu Ile Gln Ser Leu Glu Met Thr Glu Asn Phe Glu Thr Gly
            100                 105                 110

Ala Arg Gly Pro Glu Ser Arg Leu Leu Glu Phe Tyr Leu Ala Met Pro
        115                 120                 125

Phe Ala Thr Pro Met Glu Ala Glu Leu Ala Arg Arg Ser Leu Ala Gln
130                 135                 140

Asp Ala Pro Pro Leu Pro Val Pro Gly Val Leu Leu Lys Glu Phe Thr
145                 150                 155                 160

Val Ser Gly Asn Ile Leu Thr Ile Arg Leu Thr Ala Ala Asp His Arg
                165                 170                 175

Gln Leu Gln Leu Ser Ile Ser Ser Cys Leu Gln Gln Leu Ser Leu Leu
            180                 185                 190

Met Trp Ile Thr Gln Cys Phe Leu Pro Val Phe Leu Ala Gln Pro Pro
        195                 200                 205

Ser Gly Gln Arg Gly Gly Ala Arg Arg Pro Asp Ser Arg Leu Leu Glu
210                 215                 220

Leu His Ile Thr Met Pro Phe Ser Ser Pro Met Glu Ala Glu Leu Val
225                 230                 235                 240

Arg Arg Ile Leu Ser Arg Asp Ala Ala Pro Leu Pro Arg Pro Gly Ala
                245                 250                 255

Val Leu Lys Asp Phe Thr Val Ser Gly Asn Leu Leu Phe Ile Arg Leu
            260                 265                 270

Thr Ala Ala Asp His Arg Gln Leu Gln Leu Ser Ile Ser Ser Cys Leu
        275                 280                 285

Gln Gln Leu Ser Leu Leu Met Trp Ile Thr Gln Cys Phe Leu Pro Val
290                 295                 300

Phe Leu Ala Gln Ala Pro Ser Gly Gln Arg Arg His His His His His
305                 310                 315                 320

His
```

<210> SEQ ID NO 13
<211> LENGTH: 870
<212> TYPE: DNA
<213> ORGANISM: Artificial Sequence
<220> FEATURE:
<223> OTHER INFORMATION: NY-ESO-1/LAGE construct

<400> SEQUENCE: 13

```
atgcaggcgg aaggccgtgg tactggcggt agcaccggcg atgcagatgg tccgggcggt      60
ccgggtattc cggatggtcc gggtggtaat gcaggtggtc caggtgaagc aggtgcgact     120
ggcggtcgtg gtccacgcgg tgcaggtgca gcgcgtgcat ctggtccagg tggcggtgcg     180
```

| | | |
|---|---|---|
| ccgcgtggcc cgcatggtgg tgcagctagt gcgcaagatg gtcgttgccc gtgtggtgcg | 240 | |
| cgtcgtccgg atagccgtct gctggagctg catattacca tgccgtttag cagcccaatg | 300 | |
| gaagctgagc tggtgcgtcg tattctgtct cgtgacgcag caccgctgcc acgtccgggt | 360 | |
| gcggttctga aagatttac cgtgagcggc aacctgctgt ttattcgtct gaccgcggca | 420 | |
| gatcatcgtc agctgcaact gagcattagc agctgcctgc aacagctgtc tctgctgatg | 480 | |
| tggattaccc agtgctttct gccggtgttt ctggctcagg cgccgtctgg tcagcgtcgt | 540 | |
| ggtggtgccc gtggcccgga atctcgtctg ctggaatttt atctggccat gccgttcgcg | 600 | |
| acgccgatgg aagcagagct ggcccgtcgc agcctggctc aggatgcacc gccgctgccg | 660 | |
| gttccgggcg tgctgctgaa agaatttacg gttagcggta acattctgac catccgtctg | 720 | |
| accgcagcgg accaccgcca actgcaactg tctatcagct cttgcctgca acaactgtcg | 780 | |
| ttattaatgt ggatcactca atgttttta ccagtattcc tggcccaacc gccgagcggc | 840 | |
| caacgtcgtc accaccacca ccaccactaa | 870 | |

<210> SEQ ID NO 14
<211> LENGTH: 1200
<212> TYPE: DNA
<213> ORGANISM: Artificial Sequence
<220> FEATURE:
<223> OTHER INFORMATION: NY-ESO-1/LAGE construct

<400> SEQUENCE: 14

| | | |
|---|---|---|
| atggatccaa gcagccattc atcaaatatg gcgaataccc aaatgaaatc agacaaaatc | 60 | |
| attattgctc accgtggtgc tagcggttat ttaccagagc atacgttaga atctaaagca | 120 | |
| cttgcgtttg cacaacaggc tgattattta gagcaagatt tagcaatgac taaggatggt | 180 | |
| cgtttagtgg ttattcacga tcactttta gatggcttga ctgatgttgc gaaaaaattc | 240 | |
| ccacatcgtc atcgtaaaga tggccgttac tatgtcatcg actttacctt aaaagaaatt | 300 | |
| caaagtttag aaatgacaga aactttgaa acccaggcgg aaggccgtgg tactggcggt | 360 | |
| agcaccggcg atgcagatgg tccgggcggt ccgggtattc cggatggtcc gggtggtaat | 420 | |
| gcaggtggtc aggtgaagc aggtgcgact ggcggtcgtg gtccacgcgg tgcaggtgca | 480 | |
| gcgcgtgcat ctggtccagg tggcggtgcg ccgcgtggcc cgcatggtgg tgcagctagt | 540 | |
| gcgcaagatg gtcgttgccc gtgtggtgcg cgtcgtccgg atagccgtct gctggagctg | 600 | |
| catattacca tgccgtttag cagcccaatg gaagctgagc tggtgcgtcg tattctgtct | 660 | |
| cgtgacgcag caccgctgcc acgtccgggt gcggttctga aagatttac cgtgagcggc | 720 | |
| aacctgctgt ttattcgtct gaccgcggca gatcatcgtc agctgcaact gagcattagc | 780 | |
| agctgcctgc aacagctgtc tctgctgatg tggattaccc agtgctttct gccggtgttt | 840 | |
| ctggctcagg cgccgtctgg tcagcgtcgt ggtggtgccc gtggcccgga atctcgtctg | 900 | |
| ctggaatttt atctggccat gccgttcgcg acgccgatgg aagcagagct ggcccgtcgc | 960 | |
| agcctggctc aggatgcacc gccgctgccg gttccgggcg tgctgctgaa agaatttacg | 1020 | |
| gttagcggta acattctgac catccgtctg accgcagcgg accaccgcca actgcaactg | 1080 | |
| tctatcagct cttgcctgca acaactgtcg ttattaatgt ggatcactca atgttttta | 1140 | |
| ccagtattcc tggcccaacc gccgagcggc caacgtcgtc accaccacca ccaccactaa | 1200 | |

<210> SEQ ID NO 15
<211> LENGTH: 289
<212> TYPE: PRT
<213> ORGANISM: Artificial Sequence
<220> FEATURE:

<223> OTHER INFORMATION: NY-ESO-1/LAGE construct

<400> SEQUENCE: 15

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Ala Gln Asp Gly Arg Cys Pro Cys Gly Ala
65                  70                  75                  80

Arg Arg Pro Asp Ser Arg Leu Leu Glu Leu His Ile Thr Met Pro Phe
                85                  90                  95

Ser Ser Pro Met Glu Ala Glu Leu Val Arg Arg Ile Leu Ser Arg Asp
            100                 105                 110

Ala Ala Pro Leu Pro Arg Pro Gly Ala Val Leu Lys Asp Phe Thr Val
        115                 120                 125

Ser Gly Asn Leu Leu Phe Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Ala Pro Ser
                165                 170                 175

Gly Gln Arg Arg Gly Gly Ala Arg Gly Pro Glu Ser Arg Leu Leu Glu
            180                 185                 190

Phe Tyr Leu Ala Met Pro Phe Ala Thr Pro Met Glu Ala Glu Leu Ala
        195                 200                 205

Arg Arg Ser Leu Ala Gln Asp Ala Pro Pro Leu Pro Val Pro Gly Val
    210                 215                 220

Leu Leu Lys Glu Phe Thr Val Ser Gly Asn Ile Leu Thr Ile Arg Leu
225                 230                 235                 240

Thr Ala Ala Asp His Arg Gln Leu Gln Leu Ser Ile Ser Ser Cys Leu
                245                 250                 255

Gln Gln Leu Ser Leu Leu Met Trp Ile Thr Gln Cys Phe Leu Pro Val
            260                 265                 270

Phe Leu Ala Gln Pro Pro Ser Gly Gln Arg Arg His His His His His
        275                 280                 285

His

<210> SEQ ID NO 16
<211> LENGTH: 399
<212> TYPE: PRT
<213> ORGANISM: Artificial Sequence
<220> FEATURE:
<223> OTHER INFORMATION: NY-ESO-1/LAGE construct

<400> SEQUENCE: 16

Met Asp Pro Ser Ser His Ser Ser Asn Met Ala Asn Thr Gln Met Lys
1               5                   10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val

|    |    |    |    | 50  |    |    |    |    | 55  |    |    |    |    | 60  |    |    |
|----|----|----|----|-----|----|----|----|----|-----|----|----|----|----|-----|----|----|

Ile His Asp His Phe Leu Asp Gly Leu Thr Asp Val Ala Lys Lys Phe
65                  70                      75                  80

Pro His Arg His Arg Lys Asp Gly Arg Tyr Tyr Val Ile Asp Phe Thr
                    85                      90                  95

Leu Lys Glu Ile Gln Ser Leu Glu Met Thr Glu Asn Phe Glu Thr Gln
            100                 105                 110

Ala Glu Gly Arg Gly Thr Gly Gly Ser Thr Gly Asp Ala Asp Gly Pro
                115                 120                 125

Gly Gly Pro Gly Ile Pro Asp Gly Pro Gly Gly Asn Ala Gly Gly Pro
130                 135                     140

Gly Glu Ala Gly Ala Thr Gly Gly Arg Gly Pro Arg Gly Ala Gly Ala
145                 150                 155                 160

Ala Arg Ala Ser Gly Pro Gly Gly Gly Ala Pro Arg Gly Pro His Gly
                165                 170                 175

Gly Ala Ala Ser Ala Gln Asp Gly Arg Cys Pro Cys Gly Ala Arg Arg
                180                 185                 190

Pro Asp Ser Arg Leu Leu Glu Leu His Ile Thr Met Pro Phe Ser Ser
                195                 200                 205

Pro Met Glu Ala Glu Leu Val Arg Arg Ile Leu Ser Arg Asp Ala Ala
210                 215                     220

Pro Leu Pro Arg Pro Gly Ala Val Leu Lys Asp Phe Thr Val Ser Gly
225                 230                 235                 240

Asn Leu Leu Phe Ile Arg Leu Thr Ala Ala Asp His Arg Gln Leu Gln
                245                 250                 255

Leu Ser Ile Ser Ser Cys Leu Gln Gln Leu Ser Leu Leu Met Trp Ile
                260                 265                 270

Thr Gln Cys Phe Leu Pro Val Phe Leu Ala Gln Ala Pro Ser Gly Gln
                275                 280                 285

Arg Arg Gly Gly Ala Arg Gly Pro Glu Ser Arg Leu Leu Glu Phe Tyr
290                 295                     300

Leu Ala Met Pro Phe Ala Thr Pro Met Glu Ala Glu Leu Ala Arg Arg
305                 310                 315                 320

Ser Leu Ala Gln Asp Ala Pro Pro Leu Pro Val Pro Gly Val Leu Leu
                325                 330                 335

Lys Glu Phe Thr Val Ser Gly Asn Ile Leu Thr Ile Arg Leu Thr Ala
                340                 345                 350

Ala Asp His Arg Gln Leu Gln Leu Ser Ile Ser Ser Cys Leu Gln Gln
                355                 360                 365

Leu Ser Leu Leu Met Trp Ile Thr Gln Cys Phe Leu Pro Val Phe Leu
370                 375                 380

Ala Gln Pro Pro Ser Gly Gln Arg Arg His His His His His
385                 390                 395

<210> SEQ ID NO 17
<211> LENGTH: 732
<212> TYPE: DNA
<213> ORGANISM: Artificial Sequence
<220> FEATURE:
<223> OTHER INFORMATION: NY-ESO-1/LAGE construct

<400> SEQUENCE: 17
atggcaggtg cagcgcgtgc atctggtcca ggtggcggtg cgccgcgtgg cccgcatggt      60
ggtgcagcta gtgcgcaaga tggtcgttgc ccgtgtggtg cgcgtcgtcc ggatagccgt     120
ctgctggagc tgcatattac catgccgttt agcagcccaa tggaagctga gctggtgcgt     180

```
cgtattctgt ctcgtgacgc agcaccgctg ccacgtccgg gtgcggttct gaaagatttt    240
accgtgagcg gcaacctgct gtttattcgt ctgaccgcgg cagatcatcg tcagctgcaa    300
ctgagcatta gcagctgcct gcaacagctg tctctgctga tgtggattac ccagtgcttt    360
ctgccggtgt ttctggctca ggcgccgtct ggtcagcgtc gtggtggtgc ccgtggcccg    420
gaatctcgtc tgctggaatt ttatctggcc atgccgttcg cgacgccgat ggaagcagag    480
ctggcccgtc gcagcctggc tcaggatgca ccgccgctgc cggttccggg cgtgctgctg    540
aaagaattta cggttagcgg taacattctg accatccgtc tgaccgcagc ggaccaccgc    600
caactgcaac tgtctatcag ctcttgcctg caacaactgt cgttattaat gtggatcact    660
caatgttttt taccagtatt cctggcccaa ccgccgagcg ccaacgtcg tcaccaccac    720 caccaccact aa                                                        732
```

<210> SEQ ID NO 18
<211> LENGTH: 1062
<212> TYPE: DNA
<213> ORGANISM: Artificial Sequence
<220> FEATURE:
<223> OTHER INFORMATION: NY-ESO-1/LAGE construct

<400> SEQUENCE: 18

```
atggatccaa gcagccattc atcaaatatg gcgaataccc aaatgaaatc agacaaaatc     60
attattgctc accgtggtgc tagcggttat ttaccagagc atacgttaga atctaaagca    120
cttgcgtttg cacaacaggc tgattattta gagcaagatt tagcaatgac taaggatggt    180
cgtttagtgg ttattcacga tcactttta gatggcttga ctgatgttgc gaaaaaattc    240
ccacatcgtc atcgtaaaga tggccgttac tatgtcatcg actttacctt aaaagaaatt    300
caaagtttag aaatgacaga aaactttgaa accgcaggtg cagcgcgtgc atctggtcca    360
ggtggcggtg cgccgcgtgg cccgcatggt ggtgcagcta gtgcgcaaga tggtcgttgc    420
ccgtgtggtg cgcgtcgtcc ggatagccgt ctgctggagc tgcatattac catgccgttt    480
agcagcccaa tggaagctga gctggtgcgt cgtattctgt ctcgtgacgc agcaccgctg    540
ccacgtccgg gtgcggttct gaaagatttt accgtgagcg gcaacctgct gtttattcgt    600
ctgaccgcgg cagatcatcg tcagctgcaa ctgagcatta gcagctgcct gcaacagctg    660
tctctgctga tgtggattac ccagtgcttt ctgccggtgt ttctggctca ggcgccgtct    720
ggtcagcgtc gtggtggtgc ccgtggcccg gaatctcgtc tgctggaatt ttatctggcc    780
atgccgttcg cgacgccgat ggaagcagag ctggcccgtc gcagcctggc tcaggatgca    840
ccgccgctgc cggttccggg cgtgctgctg aaagaattta cggttagcgg taacattctg    900
accatccgtc tgaccgcagc ggaccaccgc caactgcaac tgtctatcag ctcttgcctg    960
caacaactgt cgttattaat gtggatcact caatgttttt taccagtatt cctggcccaa   1020
ccgccgagcg ccaacgtcg tcaccaccac caccaccact aa                       1062
```

<210> SEQ ID NO 19
<211> LENGTH: 243
<212> TYPE: PRT
<213> ORGANISM: Artificial Sequence
<220> FEATURE:
<223> OTHER INFORMATION: NY-ESO-1/LAGE construct

<400> SEQUENCE: 19

Met Ala Gly Ala Ala Arg Ala Ser Gly Pro Gly Gly Gly Ala Pro Arg
1               5                   10                  15

```
Gly Pro His Gly Gly Ala Ala Ser Ala Gln Asp Gly Arg Cys Pro Cys
            20                  25                  30
Gly Ala Arg Arg Pro Asp Ser Arg Leu Leu Glu Leu His Ile Thr Met
            35                  40                  45
Pro Phe Ser Ser Pro Met Glu Ala Glu Leu Val Arg Arg Ile Leu Ser
50                  55                  60
Arg Asp Ala Ala Pro Leu Pro Arg Pro Gly Ala Val Leu Lys Asp Phe
65                  70                  75                  80
Thr Val Ser Gly Asn Leu Leu Phe Ile Arg Leu Thr Ala Ala Asp His
                85                  90                  95
Arg Gln Leu Gln Leu Ser Ile Ser Cys Leu Gln Gln Leu Ser Leu
            100                 105                 110
Leu Met Trp Ile Thr Gln Cys Phe Leu Pro Val Phe Leu Ala Gln Ala
            115                 120                 125
Pro Ser Gly Gln Arg Arg Gly Gly Ala Arg Gly Pro Glu Ser Arg Leu
130                 135                 140
Leu Glu Phe Tyr Leu Ala Met Pro Phe Ala Thr Pro Met Glu Ala Glu
145                 150                 155                 160
Leu Ala Arg Arg Ser Leu Ala Gln Asp Ala Pro Pro Leu Pro Val Pro
                165                 170                 175
Gly Val Leu Leu Lys Glu Phe Thr Val Ser Gly Asn Ile Leu Thr Ile
            180                 185                 190
Arg Leu Thr Ala Ala Asp His Arg Gln Leu Gln Leu Ser Ile Ser Ser
            195                 200                 205
Cys Leu Gln Gln Leu Ser Leu Leu Met Trp Ile Thr Gln Cys Phe Leu
210                 215                 220
Pro Val Phe Leu Ala Gln Pro Pro Ser Gly Gln Arg Arg His His His
225                 230                 235                 240
His His His
```

<210> SEQ ID NO 20
<211> LENGTH: 353
<212> TYPE: PRT
<213> ORGANISM: Artificial Sequence
<220> FEATURE:
<223> OTHER INFORMATION: NY-ESO-1/LAGE construct

<400> SEQUENCE: 20

```
Met Asp Pro Ser Ser His Ser Ser Asn Met Ala Asn Thr Gln Met Lys
1               5                   10                  15
Ser Asp Lys Ile Ile Ile Ala His Arg Gly Ala Ser Gly Tyr Leu Pro
            20                  25                  30
Glu His Thr Leu Glu Ser Lys Ala Leu Ala Phe Ala Gln Gln Ala Asp
            35                  40                  45
Tyr Leu Glu Gln Asp Leu Ala Met Thr Lys Asp Gly Arg Leu Val Val
50                  55                  60
Ile His Asp His Phe Leu Asp Gly Leu Thr Asp Val Ala Lys Lys Phe
65                  70                  75                  80
Pro His Arg His Arg Lys Asp Gly Arg Tyr Tyr Val Ile Asp Phe Thr
                85                  90                  95
Leu Lys Glu Ile Gln Ser Leu Glu Met Thr Glu Asn Phe Glu Thr Ala
            100                 105                 110
Gly Ala Ala Arg Ala Ser Gly Pro Gly Gly Gly Ala Pro Arg Gly Pro
            115                 120                 125
His Gly Gly Ala Ala Ser Ala Gln Asp Gly Arg Cys Pro Cys Gly Ala
130                 135                 140
```

Arg Arg Pro Asp Ser Arg Leu Leu Glu Leu His Ile Thr Met Pro Phe
145                 150                 155                 160

Ser Ser Pro Met Glu Ala Glu Leu Val Arg Arg Ile Leu Ser Arg Asp
            165                 170                 175

Ala Ala Pro Leu Pro Arg Pro Gly Ala Val Leu Lys Asp Phe Thr Val
            180                 185                 190

Ser Gly Asn Leu Leu Phe Ile Arg Leu Thr Ala Ala Asp His Arg Gln
            195                 200                 205

Leu Gln Leu Ser Ile Ser Ser Cys Leu Gln Gln Leu Ser Leu Leu Met
        210                 215                 220

Trp Ile Thr Gln Cys Phe Leu Pro Val Phe Leu Ala Gln Ala Pro Ser
225                 230                 235                 240

Gly Gln Arg Arg Gly Gly Ala Arg Gly Pro Glu Ser Arg Leu Leu Glu
                245                 250                 255

Phe Tyr Leu Ala Met Pro Phe Ala Thr Pro Met Glu Ala Glu Leu Ala
                260                 265                 270

Arg Arg Ser Leu Ala Gln Asp Ala Pro Pro Leu Pro Val Pro Gly Val
            275                 280                 285

Leu Leu Lys Glu Phe Thr Val Ser Gly Asn Ile Leu Thr Ile Arg Leu
        290                 295                 300

Thr Ala Ala Asp His Arg Gln Leu Gln Leu Ser Ile Ser Ser Cys Leu
305                 310                 315                 320

Gln Gln Leu Ser Leu Leu Met Trp Ile Thr Gln Cys Phe Leu Pro Val
                325                 330                 335

Phe Leu Ala Gln Pro Pro Ser Gly Gln Arg Arg His His His His
                340                 345                 350

His

<210> SEQ ID NO 21
<211> LENGTH: 639
<212> TYPE: DNA
<213> ORGANISM: Artificial Sequence
<220> FEATURE:
<223> OTHER INFORMATION: NY-ESO-1/LAGE construct

<400> SEQUENCE: 21
atgggtgcgc gtcgtccgga tagccgtctg ctggagctgc atattaccat gccgtttagc      60
agcccaatgg aagctgagct ggtgcgtcgt attctgtctc gtgacgcagc accgctgcca     120
cgtccgggtg cggttctgaa agattttacc gtgagcggca acctgctgtt tattcgtctg     180
accgcggcag atcatcgtca gctgcaactg agcattagca gctgcctgca acagctgtct     240
ctgctgatgt ggattaccca gtgctttctg ccggtgtttc tggctcaggc gccgtctggt     300
cagcgtcgtg gtggtgcccg tggcccggaa tctcgtctgc tggaattta tctggccatg     360 ccgttcgcga cgccgatgga agcagagctg gcccgtcgca gctggctca ggatgcaccg     420 ccgctgccgg ttccgggcgt gctgctgaaa gaatttacgg ttagcggtaa cattctgacc     480
atccgtctga ccgcagcgga ccaccgccaa ctgcaactgt ctatcagctc ttgcctgcaa     540
caactgtcgt tattaatgtg gatcactcaa tgttttttac agtattcct ggcccaaccg      600 ccgagcggcc aacgtcgtca ccaccaccac caccactaa                              639

<210> SEQ ID NO 22
<211> LENGTH: 969
<212> TYPE: DNA
<213> ORGANISM: Artificial Sequence
<220> FEATURE:

<223> OTHER INFORMATION: NY-ESO-1/LAGE construct

<400> SEQUENCE: 22

```
atggatccaa gcagccattc atcaaatatg gcgaataccc aaatgaaatc agacaaaatc      60
attattgctc accgtggtgc tagcggttat ttaccagagc atacgttaga atctaaagca     120
cttgcgtttg cacaacaggc tgattattta gagcaagatt tagcaatgac taaggatggt     180
cgttagtgg ttattcacga tcactttta gatggcttga ctgatgttgc gaaaaaattc       240
ccacatcgtc atcgtaaaga tggccgttac tatgtcatcg actttacctt aaaagaaatt     300
caaagtttag aaatgacaga aactttgaa accggtgcgc gtcgtccgga tagccgtctg      360
ctggagctgc atattaccat gccgtttagc agcccaatgg aagctgagct ggtgcgtcgt     420
attctgtctc gtgacgcagc accgctgcca cgtccgggtg cggttctgaa agattttacc     480
gtgagcggca acctgctgtt tattcgtctg accgcggcag atcatcgtca gctgcaactg     540
agcattagca gctgcctgca acagctgtct ctgctgatgt ggattaccca gtgctttctg     600
ccggtgtttc tggctcaggc gccgtctggt cagcgtcgtg gtggtgcccg tggcccggaa     660
tctcgtctgc tggaattta tctggccatg ccgttcgcga cgccgatgga agcagagctg      720
gcccgtcgca gcctggctca ggatgcaccg ccgctgccgg ttccgggcgt gctgctgaaa     780
gaatttacgg ttagcggtaa cattctgacc atccgtctga ccgcagcgga ccaccgccaa     840
ctgcaactgt ctatcagctc ttgcctgcaa caactgtcgt tattaatgtg gatcactcaa     900
tgttttttac cagtattcct ggcccaaccg ccgagcggcc aacgtcgtca ccaccaccac     960
caccactaa                                                             969
```

<210> SEQ ID NO 23
<211> LENGTH: 212
<212> TYPE: PRT
<213> ORGANISM: Artificial Sequence
<220> FEATURE:
<223> OTHER INFORMATION: NY-ESO-1/LAGE construct

<400> SEQUENCE: 23

```
Met Gly Ala Arg Arg Pro Asp Ser Arg Leu Leu Glu Leu His Ile Thr
 1               5                  10                  15
Met Pro Phe Ser Ser Pro Met Glu Ala Glu Leu Val Arg Arg Ile Leu
                20                  25                  30
Ser Arg Asp Ala Ala Pro Leu Pro Arg Pro Gly Ala Val Leu Lys Asp
            35                  40                  45
Phe Thr Val Ser Gly Asn Leu Leu Phe Ile Arg Leu Thr Ala Ala Asp
        50                  55                  60
His Arg Gln Leu Gln Leu Ser Ile Ser Ser Cys Leu Gln Gln Leu Ser
 65                  70                  75                  80
Leu Leu Met Trp Ile Thr Gln Cys Phe Leu Pro Val Phe Leu Ala Gln
                85                  90                  95
Ala Pro Ser Gly Gln Arg Arg Gly Gly Ala Arg Gly Pro Glu Ser Arg
                100                 105                 110
Leu Leu Glu Phe Tyr Leu Ala Met Pro Phe Ala Thr Pro Met Glu Ala
            115                 120                 125
Glu Leu Ala Arg Arg Ser Leu Ala Gln Asp Ala Pro Pro Leu Pro Val
        130                 135                 140
Pro Gly Val Leu Leu Lys Glu Phe Thr Val Ser Gly Asn Ile Leu Thr
145                 150                 155                 160
Ile Arg Leu Thr Ala Ala Asp His Arg Gln Leu Gln Leu Ser Ile Ser
                165                 170                 175
```

```
Ser Cys Leu Gln Gln Leu Ser Leu Leu Met Trp Ile Thr Gln Cys Phe
            180                 185                 190

Leu Pro Val Phe Leu Ala Gln Pro Pro Ser Gly Gln Arg Arg His His
        195                 200                 205

His His His His
    210

<210> SEQ ID NO 24
<211> LENGTH: 322
<212> TYPE: PRT
<213> ORGANISM: Artificial Sequence
<220> FEATURE:
<223> OTHER INFORMATION: NY-ESO-1/LAGE construct

<400> SEQUENCE: 24

Met Asp Pro Ser Ser His Ser Ser Asn Met Ala Asn Thr Gln Met Lys
  1               5                  10                  15

Ser Asp Lys Ile Ile Ile Ala His Arg Gly Ala Ser Gly Tyr Leu Pro
             20                  25                  30

Glu His Thr Leu Glu Ser Lys Ala Leu Ala Phe Ala Gln Gln Ala Asp
         35                  40                  45

Tyr Leu Glu Gln Asp Leu Ala Met Thr Lys Asp Gly Arg Leu Val Val
     50                  55                  60

Ile His Asp His Phe Leu Asp Gly Leu Thr Asp Val Ala Lys Lys Phe
 65                  70                  75                  80

Pro His Arg His Arg Lys Asp Gly Arg Tyr Tyr Val Ile Asp Phe Thr
                 85                  90                  95

Leu Lys Glu Ile Gln Ser Leu Glu Met Thr Glu Asn Phe Glu Thr Gly
            100                 105                 110

Ala Arg Arg Pro Asp Ser Arg Leu Leu Glu Leu His Ile Thr Met Pro
        115                 120                 125

Phe Ser Ser Pro Met Glu Ala Glu Leu Val Arg Arg Ile Leu Ser Arg
    130                 135                 140

Asp Ala Ala Pro Leu Pro Arg Pro Gly Ala Val Leu Lys Asp Phe Thr
145                 150                 155                 160

Val Ser Gly Asn Leu Leu Phe Ile Arg Leu Thr Ala Ala Asp His Arg
                165                 170                 175

Gln Leu Gln Leu Ser Ile Ser Ser Cys Leu Gln Gln Leu Ser Leu Leu
            180                 185                 190

Met Trp Ile Thr Gln Cys Phe Leu Pro Val Phe Leu Ala Gln Ala Pro
        195                 200                 205

Ser Gly Gln Arg Arg Gly Gly Ala Arg Gly Pro Glu Ser Arg Leu Leu
    210                 215                 220

Glu Phe Tyr Leu Ala Met Pro Phe Ala Thr Pro Met Glu Ala Glu Leu
225                 230                 235                 240

Ala Arg Arg Ser Leu Ala Gln Asp Ala Pro Leu Pro Val Pro Gly
                245                 250                 255

Val Leu Leu Lys Glu Phe Thr Val Ser Gly Asn Ile Leu Thr Ile Arg
            260                 265                 270

Leu Thr Ala Ala Asp His Arg Gln Leu Gln Leu Ser Ile Ser Ser Cys
        275                 280                 285

Leu Gln Gln Leu Ser Leu Leu Met Trp Ile Thr Gln Cys Phe Leu Pro
    290                 295                 300

Val Phe Leu Ala Gln Pro Pro Ser Gly Gln Arg Arg His His His His
305                 310                 315                 320
```

His His

<210> SEQ ID NO 25
<211> LENGTH: 687
<212> TYPE: DNA
<213> ORGANISM: Artificial Sequence
<220> FEATURE:
<223> OTHER INFORMATION: NY-ESO-1/LAGE construct

<400> SEQUENCE: 25

```
atgggccatc atcatcatca tcatcatcat catcacagca gcggccatat cgacgacgac    60
gacaagcata tgggtgcgcg tggtccggaa agccgtctgc tggaatttta tctggccatg   120
ccgtttgcga ccccgatgga agcggaactg gcccgtcgta gcctggctca agatgcaccg   180
ccgctgccgg ttccgggcgt gctgctgaaa gaatttaccg tgagcggcaa cattctgacc   240
attcgtctga cggcggcaga ccatcgtcag ctgcaactga gcattagcag ctgcctgcaa   300
cagctgtctc tgctgatgtg gattacccag tgctttctgc cggtgtttct ggcccagccg   360
ccgtctggtc aacgtggtgg cgcgcgtcgt ccggattctc gcctgctgga actgcatatt   420
accatgccgt tcagctctcc aatggaggcc gaattagtgc gtcgcattct gagccgtgat   480
gcggcaccgc tgccgcgtcc aggtgcggtt ctgaaagact tcaccgtatc tggcaacctg   540
ctgtttatcc gtctgaccgc agcggaccac cgccaattac aattatctat cagctcttgt   600
ttacaacaac tgtcgctgtt aatgtggatc actcaatgtt tcctgccagt attcctggct   660
caggccccga gcggtcagcg tcgttaa                                       687
```

<210> SEQ ID NO 26
<211> LENGTH: 228
<212> TYPE: PRT
<213> ORGANISM: Artificial Sequence
<220> FEATURE:
<223> OTHER INFORMATION: NY-ESO-1/LAGE construct

<400> SEQUENCE: 26

```
Met Gly His His His His His His His His Ser Ser Gly His
  1               5                  10                  15

Ile Asp Asp Asp Asp Lys His Met Gly Ala Arg Gly Pro Glu Ser Arg
                 20                  25                  30

Leu Leu Glu Phe Tyr Leu Ala Met Pro Phe Ala Thr Pro Met Glu Ala
             35                  40                  45

Glu Leu Ala Arg Arg Ser Leu Ala Gln Asp Ala Pro Pro Leu Pro Val
         50                  55                  60

Pro Gly Val Leu Leu Lys Glu Phe Thr Val Ser Gly Asn Ile Leu Thr
 65                  70                  75                  80

Ile Arg Leu Thr Ala Ala Asp His Arg Gln Leu Gln Leu Ser Ile Ser
                 85                  90                  95

Ser Cys Leu Gln Gln Leu Ser Leu Leu Met Trp Ile Thr Gln Cys Phe
            100                 105                 110

Leu Pro Val Phe Leu Ala Gln Pro Pro Ser Gly Gln Arg Gly Gly Ala
            115                 120                 125

Arg Arg Pro Asp Ser Arg Leu Leu Glu Leu His Ile Thr Met Pro Phe
        130                 135                 140

Ser Ser Pro Met Glu Ala Glu Leu Val Arg Arg Ile Leu Ser Arg Asp
145                 150                 155                 160

Ala Ala Pro Leu Pro Arg Pro Gly Ala Val Leu Lys Asp Phe Thr Val
                165                 170                 175

Ser Gly Asn Leu Leu Phe Ile Arg Leu Thr Ala Ala Asp His Arg Gln
```

```
                 180                 185                 190
Leu Gln Leu Ser Ile Ser Ser Cys Leu Gln Gln Leu Ser Leu Leu Met
            195                 200                 205

Trp Ile Thr Gln Cys Phe Leu Pro Val Phe Leu Ala Gln Ala Pro Ser
        210                 215                 220

Gly Gln Arg Arg
225

<210> SEQ ID NO 27
<211> LENGTH: 636
<212> TYPE: DNA
<213> ORGANISM: Artificial Sequence
<220> FEATURE:
<223> OTHER INFORMATION: NY-ESO-1/LAGE construct

<400> SEQUENCE: 27
atgcatcatc atcatcatca cggtgcgcgt ggtccggaaa gccgtctgct ggaattttat      60
ctggccatgc cgtttgcgac cccgatggaa gcggaactgg cccgtcgtag cctggctcaa    120
gatgcaccgc cgctgccggt tccgggcgtg ctgctgaaag aatttaccgt gagcggcaac    180
attctgacca ttcgtctgac ggcggcagac catcgtcagc tgcaactgag cattagcagc    240
tgcctgcaac agctgtctct gctgatgtgg attacccagt gctttctgcc ggtgtttctg    300
gcccagccgc cgtctggtca acgtggtggc gcgcgtcgtc cggattctcg cctgctggaa    360
ctgcatatta ccatgccgtt cagctctcca atggaggccg aattagtgcg tcgcattctg    420
agccgtgatg cggcaccgct gccgcgtcca ggtgcggttc tgaaagactt caccgtatct    480
ggcaacctgc tgtttatccg tctgaccgca gcggaccacc gccaattaca attatctatc    540
agctcttgtt tacaacaact gtcgctgtta atgtggatca ctcaatgttt cctgccagta    600
ttcctggctc aggccccgag cggtcagcgt cgttaa                              636

<210> SEQ ID NO 28
<211> LENGTH: 211
<212> TYPE: PRT
<213> ORGANISM: Artificial Sequence
<220> FEATURE:
<223> OTHER INFORMATION: NY-ESO-1/LAGE construct

<400> SEQUENCE: 28

Met His His His His His His Gly Ala Arg Gly Pro Glu Ser Arg Leu
  1               5                  10                  15

Leu Glu Phe Tyr Leu Ala Met Pro Phe Ala Thr Pro Met Glu Ala Glu
             20                  25                  30

Leu Ala Arg Arg Ser Leu Ala Gln Asp Ala Pro Pro Leu Pro Val Pro
         35                  40                  45

Gly Val Leu Leu Lys Glu Phe Thr Val Ser Gly Asn Ile Leu Thr Ile
     50                  55                  60

Arg Leu Thr Ala Ala Asp His Arg Gln Leu Gln Leu Ser Ile Ser Ser
 65                  70                  75                  80

Cys Leu Gln Gln Leu Ser Leu Leu Met Trp Ile Thr Gln Cys Phe Leu
                 85                  90                  95

Pro Val Phe Leu Ala Gln Pro Pro Ser Gly Gln Arg Gly Gly Ala Arg
            100                 105                 110

Arg Pro Asp Ser Arg Leu Leu Glu Leu His Ile Thr Met Pro Phe Ser
        115                 120                 125

Ser Pro Met Glu Ala Glu Leu Val Arg Arg Ile Leu Ser Arg Asp Ala
    130                 135                 140
```

```
Ala Pro Leu Pro Arg Pro Gly Ala Val Leu Lys Asp Phe Thr Val Ser
145                 150                 155                 160

Gly Asn Leu Leu Phe Ile Arg Leu Thr Ala Ala Asp His Arg Gln Leu
            165                 170                 175

Gln Leu Ser Ile Ser Ser Cys Leu Gln Gln Leu Ser Leu Leu Met Trp
        180                 185                 190

Ile Thr Gln Cys Phe Leu Pro Val Phe Leu Ala Gln Ala Pro Ser Gly
    195                 200                 205

Gln Arg Arg
    210
```

<210> SEQ ID NO 29
<211> LENGTH: 780
<212> TYPE: DNA
<213> ORGANISM: Artificial Sequence
<220> FEATURE:
<223> OTHER INFORMATION: NY-ESO-1/LAGE construct

<400> SEQUENCE: 29

```
atgggccatc atcatcatca tcatcatcat catcacagca gcggccatat cgacgacgac    60
gacaagcata tggcaggcgc agcacgtgca tctggtccgg gtggtggtgc accgcgcggt   120
ccgcatggtg gtgcggcgag cggcctgaat ggttgctgcc gttgcggtgc cgtggtccg    180
gaaagccgtc tgctggaatt ttatctggcc atgccgtttg cgaccccgat ggaagcggaa   240
ctggcccgtc gtagcctggc tcaagatgca ccgccgctgc cggttccggg cgtgctgctg   300
aaagaattta ccgtgagcgg caacattctg accattcgtc tgacggcggc agaccatcgt   360
cagctgcaac tgagcattag cagctgcctg caacagctgt ctctgctgat gtggattacc   420
cagtgctttc tgccggtgtt tctggcccag ccgccgtctg tcaacgtggt ggcgcgcgt    480
cgtccggatt ctcgcctgct ggaactgcat attaccatgc cgttcagctc tccaatggag   540
gccgaattag tgcgtcgcat tctgagccgt gatgcggcac cgctgccgcg tccaggtgcg   600
gttctgaaag acttcaccgt atctggcaac ctgctgttta ccgtctgac cgcagcggac    660
caccgccaat acaattatc tatcagctct tgtttacaac aactgtcgct gttaatgtgg   720
atcactcaat gtttcctgcc agtattcctg gctcaggccc cgagcggtca gcgtcgttaa   780
```

<210> SEQ ID NO 30
<211> LENGTH: 259
<212> TYPE: PRT
<213> ORGANISM: Artificial Sequence
<220> FEATURE:
<223> OTHER INFORMATION: NY-ESO-1/LAGE construct

<400> SEQUENCE: 30

```
Met Gly His His His His His His His His Ser Ser Gly His
1               5                   10                  15

Ile Asp Asp Asp Lys His Met Ala Gly Ala Ala Arg Ala Ser Gly
            20                  25                  30

Pro Gly Gly Gly Ala Pro Arg Gly Pro His Gly Gly Ala Ala Ser Gly
        35                  40                  45

Leu Asn Gly Cys Cys Arg Cys Gly Ala Arg Gly Pro Glu Ser Arg Leu
    50                  55                  60

Leu Glu Phe Tyr Leu Ala Met Pro Phe Ala Thr Pro Met Glu Ala Glu
65                  70                  75                  80

Leu Ala Arg Arg Ser Leu Ala Gln Asp Ala Pro Pro Leu Pro Val Pro
                85                  90                  95

Gly Val Leu Leu Lys Glu Phe Thr Val Ser Gly Asn Ile Leu Thr Ile
```

```
                100              105              110
Arg Leu Thr Ala Ala Asp His Arg Gln Leu Gln Leu Ser Ile Ser Ser
            115                      120                  125

Cys Leu Gln Gln Leu Ser Leu Leu Met Trp Ile Thr Gln Cys Phe Leu
        130                      135              140

Pro Val Phe Leu Ala Gln Pro Ser Gly Gln Arg Gly Gly Ala Arg
145                 150                  155                  160

Arg Pro Asp Ser Arg Leu Leu Glu Leu His Ile Thr Met Pro Phe Ser
                165                  170                  175

Ser Pro Met Glu Ala Glu Leu Val Arg Arg Ile Leu Ser Arg Asp Ala
            180                      185                  190

Ala Pro Leu Pro Arg Pro Gly Ala Val Leu Lys Asp Phe Thr Val Ser
        195                      200                  205

Gly Asn Leu Leu Phe Ile Arg Leu Thr Ala Ala Asp His Arg Gln Leu
            210                  215                  220

Gln Leu Ser Ile Ser Ser Cys Leu Gln Gln Leu Ser Leu Leu Met Trp
225                  230                  235                  240

Ile Thr Gln Cys Phe Leu Pro Val Phe Leu Ala Gln Ala Pro Ser Gly
                245                  250                  255

Gln Arg Arg

<210> SEQ ID NO 31
<211> LENGTH: 729
<212> TYPE: DNA
<213> ORGANISM: Artificial Sequence
<220> FEATURE:
<223> OTHER INFORMATION: NY-ESO-1/LAGE construct

<400> SEQUENCE: 31
atgcatcatc atcatcatca cgcaggcgca gcacgtgcat ctggtccggg tggtggtgca      60
ccgcgcggtc cgcatggtgg tgcggcgagc ggcctgaatg gttgctgccg ttgcggtgcg     120
cgtggtccgg aaagccgtct gctggaattt tatctggcca tgccgtttgc gaccccgatg     180
gaagcggaac tggcccgtcg tagcctggct caagatgcac cgccgctgcc ggttccgggc     240
gtgctgctga agaatttac cgtgagcggc aacattctga ccattcgtct gacggcggca     300
gaccatcgtc agctgcaact gagcattagc agctgcctgc aacagctgtc tctgctgatg     360
tggattaccc agtgctttct gccggtgttt ctggcccagc cgccgtctgg tcaacgtggt     420
ggcgcgcgtc gtccggattc tcgcctgctg gaactgcata ttaccatgcc gttcagctct     480
ccaatggagg ccgaattagt gcgtcgcatt ctgagccgtg atgcggcacc gctgccgcgt     540
ccaggtgcgg ttctgaaaga cttcaccgta tctggcaacc tgctgtttat ccgtctgacc     600
gcagcggacc accgccaatt acaattatct atcagctctt gtttacaaca actgtcgctg     660
ttaatgtgga tcactcaatg tttcctgcca gtattcctgg ctcaggcccc gagcggtcag     720
cgtcgttaa                                                             729

<210> SEQ ID NO 32
<211> LENGTH: 242
<212> TYPE: PRT
<213> ORGANISM: Artificial Sequence
<220> FEATURE:
<223> OTHER INFORMATION: NY-ESO-1/LAGE construct

<400> SEQUENCE: 32

Met His His His His His His Ala Gly Ala Ala Arg Ala Ser Gly Pro
1               5                   10                  15
```

Gly Gly Gly Ala Pro Arg Gly Pro His Gly Gly Ala Ala Ser Gly Leu
            20                  25                  30

Asn Gly Cys Cys Arg Cys Gly Ala Arg Gly Pro Glu Ser Arg Leu Leu
         35                  40                  45

Glu Phe Tyr Leu Ala Met Pro Phe Ala Thr Pro Met Glu Ala Glu Leu
 50                  55                  60

Ala Arg Arg Ser Leu Ala Gln Asp Ala Pro Pro Leu Pro Val Pro Gly
 65                  70                  75                  80

Val Leu Leu Lys Glu Phe Thr Val Ser Gly Asn Ile Leu Thr Ile Arg
                 85                  90                  95

Leu Thr Ala Ala Asp His Arg Gln Leu Gln Leu Ser Ile Ser Ser Cys
             100                 105                 110

Leu Gln Gln Leu Ser Leu Leu Met Trp Ile Thr Gln Cys Phe Leu Pro
         115                 120                 125

Val Phe Leu Ala Gln Pro Pro Ser Gly Gln Arg Gly Gly Ala Arg Arg
     130                 135                 140

Pro Asp Ser Arg Leu Leu Glu Leu His Ile Thr Met Pro Phe Ser Ser
145                 150                 155                 160

Pro Met Glu Ala Glu Leu Val Arg Arg Ile Leu Ser Arg Asp Ala Ala
                 165                 170                 175

Pro Leu Pro Arg Pro Gly Ala Val Leu Lys Asp Phe Thr Val Ser Gly
             180                 185                 190

Asn Leu Leu Phe Ile Arg Leu Thr Ala Ala Asp His Arg Gln Leu Gln
         195                 200                 205

Leu Ser Ile Ser Ser Cys Leu Gln Gln Leu Ser Leu Leu Met Trp Ile
     210                 215                 220

Thr Gln Cys Phe Leu Pro Val Phe Leu Ala Gln Ala Pro Ser Gly Gln
225                 230                 235                 240

Arg Arg

<210> SEQ ID NO 33
<211> LENGTH: 918
<212> TYPE: DNA
<213> ORGANISM: Artificial Sequence
<220> FEATURE:
<223> OTHER INFORMATION: NY-ESO-1/LAGE construct

<400> SEQUENCE: 33
atgggccatc atcatcatca tcatcatcat catcacagca gcggccatat cgacgacgac    60
gacaagcata tgcaggcgga aggccgtggc accggtggta gcaccggcga tgcggatggt   120
ccgggcggtc cggtattcc ggacgggcct ggtggtaatg cgggtgggcc aggtgaagcg   180
ggtgcgaccg gtgtcgtgg tccgcggggg gcaggcgcag cacgtgcatc tggtccgggt   240
ggtggtgcac cgcgcggtcc gcatggtggt gcggcgagcg gcctgaatgg ttgctgccgt   300
tgcggtgcgc gtggtccgga aagccgtctg ctggaatttt atctggccat gccgtttgcg   360
accccgatgg aagcggaact ggcccgtcgt agcctggctc aagatgcacc gccgctgccg   420
gttccgggcg tgctgctgaa agaatttacc gtgagcggca cattctgac cattcgtctg   480 acggcggcag accatcgtca gctgcaactg agcattagca gctgcctgca acagctgtct   540
ctgctgatgt ggattaccca gtgctttctg ccggtgtttc tggcccagcc gccgtctggt   600
caacgtggtg gcgcgcgtcg tccggattct cgcctgctgg aactgcatat taccatgccg   660
ttcagctctc caatggaggc cgaattagtg cgtcgcattc tgagccgtga tgcggcaccg   720
ctgccgcgtc caggtgcggt tctgaaagac ttcaccgtat ctggcaacct gctgtttatc   780

```
cgtctgaccg cagcggacca ccgccaatta caattatcta tcagctcttg tttacaacaa    840
ctgtcgctgt taatgtggat cactcaatgt ttcctgccag tattcctggc tcaggccccg    900
agcggtcagc gtcgttaa                                                  918
```

<210> SEQ ID NO 34
<211> LENGTH: 305
<212> TYPE: PRT
<213> ORGANISM: Artificial Sequence
<220> FEATURE:
<223> OTHER INFORMATION: NY-ESO-1/LAGE construct

<400> SEQUENCE: 34

```
Met Gly His His His His His His His Ser Ser Gly His
 1               5                  10                  15

Ile Asp Asp Asp Lys His Met Gln Ala Glu Gly Arg Gly Thr Gly
                20                  25                  30

Gly Ser Thr Gly Asp Ala Asp Gly Pro Gly Gly Pro Gly Ile Pro Asp
                35                  40                  45

Gly Pro Gly Gly Asn Ala Gly Gly Pro Gly Glu Ala Gly Ala Thr Gly
        50                  55                  60

Gly Arg Gly Pro Arg Gly Ala Gly Ala Ala Arg Ala Ser Gly Pro Gly
65                  70                  75                  80

Gly Gly Ala Pro Arg Gly Pro His Gly Gly Ala Ala Ser Gly Leu Asn
                85                  90                  95

Gly Cys Cys Arg Cys Gly Ala Arg Gly Pro Glu Ser Arg Leu Leu Glu
            100                 105                 110

Phe Tyr Leu Ala Met Pro Phe Ala Thr Pro Met Glu Ala Glu Leu Ala
        115                 120                 125

Arg Arg Ser Leu Ala Gln Asp Ala Pro Pro Leu Pro Val Pro Gly Val
    130                 135                 140

Leu Leu Lys Glu Phe Thr Val Ser Gly Asn Ile Leu Thr Ile Arg Leu
145                 150                 155                 160

Thr Ala Ala Asp His Arg Gln Leu Gln Leu Ser Ile Ser Ser Cys Leu
                165                 170                 175

Gln Gln Leu Ser Leu Leu Met Trp Ile Thr Gln Cys Phe Leu Pro Val
            180                 185                 190

Phe Leu Ala Gln Pro Pro Ser Gly Gln Arg Gly Ala Arg Arg Pro
        195                 200                 205

Asp Ser Arg Leu Leu Glu Leu His Ile Thr Met Pro Phe Ser Ser Pro
    210                 215                 220

Met Glu Ala Glu Leu Val Arg Arg Ile Leu Ser Arg Asp Ala Ala Pro
225                 230                 235                 240

Leu Pro Arg Pro Gly Ala Val Leu Lys Asp Phe Thr Val Ser Gly Asn
                245                 250                 255

Leu Leu Phe Ile Arg Leu Thr Ala Ala Asp His Arg Gln Leu Gln Leu
            260                 265                 270

Ser Ile Ser Ser Cys Leu Gln Gln Leu Ser Leu Leu Met Trp Ile Thr
        275                 280                 285

Gln Cys Phe Leu Pro Val Phe Leu Ala Gln Ala Pro Ser Gly Gln Arg
    290                 295                 300

Arg
305
```

<210> SEQ ID NO 35
<211> LENGTH: 867
<212> TYPE: DNA

<213> ORGANISM: Artificial Sequence
<220> FEATURE:
<223> OTHER INFORMATION: NY-ESO-1/LAGE construct

<400> SEQUENCE: 35

```
atgcatcatc atcatcatca ccaggcggaa ggccgtggca ccggtggtag caccggcgat    60
gcggatggtc cggcggtcc gggtattccg gacgggcctg gtggtaatgc gggtgggcca   120
ggtgaagcgg gtgcgaccgg tggtcgtggt ccgcggggg caggcgcagc acgtgcatct   180
ggtccgggtg gtggtgcacc gcgcggtccg catggtggtg cggcgagcgg cctgaatggt   240
tgctgccgtt gcggtgcgcg tggtccggaa agccgtctgc tggaatttta tctggccatg   300
ccgtttgcga ccccgatgga agcggaactg gcccgtcgta gcctggctca gatgcaccg   360
ccgctgccga ttccgggcgt gctgctgaaa gaatttaccg tgagcggcaa cattctgacc   420
attcgtctga cggcggcaga ccatcgtcag ctgcaactga gcattagcag ctgcctgcaa   480
cagctgtctc tgctgatgtg gattacccag tgctttctgc cggtgtttct ggcccagccg   540
ccgtctggtc aacgtggtgg cgcgcgtcgt ccggattctc gcctgctgga actgcatatt   600
accatgccgt tcagctctcc aatggaggcc gaattagtgc gtcgcattct gagccgtgat   660
gcggcaccgc tgccgcgtcc aggtgcggtt ctgaaagact tcaccgtatc tggcaacctg   720
ctgtttatcc gtctgaccgc agcggaccac cgccaattac aattatctat cagctcttgt   780
ttacaacaac tgtcgctgtt aatgtggatc actcaatgtt tcctgccagt attcctggct   840
caggccccga gcggtcagcg tcgttaa                                       867
```

<210> SEQ ID NO 36
<211> LENGTH: 288
<212> TYPE: PRT
<213> ORGANISM: Artificial Sequence
<220> FEATURE:
<223> OTHER INFORMATION: NY-ESO-1/LAGE construct

<400> SEQUENCE: 36

```
Met His His His His His His Gln Ala Glu Gly Arg Gly Thr Gly Gly
  1               5                  10                  15

Ser Thr Gly Asp Ala Asp Gly Pro Gly Gly Pro Gly Ile Pro Asp Gly
             20                  25                  30

Pro Gly Gly Asn Ala Gly Gly Pro Gly Glu Ala Gly Ala Thr Gly Gly
         35                  40                  45

Arg Gly Pro Arg Gly Ala Gly Ala Ala Arg Ala Ser Gly Pro Gly Gly
     50                  55                  60

Gly Ala Pro Arg Gly Pro His Gly Gly Ala Ala Ser Gly Leu Asn Gly
 65                  70                  75                  80

Cys Cys Arg Cys Gly Ala Arg Gly Pro Glu Ser Arg Leu Leu Glu Phe
                 85                  90                  95

Tyr Leu Ala Met Pro Phe Ala Thr Pro Met Glu Ala Glu Leu Ala Arg
            100                 105                 110

Arg Ser Leu Ala Gln Asp Ala Pro Pro Leu Pro Val Pro Gly Val Leu
        115                 120                 125

Leu Lys Glu Phe Thr Val Ser Gly Asn Ile Leu Thr Ile Arg Leu Thr
    130                 135                 140

Ala Ala Asp His Arg Gln Leu Gln Leu Ser Ile Ser Ser Cys Leu Gln
145                 150                 155                 160

Gln Leu Ser Leu Leu Met Trp Ile Thr Gln Cys Phe Leu Pro Val Phe
                165                 170                 175

Leu Ala Gln Pro Pro Ser Gly Gln Arg Gly Gly Ala Arg Arg Pro Asp
```

Ser Arg Leu Leu Glu Leu His Ile Thr Met Pro Phe Ser Ser Pro Met
      180                 185                 190

Glu Ala Glu Leu Val Arg Arg Ile Leu Ser Arg Asp Ala Ala Pro Leu
    195                 200                 205

Pro Arg Pro Gly Ala Val Leu Lys Asp Phe Thr Val Ser Gly Asn Leu
210                 215                 220                 225

Leu Phe Ile Arg Leu Thr Ala Ala Asp His Arg Gln Leu Gln Leu Ser
                230                 235                 240

Ile Ser Ser Cys Leu Gln Gln Leu Ser Leu Leu Met Trp Ile Thr Gln
                245                 250                 255

Cys Phe Leu Pro Val Phe Leu Ala Gln Ala Pro Ser Gly Gln Arg Arg
                260                 265                 270

275                 280                 285

<210> SEQ ID NO 37
<211> LENGTH: 690
<212> TYPE: DNA
<213> ORGANISM: Artificial Sequence
<220> FEATURE:
<223> OTHER INFORMATION: NY-ESO-1/LAGE construct

<400> SEQUENCE: 37
atgggccatc atcatcatca tcatcatcat catcacagca gcggccatat cgacgacgac    60
gacaagcata tgggtgcgcg tcgtccggat agccgtctgc tggagctgca tattaccatg    120
ccgtttagca gcccaatgga agctgagctg gtgcgtcgta ttctgtctcg tgacgcagca    180
ccgctgccac gtccgggtgc ggttctgaaa gattttaccg tgagcggcaa cctgctgttt    240
attcgtctga ccgcggcaga tcatcgtcag ctgcaactga gcattagcag ctgcctgcaa    300
cagctgtctc tgctgatgtg gattacccag tgctttctgc cggtgtttct ggctcaggcg    360
ccgtctggtc agcgtcgtgg tggtgcccgt ggcccggaat ctcgtctgct ggaattttat    420
ctggccatgc cgttcgcgac gccgatgaaa gcagagctgg cccgtcgcag cctggctcag    480
gatgcaccgc cgctgccggt tccgggcgtg ctgctgaaag aatttacggt tagcggtaac    540
attctgacca tccgtctgac cgcagcggac caccgccaaa tgcaactgtc tatcagctct    600
tgcctgcaac aactgtcgtt attaatgtgg atcactcaat gttttttacc agtattcctg    660
gcccaaccgc cgagcggcca acgtcgttaa                                    690

<210> SEQ ID NO 38
<211> LENGTH: 229
<212> TYPE: PRT
<213> ORGANISM: Artificial Sequence
<220> FEATURE:
<223> OTHER INFORMATION: LAGE/NY-ESO-1 construct

<400> SEQUENCE: 38

Met Gly His His His His His His His His Ser Ser Gly His
1               5                   10                  15

Ile Asp Asp Asp Asp Lys His Met Gly Ala Arg Arg Pro Asp Ser Arg
                20                  25                  30

Leu Leu Glu Leu His Ile Thr Met Pro Phe Ser Ser Pro Met Glu Ala
            35                  40                  45

Glu Leu Val Arg Arg Ile Leu Ser Arg Asp Ala Ala Pro Leu Pro Arg
        50                  55                  60

Pro Gly Ala Val Leu Lys Asp Phe Thr Val Ser Gly Asn Leu Leu Phe
65                  70                  75                  80

Ile Arg Leu Thr Ala Ala Asp His Arg Gln Leu Gln Leu Ser Ile Ser

```
                    85                  90                  95
Ser Cys Leu Gln Gln Leu Ser Leu Leu Met Trp Ile Thr Gln Cys Phe
                100                 105                 110

Leu Pro Val Phe Leu Ala Gln Ala Pro Ser Gly Gln Arg Arg Gly Gly
            115                 120                 125

Ala Arg Gly Pro Glu Ser Arg Leu Leu Glu Phe Tyr Leu Ala Met Pro
        130                 135                 140

Phe Ala Thr Pro Met Glu Ala Glu Leu Ala Arg Arg Ser Leu Ala Gln
145                 150                 155                 160

Asp Ala Pro Pro Leu Pro Val Pro Gly Val Leu Leu Lys Glu Phe Thr
                165                 170                 175

Val Ser Gly Asn Ile Leu Thr Ile Arg Leu Thr Ala Ala Asp His Arg
            180                 185                 190

Gln Leu Gln Leu Ser Ile Ser Ser Cys Leu Gln Gln Leu Ser Leu Leu
        195                 200                 205

Met Trp Ile Thr Gln Cys Phe Leu Pro Val Phe Leu Ala Gln Pro Pro
    210                 215                 220

Ser Gly Gln Arg Arg
225

<210> SEQ ID NO 39
<211> LENGTH: 639
<212> TYPE: DNA
<213> ORGANISM: Artificial Sequence
<220> FEATURE:
<223> OTHER INFORMATION: LAGE/NY-ESO-1 construct

<400> SEQUENCE: 39
atgcatcatc atcatcatca cggtgcgcgt cgtccggata gccgtctgct ggagctgcat     60
attaccatgc cgtttagcag cccaatggaa gctgagctgg tgcgtcgtat tctgtctcgt    120
gacgcagcac cgctgccacg tccgggtgcg gttctgaaag attttaccgt gagcggcaac    180
ctgctgttta ttcgtctgac cgcggcagat catcgtcagc tgcaactgag cattagcagc    240
tgcctgcaac agctgtctct gctgatgtgg attacccagt gctttctgcc ggtgtttctg    300
gctcaggcgc cgtctggtca gcgtcgtggt ggtgcccgtg gccggaatc tcgtctgctg     360 gaatttatc tggccatgcc gttcgcgacg ccgatggaag cagagctggc ccgtcgcagc    420
ctggctcagg atgcaccgcc gctgccggtt ccgggcgtgc tgctgaaaga atttacggtt    480
agcggtaaca ttctgaccat ccgtctgacc gcagcggacc accgccaact gcaactgtct    540
atcagctctt gcctgcaaca actgtcgtta ttaatgtgga tcactcaatg ttttttacca    600
gtattcctgg cccaaccgcc gagcggccaa cgtcgttaa                           639

<210> SEQ ID NO 40
<211> LENGTH: 212
<212> TYPE: PRT
<213> ORGANISM: Artificial Sequence
<220> FEATURE:
<223> OTHER INFORMATION: LAGE/NY-ESO-1 construct

<400> SEQUENCE: 40

Met His His His His His His Gly Ala Arg Arg Pro Asp Ser Arg Leu
  1               5                  10                  15

Leu Glu Leu His Ile Thr Met Pro Phe Ser Ser Pro Met Glu Ala Glu
                 20                  25                  30

Leu Val Arg Arg Ile Leu Ser Arg Asp Ala Ala Pro Leu Pro Arg Pro
             35                  40                  45
```

Gly Ala Val Leu Lys Asp Phe Thr Val Ser Gly Asn Leu Leu Phe Ile
         50                  55                  60

Arg Leu Thr Ala Ala Asp His Arg Gln Leu Gln Leu Ser Ile Ser Ser
 65                  70                  75                  80

Cys Leu Gln Gln Leu Ser Leu Leu Met Trp Ile Thr Gln Cys Phe Leu
                 85                  90                  95

Pro Val Phe Leu Ala Gln Ala Pro Ser Gly Gln Arg Arg Gly Gly Ala
             100                 105                 110

Arg Gly Pro Glu Ser Arg Leu Leu Glu Phe Tyr Leu Ala Met Pro Phe
         115                 120                 125

Ala Thr Pro Met Glu Ala Glu Leu Ala Arg Arg Ser Leu Ala Gln Asp
     130                 135                 140

Ala Pro Pro Leu Pro Val Pro Gly Val Leu Leu Lys Glu Phe Thr Val
145                 150                 155                 160

Ser Gly Asn Ile Leu Thr Ile Arg Leu Thr Ala Ala Asp His Arg Gln
                 165                 170                 175

Leu Gln Leu Ser Ile Ser Ser Cys Leu Gln Gln Leu Ser Leu Leu Met
             180                 185                 190

Trp Ile Thr Gln Cys Phe Leu Pro Val Phe Leu Ala Gln Pro Pro Ser
         195                 200                 205

Gly Gln Arg Arg
    210

<210> SEQ ID NO 41
<211> LENGTH: 783
<212> TYPE: DNA
<213> ORGANISM: Artificial Sequence
<220> FEATURE:
<223> OTHER INFORMATION: LAGE/NY-ESO-1 construct

<400> SEQUENCE: 41
atgggccatc atcatcatca tcatcatcat catcacagca gcggccatat cgacgacgac    60
gacaagcata tggcaggtgc agcgcgtgca tctggtccag gtggcggtgc gccgcgtggc   120
ccgcatggtg gtgcagctag tgcgcaagat ggtcgttgcc cgtgtggtgc gcgtcgtccg   180
gatagccgtc tgctggagct gcatattacc atgccgttta gcagcccaat ggaagctgag   240
ctggtgcgtc gtattctgtc tcgtgacgca gcaccgctgc acgtccgggt gcggttctg    300 aaagatttta ccgtgagcgg caacctgctg tttattcgtc tgaccgcggc agatcatcgt   360
cagctgcaac tgagcattag cagctgcctg caacagctgt ctctgctgat gtggattacc   420
cagtgctttc tgccggtgtt tctggctcag gcgccgtctg gtcagcgtcg tggtggtgcc   480
cgtggcccgg aatctcgtct gctggaattt tatctggcca tgccgttcgc gacgccgatg   540
gaagcagagc tggcccgtcg cagcctggct caggatgcac cgccgctgcc ggttccgggc   600
gtgctgctga agaatttac ggttagcggt aacattctga ccatccgtct gaccgcagcg   660
gaccaccgcc aactgcaact gtctatcagc tcttgcctgc aacaactgtc gttattaatg   720
tggatcactc aatgtttttt accagtattc ctggcccaac cgccgagcgg ccaacgtcgt   780
taa                                                                  783

<210> SEQ ID NO 42
<211> LENGTH: 260
<212> TYPE: PRT
<213> ORGANISM: Artificial Sequence
<220> FEATURE:
<223> OTHER INFORMATION: LAGE/NY-ESO-1 construct

<400> SEQUENCE: 42

Met Gly His His His His His His His His Ser Ser Gly His
1               5                       10                  15

Ile Asp Asp Asp Lys His Met Ala Gly Ala Ala Arg Ala Ser Gly
            20                  25                  30

Pro Gly Gly Gly Ala Pro Arg Gly Pro His Gly Ala Ala Ser Ala
        35                  40                  45

Gln Asp Gly Arg Cys Pro Cys Gly Ala Arg Arg Pro Asp Ser Arg Leu
50                      55                  60

Leu Glu Leu His Ile Thr Met Pro Phe Ser Ser Pro Met Glu Ala Glu
65                  70                  75                  80

Leu Val Arg Arg Ile Leu Ser Arg Asp Ala Ala Pro Leu Pro Arg Pro
            85                  90                  95

Gly Ala Val Leu Lys Asp Phe Thr Val Ser Gly Asn Leu Leu Phe Ile
            100                 105                 110

Arg Leu Thr Ala Ala Asp His Arg Gln Leu Gln Leu Ser Ile Ser Ser
            115                 120                 125

Cys Leu Gln Gln Leu Ser Leu Leu Met Trp Ile Thr Gln Cys Phe Leu
130                 135                 140

Pro Val Phe Leu Ala Gln Ala Pro Ser Gly Gln Arg Arg Gly Gly Ala
145                 150                 155                 160

Arg Gly Pro Glu Ser Arg Leu Leu Glu Phe Tyr Leu Ala Met Pro Phe
            165                 170                 175

Ala Thr Pro Met Glu Ala Glu Leu Ala Arg Arg Ser Leu Ala Gln Asp
            180                 185                 190

Ala Pro Pro Leu Pro Val Pro Gly Val Leu Leu Lys Glu Phe Thr Val
            195                 200                 205

Ser Gly Asn Ile Leu Thr Ile Arg Leu Thr Ala Ala Asp His Arg Gln
            210                 215                 220

Leu Gln Leu Ser Ile Ser Ser Cys Leu Gln Gln Leu Ser Leu Leu Met
225                 230                 235                 240

Trp Ile Thr Gln Cys Phe Leu Pro Val Phe Leu Ala Gln Pro Pro Ser
                245                 250                 255

Gly Gln Arg Arg
            260

<210> SEQ ID NO 43
<211> LENGTH: 732
<212> TYPE: DNA
<213> ORGANISM: Artificial Sequence
<220> FEATURE:
<223> OTHER INFORMATION: LAGE/NY-ESO-1 construct

<400> SEQUENCE: 43
atgcatcatc atcatcatca cgcaggtgca gcgcgtgcat ctggtccagg tggcggtgcg     60
ccgcgtggcc cgcatggtgg tgcagctagt gcgcaagatg gtcgttgccc gtgtggtgcg    120
cgtcgtccgg atagccgtct gctggagctg catattacca tgccgtttag cagcccaatg    180
gaagctgagc tggtgcgtcg tattctgtct cgtgacgcag caccgctgcc acgtccgggt    240
gcggttctga aagattttac cgtgagcggc aacctgctgt ttattcgtct gaccgcggca    300
gatcatcgtc agctgcaact gagcattagc agctgcctgc aacagctgtc tctgctgatg    360
tggattaccc agtgctttct gccggtgttt ctggctcagg cgccgtctgg tcagcgtcgt    420
ggtggtgccc gtggcccgga atctcgtctg ctggaatttt atctggccat gccgttcgcg    480
acgccgatgg aagcagagct ggcccgtcgc agcctggctc aggatgcacc gccgctgccg    540

| gttccgggcg tgctgctgaa agaatttacg gttagcggta acattctgac catccgtctg | 600 |
| accgcagcgg accaccgcca actgcaactg tctatcagct cttgcctgca acaactgtcg | 660 |
| ttattaatgt ggatcactca atgttttta ccagtattcc tggcccaacc gccgagcggc | 720 |
| caacgtcgtt aa | 732 |

<210> SEQ ID NO 44
<211> LENGTH: 243
<212> TYPE: PRT
<213> ORGANISM: Artificial Sequence
<220> FEATURE:
<223> OTHER INFORMATION: LAGE/NY-ESO-1 construct

<400> SEQUENCE: 44

```
Met His His His His His His Ala Gly Ala Ala Arg Ala Ser Gly Pro
 1               5                   10                  15

Gly Gly Gly Ala Pro Arg Gly Pro His Gly Gly Ala Ala Ser Ala Gln
                20                  25                  30

Asp Gly Arg Cys Pro Cys Gly Ala Arg Arg Pro Asp Ser Arg Leu Leu
            35                  40                  45

Glu Leu His Ile Thr Met Pro Phe Ser Ser Pro Met Glu Ala Glu Leu
        50                  55                  60

Val Arg Arg Ile Leu Ser Arg Asp Ala Ala Pro Leu Pro Arg Pro Gly
65                  70                  75                  80

Ala Val Leu Lys Asp Phe Thr Val Ser Gly Asn Leu Leu Phe Ile Arg
                85                  90                  95

Leu Thr Ala Ala Asp His Arg Gln Leu Gln Leu Ser Ile Ser Ser Cys
            100                 105                 110

Leu Gln Gln Leu Ser Leu Leu Met Trp Ile Thr Gln Cys Phe Leu Pro
        115                 120                 125

Val Phe Leu Ala Gln Ala Pro Ser Gly Gln Arg Arg Gly Gly Ala Arg
    130                 135                 140

Gly Pro Glu Ser Arg Leu Leu Glu Phe Tyr Leu Ala Met Pro Phe Ala
145                 150                 155                 160

Thr Pro Met Glu Ala Glu Leu Ala Arg Arg Ser Leu Ala Gln Asp Ala
                165                 170                 175

Pro Pro Leu Pro Val Pro Gly Val Leu Leu Lys Glu Phe Thr Val Ser
            180                 185                 190

Gly Asn Ile Leu Thr Ile Arg Leu Thr Ala Ala Asp His Arg Gln Leu
        195                 200                 205

Gln Leu Ser Ile Ser Ser Cys Leu Gln Gln Leu Ser Leu Leu Met Trp
    210                 215                 220

Ile Thr Gln Cys Phe Leu Pro Val Phe Leu Ala Gln Pro Pro Ser Gly
225                 230                 235                 240

Gln Arg Arg
```

<210> SEQ ID NO 45
<211> LENGTH: 921
<212> TYPE: DNA
<213> ORGANISM: Artificial Sequence
<220> FEATURE:
<223> OTHER INFORMATION: LAGE/NY-ESO-1 construct

<400> SEQUENCE: 45

| atgggccatc atcatcatca tcatcatcat catcacagca gcggccatat cgacgacgac | 60 |
| gacaagcata tgcaggcgga aggccgtggt actggcggta gcaccggcga tgcagatggt | 120 |
| ccgggcggtc cgggtattcc ggatggtccg gtggtaatg caggtggtcc aggtgaagca | 180 |

```
ggtgcgactg gcggtcgtgg tccacgcggt gcaggtgcag cgcgtgcatc tggtccaggt    240
ggcggtgcgc cgcgtggccc gcatggtggt gcagctagtg cgcaagatgg tcgttgcccg    300
tgtggtgcgc gtcgtccgga tagccgtctg ctggagctgc atattaccat gccgtttagc    360
agcccaatgg aagctgagct ggtgcgtcgt attctgtctc gtgacgcagc accgctgcca    420
cgtccgggtg cggttctgaa agattttacc gtgagcggca acctgctgtt tattcgtctg    480
accgcggcag atcatcgtca gctgcaactg agcattagca gctgcctgca acagctgtct    540
ctgctgatgt ggattaccca gtgctttctg ccggtgtttc tggctcaggc gccgtctggt    600
cagcgtcgtg gtggtgcccg tggcccggaa tctcgtctgc tggaatttta tctggccatg    660
ccgttcgcga cgccgatgga agcagagctg gcccgtcgca gcctggctca ggatgcaccg    720
ccgctgccgg ttccgggcgt gctgctgaaa gaatttacgg ttagcggtaa cattctgacc    780
atccgtctga ccgcagcgga ccaccgccaa ctgcaactgt ctatcagctc ttgcctgcaa    840
caactgtcgt tattaatgtg gatcactcaa tgttttttac cagtattcct ggcccaaccg    900
ccgagcggcc aacgtcgtta a                                              921

<210> SEQ ID NO 46
<211> LENGTH: 306
<212> TYPE: PRT
<213> ORGANISM: Artificial Sequence
<220> FEATURE:
<223> OTHER INFORMATION: LAGE/NY-ESO-1 construct

<400> SEQUENCE: 46

Met Gly His His His His His His His His Ser Ser Gly His
  1               5                  10                  15

Ile Asp Asp Asp Lys His Met Gln Ala Glu Gly Arg Gly Thr Gly
             20                  25                  30

Gly Ser Thr Gly Asp Ala Asp Gly Pro Gly Gly Pro Gly Ile Pro Asp
             35                  40                  45

Gly Pro Gly Gly Asn Ala Gly Gly Pro Gly Glu Ala Gly Ala Thr Gly
             50                  55                  60

Gly Arg Gly Pro Arg Gly Ala Gly Ala Ala Arg Ala Ser Gly Pro Gly
 65                  70                  75                  80

Gly Gly Ala Pro Arg Gly Pro His Gly Gly Ala Ala Ser Ala Gln Asp
                 85                  90                  95

Gly Arg Cys Pro Cys Gly Ala Arg Arg Pro Asp Ser Arg Leu Leu Glu
                100                 105                 110

Leu His Ile Thr Met Pro Phe Ser Ser Pro Met Glu Ala Glu Leu Val
            115                 120                 125

Arg Arg Ile Leu Ser Arg Asp Ala Ala Pro Leu Pro Arg Pro Gly Ala
            130                 135                 140

Val Leu Lys Asp Phe Thr Val Ser Gly Asn Leu Leu Phe Ile Arg Leu
145                 150                 155                 160

Thr Ala Ala Asp His Arg Gln Leu Gln Leu Ser Ile Ser Ser Cys Leu
                165                 170                 175

Gln Gln Leu Ser Leu Leu Met Trp Ile Thr Gln Cys Phe Leu Pro Val
            180                 185                 190

Phe Leu Ala Gln Ala Pro Ser Gly Gln Arg Arg Gly Gly Ala Arg Gly
            195                 200                 205

Pro Glu Ser Arg Leu Leu Glu Phe Tyr Leu Ala Met Pro Phe Ala Thr
        210                 215                 220

Pro Met Glu Ala Glu Leu Ala Arg Arg Ser Leu Ala Gln Asp Ala Pro
```

```
225                 230                 235                 240
Pro Leu Pro Val Pro Gly Val Leu Leu Lys Glu Phe Thr Val Ser Gly
                245                 250                 255

Asn Ile Leu Thr Ile Arg Leu Thr Ala Ala Asp His Arg Gln Leu Gln
            260                 265                 270

Leu Ser Ile Ser Ser Cys Leu Gln Gln Leu Ser Leu Leu Met Trp Ile
        275                 280                 285

Thr Gln Cys Phe Leu Pro Val Phe Leu Ala Gln Pro Pro Ser Gly Gln
    290                 295                 300

Arg Arg
305

<210> SEQ ID NO 47
<211> LENGTH: 870
<212> TYPE: DNA
<213> ORGANISM: Artificial Sequence
<220> FEATURE:
<223> OTHER INFORMATION: LAGE/NY-ESO-1 construct

<400> SEQUENCE: 47
atgcatcatc atcatcatca ccaggcggaa ggccgtggta ctggcggtag caccggcgat    60
gcagatggtc cgggcggtcc gggtattccg gatggtccgg gtggtaatgc aggtggtcca   120
ggtgaagcag gtgcgactgg cggtcgtggt ccacgcggtg caggtgcagc gcgtgcatct   180
ggtccaggtg gcggtgcgcc gcgtggcccg catggtggtg cagctagtgc gcaagatggt   240
cgttgcccgt gtggtgcgcg tcgtccggat agccgtctgc tggagctgca tattaccatg   300
ccgtttagca gcccaatgga agctgagctg gtgcgtcgta ttctgtctcg tgacgcagca   360
ccgctgccac gtccgggtgc ggttctgaaa gattttaccg tgagcggcaa cctgctgttt   420
attcgtctga ccgcggcaga tcatcgtcag ctgcaactga gcattagcag ctgcctgcaa   480
cagctgtctc tgctgatgtg gattacccag tgctttctgc cggtgtttct ggctcaggcg   540
ccgtctggtc agcgtcgtgg tggtgcccgt ggcccggaat ctcgtctgct ggaattttat   600
ctggccatgc cgttcgcgac gccgatggaa gcagagctgg cccgtcgcag cctggctcag   660
gatgcaccgc cgctgccggt tccgggcgtg ctgctgaaag aatttacggt tagcggtaac   720
attctgacca tccgtctgac cgcagcggac caccgccaac tgcaactgtc tatcagctct   780
tgcctgcaac aactgtcgtt attaatgtgg atcactcaat gttttttacc agtattcctg   840
gcccaaccgc cgagcggcca acgtcgttaa                                    870

<210> SEQ ID NO 48
<211> LENGTH: 289
<212> TYPE: PRT
<213> ORGANISM: Artificial Sequence
<220> FEATURE:
<223> OTHER INFORMATION: LAGE/NY-ESO-1 construct

<400> SEQUENCE: 48

Met His His His His His His Gln Ala Glu Gly Arg Gly Thr Gly Gly
1               5                   10                  15

Ser Thr Gly Asp Ala Asp Gly Pro Gly Gly Pro Gly Ile Pro Asp Gly
            20                  25                  30

Pro Gly Gly Asn Ala Gly Gly Pro Gly Glu Ala Gly Ala Thr Gly Gly
        35                  40                  45

Arg Gly Pro Arg Gly Ala Gly Ala Ala Arg Ala Ser Gly Pro Gly Gly
    50                  55                  60

Gly Ala Pro Arg Gly Pro His Gly Gly Ala Ala Ser Ala Gln Asp Gly
```

```
                65                  70                  75                  80
Arg Cys Pro Cys Gly Ala Arg Arg Pro Asp Ser Arg Leu Leu Glu Leu
                    85                  90                  95

His Ile Thr Met Pro Phe Ser Ser Pro Met Glu Ala Glu Leu Val Arg
                    100                 105                 110

Arg Ile Leu Ser Arg Asp Ala Ala Pro Leu Pro Arg Pro Gly Ala Val
                    115                 120                 125

Leu Lys Asp Phe Thr Val Ser Gly Asn Leu Leu Phe Ile Arg Leu Thr
            130                 135                 140

Ala Ala Asp His Arg Gln Leu Gln Leu Ser Ile Ser Ser Cys Leu Gln
145                 150                 155                 160

Gln Leu Ser Leu Leu Met Trp Ile Thr Gln Cys Phe Leu Pro Val Phe
                    165                 170                 175

Leu Ala Gln Ala Pro Ser Gly Gln Arg Arg Gly Ala Arg Gly Pro
                    180                 185                 190

Glu Ser Arg Leu Leu Glu Phe Tyr Leu Ala Met Pro Phe Ala Thr Pro
                195                 200                 205

Met Glu Ala Glu Leu Ala Arg Arg Ser Leu Ala Gln Asp Ala Pro Pro
        210                 215                 220

Leu Pro Val Pro Gly Val Leu Leu Lys Glu Phe Thr Val Ser Gly Asn
225                 230                 235                 240

Ile Leu Thr Ile Arg Leu Thr Ala Ala Asp His Arg Gln Leu Gln Leu
                    245                 250                 255

Ser Ile Ser Ser Cys Leu Gln Gln Leu Ser Leu Leu Met Trp Ile Thr
                260                 265                 270

Gln Cys Phe Leu Pro Val Phe Leu Ala Gln Pro Pro Ser Gly Gln Arg
            275                 280                 285

Arg

<210> SEQ ID NO 49
<211> LENGTH: 180
<212> TYPE: PRT
<213> ORGANISM: Homo Sapien

<400> SEQUENCE: 49

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
                    20                  25                  30

Gly Pro Gly Glu Ala Gly Ala Thr Gly Gly Arg Gly Pro Arg Gly Ala
                35                  40                  45

Gly Ala Ala Arg Ala Ser Gly Pro Gly Gly Gly Ala Pro Arg Gly Pro
            50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                    85                  90                  95

Ala Thr Pro Met Glu Ala Glu Leu Ala Arg Arg Ser Leu Ala Gln Asp
                    100                 105                 110

Ala Pro Pro Leu Pro Val Pro Gly Val Leu Leu Lys Glu Phe Thr Val
                    115                 120                 125

Ser Gly Asn Ile Leu Thr Ile Arg Leu Thr Ala Ala Asp His Arg Gln
            130                 135                 140

Leu Gln Leu Ser Ile Ser Ser Cys Leu Gln Gln Leu Ser Leu Leu Met
145                 150                 155                 160
```

```
Trp Ile Thr Gln Cys Phe Leu Pro Val Phe Leu Ala Gln Pro Pro Ser
            165                 170                 175
Gly Gln Arg Arg
        180

<210> SEQ ID NO 50
<211> LENGTH: 420
<212> TYPE: DNA
<213> ORGANISM: Homo Sapien

<400> SEQUENCE: 50
atggcaggcg cagcacgtgc atctggtccg ggtggtggtg caccgcgcgg tccgcatggt    60
ggtgcggcga gcggcctgaa tggttgctgc cgttgcggtg cgcgtggtcc ggaaagccgt   120
ctgctggaat tttatctggc catgccgttt gcgaccccga tggaagcgga actggcccgt   180
cgtagcctgg ctcaagatgc accgccgctg ccggttccgg gcgtgctgct gaaagaattt   240
accgtgagcg gcaacattct gaccattcgt ctgacggcgg cagaccatcg tcagctgcaa   300
ctgagcatta gcagctgcct gcaacagctg tctctgctga tgtggattac ccagtgcttt   360
ctgccggtgt ttctggccca gccgccgtct ggtcaacgtc accaccacca ccaccactaa   420

<210> SEQ ID NO 51
<211> LENGTH: 139
<212> TYPE: PRT
<213> ORGANISM: Homo Sapien

<400> SEQUENCE: 51

Met Ala Gly Ala Ala Arg Ala Ser Gly Pro Gly Gly Ala Pro Arg
  1               5                  10                  15

Gly Pro His Gly Gly Ala Ala Ser Gly Leu Asn Gly Cys Cys Arg Cys
             20                  25                  30

Gly Ala Arg Gly Pro Glu Ser Arg Leu Leu Glu Phe Tyr Leu Ala Met
         35                  40                  45

Pro Phe Ala Thr Pro Met Glu Ala Glu Leu Ala Arg Arg Ser Leu Ala
     50                  55                  60

Gln Asp Ala Pro Pro Leu Pro Val Pro Gly Val Leu Leu Lys Glu Phe
 65                  70                  75                  80

Thr Val Ser Gly Asn Ile Leu Thr Ile Arg Leu Thr Ala Ala Asp His
                 85                  90                  95

Arg Gln Leu Gln Leu Ser Ile Ser Ser Cys Leu Gln Gln Leu Ser Leu
            100                 105                 110

Leu Met Trp Ile Thr Gln Cys Phe Leu Pro Val Phe Leu Ala Gln Pro
        115                 120                 125

Pro Ser Gly Gln Arg His His His His His His
    130                 135

<210> SEQ ID NO 52
<211> LENGTH: 750
<212> TYPE: DNA
<213> ORGANISM: Homo Sapien

<400> SEQUENCE: 52
atggatccaa gcagccattc atcaaatatg gcgaataccc aaatgaaatc agacaaaatc    60
attattgctc accgtggtgc tagcggttat ttaccagagc atacgttaga atctaaagca   120
cttgcgtttg cacaacaggc tgattattta gagcaagatt tagcaatgac taaggatggt   180
cgtttagtgg ttattcacga tcacttttta gatggcttga ctgatgttgc gaaaaaattc   240
```

```
ccacatcgtc atcgtaaaga tggccgttac tatgtcatcg actttacctt aaaagaaatt    300
caaagtttag aaatgacaga aaactttgaa accgcaggcg cagcacgtgc atctggtccg    360
ggtggtggtg caccgcgcgg tccgcatggt ggtgcggcga gcggcctgaa tggttgctgc    420
cgttgcggtc cgcgtggtcc ggaaagccgt ctgctggaat tttatctggc catgccgttt    480
gcgaccccga tggaagcgga actggcccgt cgtagcctgg ctcaagatgc accgccgctg    540
ccggttccgg gcgtgctgct gaaagaattt accgtgagcg caacattct gaccattcgt     600 ctgacggcgg cagaccatcg tcagctgcaa ctgagcatta gcagctgcct gcaacagctg    660
tctctgctga tgtggattac ccagtgcttt ctgccggtgt ttctggccca gccgccgtct    720
ggtcaacgtc accaccacca ccaccactaa                                     750
```

<210> SEQ ID NO 53
<211> LENGTH: 249
<212> TYPE: PRT
<213> ORGANISM: Homo Sapine

<400> SEQUENCE: 53

Met Asp Pro Ser Ser His Ser Ser Asn Met Ala Asn Thr Gln Met Lys
1               5                   10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Ala
            100                 105                 110

Gly Ala Ala Arg Ala Ser Gly Pro Gly Gly Gly Ala Pro Arg Gly Pro
        115                 120                 125

His Gly Gly Ala Ala Ser Gly Leu Asn Gly Cys Cys Arg Cys Gly Ala
    130                 135                 140

Arg Gly Pro Glu Ser Arg Leu Leu Glu Phe Tyr Leu Ala Met Pro Phe
145                 150                 155                 160

Ala Thr Pro Met Glu Ala Glu Leu Ala Arg Arg Ser Leu Ala Gln Asp
                165                 170                 175

Ala Pro Pro Leu Pro Val Pro Gly Val Leu Leu Lys Glu Phe Thr Val
            180                 185                 190

Ser Gly Asn Ile Leu Thr Ile Arg Leu Thr Ala Ala Asp His Arg Gln
        195                 200                 205

Leu Gln Leu Ser Ile Ser Ser Cys Leu Gln Gln Leu Ser Leu Leu Met
    210                 215                 220

Trp Ile Thr Gln Cys Phe Leu Pro Val Phe Leu Ala Gln Pro Pro Ser
225                 230                 235                 240

Gly Gln Arg His His His His His His
                245

<210> SEQ ID NO 54
<211> LENGTH: 327
<212> TYPE: DNA
<213> ORGANISM: Homo Sapine

```
<400> SEQUENCE: 54
atgggtgcgc gtggtccgga aagccgtctg ctggaatttt atctggccat gccgtttgcg      60
accccgatgg aagcggaact ggcccgtcgt agcctggctc aagatgcacc gccgctgccg     120
gttccgggcg tgctgctgaa agaatttacc gtgagcggca acattctgac cattcgtctg     180
acggcggcag accatcgtca gctgcaactg agcattagca gctgcctgca acagctgtct     240
ctgctgatgt ggattaccca gtgctttctg ccggtgtttc tggcccagcc gccgtctggt     300
caacgtcacc accaccaca ccactaa                                          327

<210> SEQ ID NO 55
<211> LENGTH: 108
<212> TYPE: PRT
<213> ORGANISM: Homo Sapien

<400> SEQUENCE: 55

Met Gly Ala Arg Gly Pro Glu Ser Arg Leu Leu Glu Phe Tyr Leu Ala
 1               5                  10                  15

Met Pro Phe Ala Thr Pro Met Glu Ala Glu Leu Ala Arg Arg Ser Leu
                20                  25                  30

Ala Gln Asp Ala Pro Pro Leu Pro Val Pro Gly Val Leu Leu Lys Glu
            35                  40                  45

Phe Thr Val Ser Gly Asn Ile Leu Thr Ile Arg Leu Thr Ala Ala Asp
        50                  55                  60

His Arg Gln Leu Gln Leu Ser Ile Ser Ser Cys Leu Gln Gln Leu Ser
65                  70                  75                  80

Leu Leu Met Trp Ile Thr Gln Cys Phe Leu Pro Val Phe Leu Ala Gln
                85                  90                  95

Pro Pro Ser Gly Gln Arg His His His His His His
            100                 105

<210> SEQ ID NO 56
<211> LENGTH: 657
<212> TYPE: DNA
<213> ORGANISM: Homo Sapien

<400> SEQUENCE: 56
atggatccaa gcagccattc atcaaatatg gcgaataccc aaatgaaatc agacaaaatc      60
attattgctc accgtggtgc tagcggttat ttaccagagc atacgttaga atctaaagca     120
cttgcgtttg cacaacaggc tgattattta gagcaagatt tagcaatgac taaggatggt     180
cgtttagtgg ttattcacga tcactttta gatggcttga ctgatgttgc gaaaaaattc     240
ccacatcgtc atcgtaaaga tggccgttac tatgtcatcg actttacctt aaaagaaatt     300
caaagtttag aaatgacaga aactttgaa ccggtgcgc gtggtccgga aagccgtctg      360
ctggaatttt atctggccat gccgtttgcg accccgatgg aagcggaact ggcccgtcgt     420
agcctggctc aagatgcacc gccgctgccg gttccgggcg tgctgctgaa agaatttacc     480
gtgagcggca acattctgac cattcgtctg acggcggcag accatcgtca gctgcaactg     540
agcattagca gctgcctgca acagctgtct ctgctgatgt ggattaccca gtgctttctg     600
ccggtgtttc tggcccagcc gccgtctggt caacgtcacc accaccaca ccactaa        657

<210> SEQ ID NO 57
<211> LENGTH: 218
<212> TYPE: PRT
<213> ORGANISM: Homo Sapien

<400> SEQUENCE: 57
```

```
Met Asp Pro Ser Ser His Ser Ser Asn Met Ala Asn Thr Gln Met Lys
  1               5                  10                  15

Ser Asp Lys Ile Ile Ile Ala His Arg Gly Ala Ser Gly Tyr Leu Pro
             20                  25                  30

Glu His Thr Leu Glu Ser Lys Ala Leu Ala Phe Ala Gln Gln Ala Asp
             35                  40                  45

Tyr Leu Glu Gln Asp Leu Ala Met Thr Lys Asp Gly Arg Leu Val Val
 50                  55                  60

Ile His Asp His Phe Leu Asp Gly Leu Thr Asp Val Ala Lys Lys Phe
 65                  70                  75                  80

Pro His Arg His Arg Lys Asp Gly Arg Tyr Tyr Val Ile Asp Phe Thr
                 85                  90                  95

Leu Lys Glu Ile Gln Ser Leu Glu Met Thr Glu Asn Phe Glu Thr Gly
                100                 105                 110

Ala Arg Gly Pro Glu Ser Arg Leu Leu Glu Phe Tyr Leu Ala Met Pro
            115                 120                 125

Phe Ala Thr Pro Met Glu Ala Glu Leu Ala Arg Arg Ser Leu Ala Gln
        130                 135                 140

Asp Ala Pro Pro Leu Pro Val Pro Gly Val Leu Leu Lys Glu Phe Thr
145                 150                 155                 160

Val Ser Gly Asn Ile Leu Thr Ile Arg Leu Thr Ala Ala Asp His Arg
                165                 170                 175

Gln Leu Gln Leu Ser Ile Ser Ser Cys Leu Gln Gln Leu Ser Leu Leu
                180                 185                 190

Met Trp Ile Thr Gln Cys Phe Leu Pro Val Phe Leu Ala Gln Pro Pro
            195                 200                 205

Ser Gly Gln Arg His His His His His His
        210                 215

<210> SEQ ID NO 58
<211> LENGTH: 180
<212> TYPE: PRT
<213> ORGANISM: Homo Sapien
<220> FEATURE:
<221> NAME/KEY: PEPTIDE
<222> LOCATION: (0)...(0)
<223> OTHER INFORMATION: Lage la

<400> SEQUENCE: 58

Met Gln Ala Glu Gly Gln Gly Thr Gly Ser Thr Gly Asp Ala Asp
  1               5                  10                  15

Gly Pro Gly Gly Pro Gly Ile Pro Asp Gly Pro Gly Gly Asn Ala Gly
             20                  25                  30

Gly Pro Gly Glu Ala Gly Ala Thr Gly Gly Arg Gly Pro Arg Gly Ala
             35                  40                  45

Gly Ala Ala Arg Ala Ser Gly Pro Arg Gly Gly Ala Pro Arg Gly Pro
 50                  55                  60

His Gly Gly Ala Ala Ser Ala Gln Asp Gly Arg Cys Pro Cys Gly Ala
 65                  70                  75                  80

Arg Arg Pro Asp Ser Arg Leu Leu Gln Leu His Ile Thr Met Pro Phe
                 85                  90                  95

Ser Ser Pro Met Glu Ala Glu Leu Val Arg Arg Ile Leu Ser Arg Asp
                100                 105                 110

Ala Ala Pro Leu Pro Arg Pro Gly Ala Val Leu Lys Asp Phe Thr Val
            115                 120                 125

Ser Gly Asn Leu Leu Phe Ile Arg Leu Thr Ala Ala Asp His Arg Gln
```

```
                130             135             140
Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Ala Pro Ser
                165                 170                 175

Gly Gln Arg Arg
            180

<210> SEQ ID NO 59
<211> LENGTH: 561
<212> TYPE: DNA
<213> ORGANISM: Homo Sapien

<400> SEQUENCE: 59
atgcaggcgg aaggccgtgg tactggcggt agcaccggcg atgcagatgg tccgggcggt    60
ccgggtattc cggatggtcc gggtggtaat gcaggtggtc caggtgaagc aggtgcgact   120
ggcggtcgtg gtccacgcgg tgcaggtgca gcgcgtgcat ctggtccagg tggcggtgcg   180
ccgcgtggcc cgcatggtgg tgcagctagt gcgcaagatg gtcgttgccc gtgtggtgcg   240
cgtcgtccgg atagccgtct gctggagctg catattacca tgccgtttag cagcccaatg   300
gaagctgagc tggtgcgtcg tattctgtct cgtgacgcag caccgctgcc acgtccgggt   360
gcggttctga aagattttac cgtgagcggc aacctgctgt ttattcgtct gaccgcggca   420
gatcatcgtc agctgcaact gagcattagc agctgcctgc aacagctgtc tctgctgatg   480
tggattaccc agtgctttct gccggtgttt ctggctcagg cgccgtctgg tcagcgtcgt   540
caccaccacc accaccacta a                                             561

<210> SEQ ID NO 60
<211> LENGTH: 186
<212> TYPE: PRT
<213> ORGANISM: Homo Sapien

<400> SEQUENCE: 60

Met Gln Ala Glu Gly Arg Gly Thr Gly Gly Ser Thr Gly Asp Ala Asp
 1               5                  10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Ala Pro Arg Gly Pro
    50                  55                  60

His Gly Gly Ala Ala Ser Ala Gln Asp Gly Arg Cys Pro Cys Gly Ala
65                  70                  75                  80

Arg Arg Pro Asp Ser Arg Leu Leu Glu Leu His Ile Thr Met Pro Phe
                85                  90                  95

Ser Ser Pro Met Glu Ala Glu Leu Val Arg Arg Ile Leu Ser Arg Asp
                100                 105                 110

Ala Ala Pro Leu Pro Arg Pro Gly Ala Val Leu Lys Asp Phe Thr Val
            115                 120                 125

Ser Gly Asn Leu Leu Phe Ile Arg Leu Thr Ala Ala Asp His Arg Gln
        130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Ala Pro Ser
                165                 170                 175
```

Gly Gln Arg Arg His His His His His His
            180                 185

<210> SEQ ID NO 61
<211> LENGTH: 891
<212> TYPE: DNA
<213> ORGANISM: Homo Sapien

<400> SEQUENCE: 61
atggatccaa gcagccattc atcaaatatg gcgaataccc aaatgaaatc agacaaaatc    60
attattgctc accgtggtgc tagcggttat ttaccagagc atacgttaga atctaaagca   120
cttgcgtttg cacaacaggc tgattattta gagcaagatt tagcaatgac taaggatggt   180
cgtttagtgg ttattcacga tcactttta gatggcttga ctgatgttgc gaaaaaattc    240
ccacatcgtc atcgtaaaga tggccgttac tatgtcatcg actttacctt aaaagaaatt   300
caaagtttag aaatgacaga aactttgaa acccaggcgg aaggccgtgg tactggcggt    360
agcaccggcg atgcagatgg tccgggcggt ccgggtattc cggatggtcc gggtggtaat   420
gcaggtggtc aggtgaagc aggtgcgact ggcggtcgtg gtccacgcgg tgcaggtgca    480
gcgcgtgcat ctggtccagg tggcggtgcg ccgcgtggcc cgcatggtgg tgcagctagt   540
gcgcaagatg gtcgttgccc gtgtggtgcg cgtcgtccgg atagccgtct gctggagctg   600
catattacca tgccgtttag cagcccaatg gaagctgagc tggtgcgtcg tattctgtct   660
cgtgacgcag caccgctgcc acgtccgggt gcggttctga agatttttac cgtgagcggc   720
aacctgctgt ttattcgtct gaccgcggca gatcatcgtc agctgcaact gagcattagc   780
agctgcctgc aacagctgtc tctgctgatg tggattaccc agtgctttct gccggtgttt   840
ctggctcagg cgccgtctgg tcagcgtcgt caccaccacc accaccacta a            891

<210> SEQ ID NO 62
<211> LENGTH: 296
<212> TYPE: PRT
<213> ORGANISM: Homo sapien

<400> SEQUENCE: 62

Met Asp Pro Ser Ser His Ser Ser Asn Met Ala Asn Thr Gln Met Lys
 1               5                  10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Gln
            100                 105                 110

Ala Glu Gly Arg Gly Thr Gly Gly Ser Thr Gly Asp Ala Asp Gly Pro
        115                 120                 125

Gly Gly Pro Gly Ile Pro Asp Gly Pro Gly Gly Asn Ala Gly Gly Pro
    130                 135                 140

Gly Glu Ala Gly Ala Thr Gly Arg Gly Pro Arg Gly Ala Gly Ala
145                 150                 155                 160

Ala Arg Ala Ser Gly Pro Gly Gly Gly Ala Pro Arg Gly Pro His Gly

```
                    165                 170                 175
Gly Ala Ala Ser Ala Gln Asp Gly Arg Cys Pro Cys Gly Ala Arg Arg
                180                 185                 190

Pro Asp Ser Arg Leu Leu Glu Leu His Ile Thr Met Pro Phe Ser Ser
            195                 200                 205

Pro Met Glu Ala Glu Leu Val Arg Arg Ile Leu Ser Arg Asp Ala Ala
        210                 215                 220

Pro Leu Pro Arg Pro Gly Ala Val Leu Lys Asp Phe Thr Val Ser Gly
225                 230                 235                 240

Asn Leu Leu Phe Ile Arg Leu Thr Ala Ala Asp His Arg Gln Leu Gln
                245                 250                 255

Leu Ser Ile Ser Ser Cys Leu Gln Gln Leu Ser Leu Leu Met Trp Ile
            260                 265                 270

Thr Gln Cys Phe Leu Pro Val Phe Leu Ala Gln Ala Pro Ser Gly Gln
        275                 280                 285

Arg Arg His His His His His His
            290                 295

<210> SEQ ID NO 63
<211> LENGTH: 423
<212> TYPE: DNA
<213> ORGANISM: Homo Sapien

<400> SEQUENCE: 63
atggcaggtg cagcgcgtgc atctggtcca ggtggcggtg cgccgcgtgg cccgcatggt    60
ggtgcagcta gtgcgcaaga tggtcgttgc ccgtgtggtg cgcgtcgtcc ggatagccgt   120
ctgctggagc tgcatattac catgccgttt agcagcccaa tggaagctga gctggtgcgt   180
cgtattctgt ctcgtgacgc agcaccgctg ccacgtccgg gtgcggttct gaaagatttt   240
accgtgagcg gcaacctgct gtttattcgt ctgaccgcgg cagatcatcg tcagctgcaa   300
ctgagcatta gcagctgcct gcaacagctg tctctgctga tgtggattac ccagtgcttt   360
ctgccggtgt ttctggctca ggcgccgtct ggtcagcgtc gtcaccacca ccaccaccac   420
taa                                                                 423

<210> SEQ ID NO 64
<211> LENGTH: 140
<212> TYPE: PRT
<213> ORGANISM: Homo Sapien

<400> SEQUENCE: 64

Met Ala Gly Ala Ala Arg Ala Ser Gly Pro Gly Gly Gly Ala Pro Arg
1               5                   10                  15

Gly Pro His Gly Gly Ala Ala Ser Ala Gln Asp Gly Arg Cys Pro Cys
            20                  25                  30

Gly Ala Arg Arg Pro Asp Ser Arg Leu Leu Glu Leu His Ile Thr Met
        35                  40                  45

Pro Phe Ser Ser Pro Met Glu Ala Glu Leu Val Arg Arg Ile Leu Ser
    50                  55                  60

Arg Asp Ala Ala Pro Leu Pro Arg Pro Gly Ala Val Leu Lys Asp Phe
65                  70                  75                  80

Thr Val Ser Gly Asn Leu Leu Phe Ile Arg Leu Thr Ala Ala Asp His
                85                  90                  95

Arg Gln Leu Gln Leu Ser Ile Ser Ser Cys Leu Gln Gln Leu Ser Leu
            100                 105                 110

Leu Met Trp Ile Thr Gln Cys Phe Leu Pro Val Phe Leu Ala Gln Ala
```

Pro Ser Gly Gln Arg Arg His His His His His
    130                 135                 140

<210> SEQ ID NO 65
<211> LENGTH: 753
<212> TYPE: DNA
<213> ORGANISM: Homo Sapoem

<400> SEQUENCE: 65
atggatccaa gcagccattc atcaaatatg gcgaataccc aaatgaaatc agacaaaatc      60
attattgctc accgtggtgc tagcggttat ttaccagagc atacgttaga atctaaagca     120
cttgcgtttg cacaacaggc tgattattta gagcaagatt tagcaatgac taaggatggt     180
cgtttagtgg ttattcacga tcactttta gatggcttga ctgatgttgc gaaaaaattc      240
ccacatcgtc atcgtaaaga tggccgttac tatgtcatcg actttacctt aaaagaaatt     300
caaagtttag aaatgacaga aactttgaa accgcaggtg cagcgcgtgc atctggtcca      360
ggtggcggtg cgccgcgtgg cccgcatggt ggtgcagcta gtgcgcaaga tggtcgttgc     420
ccgtgtggtg cgcgtcgtcc ggatagccgt ctgctggagc tgcatattac catgccgttt     480
agcagcccaa tggaagctga gctggtgcgt cgtattctgt ctcgtgacgc agcaccgctg     540
ccacgtccgg gtgcggttct gaaagatttt accgtgagcg gcaacctgct gtttattcgt     600
ctgaccgcgg cagatcatcg tcagctgcaa ctgagcatta gcagctgcct gcaacagctg     660
tctctgctga tgtggattac ccagtgcttt ctgccggtgt ttctggctca ggcgccgtct     720
ggtcagcgtc gtcaccacca ccaccaccac taa                                  753

<210> SEQ ID NO 66
<211> LENGTH: 250
<212> TYPE: PRT
<213> ORGANISM: Homo Sapien

<400> SEQUENCE: 66

Met Asp Pro Ser Ser His Ser Ser Asn Met Ala Asn Thr Gln Met Lys
 1               5                  10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Ala
            100                 105                 110

Gly Ala Ala Arg Ala Ser Gly Pro Gly Gly Gly Ala Pro Arg Gly Pro
        115                 120                 125

His Gly Gly Ala Ala Ser Ala Gln Asp Gly Arg Cys Pro Cys Gly Ala
    130                 135                 140

Arg Arg Pro Asp Ser Arg Leu Leu Glu Leu His Ile Thr Met Pro Phe
145                 150                 155                 160

Ser Ser Pro Met Glu Ala Glu Leu Val Arg Arg Ile Leu Ser Arg Asp
                165                 170                 175

```
Ala Ala Pro Leu Pro Arg Pro Gly Ala Val Leu Lys Asp Phe Thr Val
            180                 185                 190

Ser Gly Asn Leu Leu Phe Ile Arg Leu Thr Ala Ala Asp His Arg Gln
        195                 200                 205

Leu Gln Leu Ser Ile Ser Ser Cys Leu Gln Gln Leu Ser Leu Leu Met
    210                 215                 220

Trp Ile Thr Gln Cys Phe Leu Pro Val Phe Leu Ala Gln Ala Pro Ser
225                 230                 235                 240

Gly Gln Arg Arg His His His His His
                245                 250

<210> SEQ ID NO 67
<211> LENGTH: 330
<212> TYPE: DNA
<213> ORGANISM: Homo sapien

<400> SEQUENCE: 67
atgggtgcgc gtcgtccgga tagccgtctg ctggagctgc atattaccat gccgtttagc      60
agcccaatgg aagctgagct ggtgcgtcgt attctgtctc gtgacgcagc accgctgcca     120
cgtccgggtg cggttctgaa agattttacc gtgagcggca acctgctgtt tattcgtctg     180
accgcggcag atcatcgtca gctgcaactg agcattagca gctgcctgca acagctgtct     240
ctgctgatgt ggattaccca gtgctttctg ccggtgtttc tggctcaggc gccgtctggt     300
cagcgtcgtc accaccacca ccaccactaa                                      330

<210> SEQ ID NO 68
<211> LENGTH: 109
<212> TYPE: PRT
<213> ORGANISM: Homo Sapien

<400> SEQUENCE: 68

Met Gly Ala Arg Arg Pro Asp Ser Arg Leu Leu Glu Leu His Ile Thr
  1               5                  10                  15

Met Pro Phe Ser Ser Pro Met Glu Ala Glu Leu Val Arg Arg Ile Leu
             20                  25                  30

Ser Arg Asp Ala Ala Pro Leu Pro Arg Pro Gly Ala Val Leu Lys Asp
         35                  40                  45

Phe Thr Val Ser Gly Asn Leu Leu Phe Ile Arg Leu Thr Ala Ala Asp
     50                  55                  60

His Arg Gln Leu Gln Leu Ser Ile Ser Ser Cys Leu Gln Gln Leu Ser
 65                  70                  75                  80

Leu Leu Met Trp Ile Thr Gln Cys Phe Leu Pro Val Phe Leu Ala Gln
                 85                  90                  95

Ala Pro Ser Gly Gln Arg Arg His His His His His
            100                 105

<210> SEQ ID NO 69
<211> LENGTH: 660
<212> TYPE: DNA
<213> ORGANISM: Homo Sapien

<400> SEQUENCE: 69
atggatccaa gcagccattc atcaaatatg gcgaataccc aaatgaaatc agacaaaatc      60
attattgctc accgtggtgc tagcggttat ttaccagagc atacgttaga atctaaagca     120
cttgcgtttg cacaacaggc tgattattta gagcaagatt tagcaatgac taaggatggt     180
cgtttagtgg ttattcacga tcactttta gatggcttga ctgatgttgc gaaaaaattc     240
```

```
ccacatcgtc atcgtaaaga tggccgttac tatgtcatcg actttacctt aaaagaaatt    300
caaagtttag aaatgacaga aaactttgaa accggtgcgc gtcgtccgga tagccgtctg    360
ctggagctgc atattaccat gccgtttagc agcccaatgg aagctgagct ggtgcgtcgt    420
attctgtctc gtgacgcagc accgctgcca cgtccgggtg cggttctgaa agattttacc    480
gtgagcggca acctgctgtt tattcgtctg accgcggcag atcatcgtca gctgcaactg    540
agcattagca gctgcctgca acagctgtct ctgctgatgt ggattaccca gtgctttctg    600
ccggtgtttc tggctcaggc gccgtctggt cagcgtcgtc accaccacca ccaccactaa    660
```

<210> SEQ ID NO 70
<211> LENGTH: 219
<212> TYPE: PRT
<213> ORGANISM: Homo Sapien

<400> SEQUENCE: 70

```
Met Asp Pro Ser Ser His Ser Ser Asn Met Ala Asn Thr Gln Met Lys
 1               5                  10                  15

Ser Asp Lys Ile Ile Ile Ala His Arg Gly Ala Ser Gly Tyr Leu Pro
             20                  25                  30

Glu His Thr Leu Glu Ser Lys Ala Leu Ala Phe Ala Gln Gln Ala Asp
         35                  40                  45

Tyr Leu Glu Gln Asp Leu Ala Met Thr Lys Asp Gly Arg Leu Val Val
     50                  55                  60

Ile His Asp His Phe Leu Asp Gly Leu Thr Asp Val Ala Lys Lys Phe
 65                  70                  75                  80

Pro His Arg His Arg Lys Asp Gly Arg Tyr Tyr Val Ile Asp Phe Thr
                 85                  90                  95

Leu Lys Glu Ile Gln Ser Leu Glu Met Thr Glu Asn Phe Glu Thr Gly
            100                 105                 110

Ala Arg Arg Pro Asp Ser Arg Leu Leu Glu Leu His Ile Thr Met Pro
        115                 120                 125

Phe Ser Ser Pro Met Glu Ala Glu Leu Val Arg Arg Ile Leu Ser Arg
    130                 135                 140

Asp Ala Ala Pro Leu Pro Arg Pro Gly Ala Val Leu Lys Asp Phe Thr
145                 150                 155                 160

Val Ser Gly Asn Leu Leu Phe Ile Arg Leu Thr Ala Ala Asp His Arg
                165                 170                 175

Gln Leu Gln Leu Ser Ile Ser Ser Cys Leu Gln Gln Leu Ser Leu Leu
            180                 185                 190

Met Trp Ile Thr Gln Cys Phe Leu Pro Val Phe Leu Ala Gln Ala Pro
        195                 200                 205

Ser Gly Gln Arg Arg His His His His His
    210                 215
```

<210> SEQ ID NO 71
<211> LENGTH: 210
<212> TYPE: PRT
<213> ORGANISM: Homo Sapien
<220> FEATURE:
<221> NAME/KEY: PEPTIDE
<222> LOCATION: (0)...(0)
<223> OTHER INFORMATION: Lage 1b

<400> SEQUENCE: 71

```
Met Gln Ala Glu Gly Gln Gly Thr Gly Gly Ser Thr Gly Asp Ala Asp
 1               5                  10                  15

Gly Pro Gly Gly Pro Gly Ile Pro Asp Gly Pro Gly Gly Asn Ala Gly
```

```
            20                  25                  30
Gly Pro Gly Glu Ala Gly Ala Thr Gly Gly Arg Gly Pro Arg Gly Ala
        35                  40                  45

Gly Ala Ala Arg Ala Ser Gly Pro Arg Gly Gly Ala Pro Arg Gly Pro
    50                  55                  60

His Gly Gly Ala Ala Ser Ala Gln Asp Gly Arg Cys Pro Cys Gly Ala
65                  70                  75                  80

Arg Arg Pro Asp Ser Arg Leu Leu Gln Leu His Ile Thr Met Pro Phe
                85                  90                  95

Ser Ser Pro Met Glu Ala Glu Leu Val Arg Arg Ile Leu Ser Arg Asp
            100                 105                 110

Ala Ala Pro Leu Pro Arg Pro Gly Ala Val Leu Lys Asp Phe Thr Val
        115                 120                 125

Ser Gly Asn Leu Leu Phe Met Ser Val Arg Asp Gln Asp Arg Glu Gly
    130                 135                 140

Ala Gly Arg Met Arg Val Val Gly Trp Gly Leu Gly Ser Ala Ser Pro
145                 150                 155                 160

Glu Gly Gln Lys Ala Arg Asp Leu Arg Thr Pro Lys His Lys Val Ser
                165                 170                 175

Glu Gln Arg Pro Gly Thr Pro Gly Pro Pro Pro Glu Gly Ala Gln
            180                 185                 190

Gly Asp Gly Cys Arg Gly Val Ala Phe Asn Val Met Phe Ser Ala Pro
        195                 200                 205

His Ile
    210

<210> SEQ ID NO 72
<211> LENGTH: 978
<212> TYPE: DNA
<213> ORGANISM: Homo Sapien

<400> SEQUENCE: 72
atggatccaa gcagccattc atcaaatatg gcgaatacccc aaatgaaatc agacaaaatc        60
attattgctc accgtggtgc tagcggttat ttaccagagc atacgttaga atctaaagca       120
cttgcgtttg cacaacaggc tgattattta gagcaagatt tagcaatgac taaggatggt       180
cgtttagtgg ttattcacga tcactttttta gatggcttga ctgatgttgc gaaaaaattc       240
ccacatcgtc atcgtaaaga tggccgttac tatgtcatcg actttacctt aaaagaaatt       300
caaagtttag aaatgacaga aaactttgaa accgcggccg cacatatggg tgcgcgtggt       360
ccggaaagcc gtctgctgga attttatctg gccatgccgt ttgcgacccc gatggaagcg       420
gaactggccc gtcgtagcct ggctcaagat gcaccgccgc tgccggttcc gggcgtgctg       480
ctgaaagaat taccgtgag cggcaacatt ctgaccattc gtctgacggc ggcagaccat       540
cgtcagctgc aactgagcat tagcagctgc ctgcaacagc tgtctctgct gatgtggatt       600
acccagtgct ttctgccggt gtttctggcc cagccgccgt ctggtcaacg tggtggcgcg       660
cgtcgtccgg attctcgcct gctggaactg catattacca tgccgttcag ctctccaatg       720
gaggccgaat tagtgcgtcg cattctgagc cgtgatgcgg caccgctgcc gcgtccaggt       780
gcggttctga aagacttcac cgtatctggc aacctgctgt ttatccgtct gaccgcagcg       840
gaccaccgcc aattacaatt atctatcagc tcttgtttac aacaactgtc gctgttaatg       900
tggatcactc aatgtttcct gccagtattc ctggctcagg cccgagcggg tcagcgtcgt       960
caccaccacc accaccac                                                     978
```

<210> SEQ ID NO 73
<211> LENGTH: 326
<212> TYPE: PRT
<213> ORGANISM: Homo Sapien

<400> SEQUENCE: 73

Met Asp Pro Ser Ser His Ser Ser Asn Met Ala Asn Thr Gln Met Lys
1               5                   10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Ala
            100                 105                 110

Ala Ala His Met Gly Ala Arg Gly Pro Glu Ser Arg Leu Leu Glu Phe
        115                 120                 125

Tyr Leu Ala Met Pro Phe Ala Thr Pro Met Glu Ala Glu Leu Ala Arg
    130                 135                 140

Arg Ser Leu Ala Gln Asp Ala Pro Pro Leu Pro Val Pro Gly Val Leu
145                 150                 155                 160

Leu Lys Glu Phe Thr Val Ser Gly Asn Ile Leu Thr Ile Arg Leu Thr
                165                 170                 175

Ala Ala Asp His Arg Gln Leu Gln Leu Ser Ile Ser Ser Cys Leu Gln
            180                 185                 190

Gln Leu Ser Leu Leu Met Trp Ile Thr Gln Cys Phe Leu Pro Val Phe
        195                 200                 205

Leu Ala Gln Pro Pro Ser Gly Gln Arg Gly Gly Ala Arg Arg Pro Asp
    210                 215                 220

Ser Arg Leu Leu Glu Leu His Ile Thr Met Pro Phe Ser Ser Pro Met
225                 230                 235                 240

Glu Ala Glu Leu Val Arg Arg Ile Leu Ser Arg Asp Ala Ala Pro Leu
                245                 250                 255

Pro Arg Pro Gly Ala Val Leu Lys Asp Phe Thr Val Ser Gly Asn Leu
            260                 265                 270

Leu Phe Ile Arg Leu Thr Ala Ala Asp His Arg Gln Leu Gln Leu Ser
        275                 280                 285

Ile Ser Ser Cys Leu Gln Gln Leu Ser Leu Leu Met Trp Ile Thr Gln
    290                 295                 300

Cys Phe Leu Pro Val Phe Leu Ala Gln Ala Pro Ser Gly Gln Arg Arg
305                 310                 315                 320

His His His His His His
                325

<210> SEQ ID NO 74
<211> LENGTH: 1209
<212> TYPE: DNA
<213> ORGANISM: Homo Sapien

<400> SEQUENCE: 74
atggatccaa gcagccattc atcaaatatg gcgaataccc aaatgaaatc agacaaaatc      60

```
attattgctc accgtggtgc tagcggttat ttaccagagc atacgttaga atctaaagca    120
cttgcgtttg cacaacaggc tgattattta gagcaagatt tagcaatgac taaggatggt    180
cgtttagtgg ttattcacga tcactttta gatggcttga ctgatgttgc gaaaaaattc    240
ccacatcgtc atcgtaaaga tggccgttac tatgtcatcg actttacctt aaaagaaatt    300
caaagtttag aaatgacaga aactttgaa accgcggccg cacatatgca ggcggaaggc    360
cgtggcaccg gtggtagcac cggcgatgcg gatggtccgg gcggtccggg tattccggac    420
gggcctggtg gtaatgcggg tgggccaggt gaagcgggtg cgaccggtgg tcgtggtccg    480
cggggggcag gcgcagcacg tgcatctggt ccgggtggtg gtgcaccgcg cggtccgcat    540
ggtggtgcgg cgagcggcct gaatggttgc tgccgttgcg gtgcgcgtgg tccggaaagc    600
cgtctgctgg aattttatct ggccatgccg tttgcgaccc cgatggaagc ggaactggcc    660
cgtcgtagcc tggctcaaga tgcaccgccg ctgccggttc cgggcgtgct gctgaaagaa    720
tttaccgtga gcggcaacat tctgaccatt cgtctgacgg cggcagacca tcgtcagctg    780
caactgagca ttagcagctg cctgcaacag ctgtctctgc tgatgtggat acccagtgc     840 tttctgccgg tgtttctggc ccagccgccg tctggtcaac gtggtggcgc gcgtcgtccg    900
gattctcgcc tgctggaact gcatattacc atgccgttca gctctccaat ggaggccgaa    960
ttagtgcgtc gcattctgag ccgtgatgcg gcaccgctgc cgcgtccagg tgcggttctg   1020
aaagacttca ccgtatctgg caacctgctg tttatccgtc tgaccgcagc ggaccaccgc   1080
caattacaat tatctatcag ctcttgttta caacaactgt cgctgttaat gtggatcact   1140
caatgtttcc tgccagtatt cctggctcag gccccgagcg gtcagcgtcg tcaccaccac   1200
caccaccac                                                           1209
```

<210> SEQ ID NO 75
<211> LENGTH: 403
<212> TYPE: PRT
<213> ORGANISM: Homo Sapien

<400> SEQUENCE: 75

```
Met Asp Pro Ser Ser His Ser Ser Asn Met Ala Asn Thr Gln Met Lys
 1               5                  10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Ala
            100                 105                 110

Ala Ala His Met Gln Ala Glu Gly Arg Gly Thr Gly Gly Ser Thr Gly
        115                 120                 125

Asp Ala Asp Gly Pro Gly Gly Pro Gly Ile Pro Asp Gly Pro Gly Gly
    130                 135                 140

Asn Ala Gly Gly Pro Gly Glu Ala Gly Ala Thr Gly Gly Arg Gly Pro
145                 150                 155                 160

Arg Gly Ala Gly Ala Ala Arg Ala Ser Gly Pro Gly Gly Gly Ala Pro
```

```
                165                 170                 175
Arg Gly Pro His Gly Gly Ala Ala Ser Gly Leu Asn Gly Cys Cys Arg
            180                 185                 190

Cys Gly Ala Arg Gly Pro Glu Ser Arg Leu Leu Glu Phe Tyr Leu Ala
            195                 200                 205

Met Pro Phe Ala Thr Pro Met Glu Ala Glu Leu Ala Arg Arg Ser Leu
    210                 215                 220

Ala Gln Asp Ala Pro Pro Leu Pro Val Pro Gly Val Leu Leu Lys Glu
225                 230                 235                 240

Phe Thr Val Ser Gly Asn Ile Leu Thr Ile Arg Leu Thr Ala Ala Asp
                245                 250                 255

His Arg Gln Leu Gln Leu Ser Ile Ser Ser Cys Leu Gln Gln Leu Ser
            260                 265                 270

Leu Leu Met Trp Ile Thr Gln Cys Phe Leu Pro Val Phe Leu Ala Gln
        275                 280                 285

Pro Pro Ser Gly Gln Arg Gly Gly Ala Arg Arg Pro Asp Ser Arg Leu
    290                 295                 300

Leu Glu Leu His Ile Thr Met Pro Phe Ser Ser Pro Met Glu Ala Glu
305                 310                 315                 320

Leu Val Arg Arg Ile Leu Ser Arg Asp Ala Ala Pro Leu Pro Arg Pro
                325                 330                 335

Gly Ala Val Leu Lys Asp Phe Thr Val Ser Gly Asn Leu Leu Phe Ile
            340                 345                 350

Arg Leu Thr Ala Ala Asp His Arg Gln Leu Gln Leu Ser Ile Ser Ser
        355                 360                 365

Cys Leu Gln Gln Leu Ser Leu Leu Met Trp Ile Thr Gln Cys Phe Leu
    370                 375                 380

Pro Val Phe Leu Ala Gln Ala Pro Ser Gly Gln Arg Arg His His His
385                 390                 395                 400

His His His

<210> SEQ ID NO 76
<211> LENGTH: 981
<212> TYPE: DNA
<213> ORGANISM: Homo Sapien

<400> SEQUENCE: 76
atggatccaa gcagccattc atcaaatatg gcgaatacccc aaatgaaatc agacaaaatc      60
attattgctc accgtggtgc tagcggttat ttaccagagc atacgttaga atctaaagca     120
cttgcgtttg cacaacaggc tgattattta gagcaagatt tagcaatgac taaggatggt     180
cgtttagtgg ttattcacga tcactttta gatggcttga ctgatgttgc gaaaaaattc     240
ccacatcgtc atcgtaaaga tggccgttac tatgtcatcg actttacctt aaaagaaatt     300
caaagtttag aaatgacaga aaactttgaa accgcggccg cacatatggg tgcgcgtcgt     360
ccggatagcc gtctgctgga gctgcatatt accatgccgt ttagcagccc aatggaagct     420
gagctggtgc gtcgtattct gtctcgtgac gcagcaccgc tgccacgtcc gggtgcggtt     480
ctgaaagatt ttaccgtgag cggcaacctg ctgtttattc gtctgaccgc ggcagatcat     540
cgtcagctgc aactgagcat tagcagctgc ctgcaacagc tgtctctgct gatgtggatt     600
acccagtgct tctgccggt gttctggct caggcgccgt ctggtcagcg tcgtggtggt     660
gcccgtggcc cggaatctcg tctgctggaa tttatctgg ccatgccgtt cgcgacgccg     720
atggaagcag agctggcccg tcgcagcctg gctcaggatg caccgccgct gccggttccg     780
```

-continued

```
ggcgtgctgc tgaaagaatt tacggttagc ggtaacattc tgaccatccg tctgaccgca    840
gcggaccacc gccaactgca actgtctatc agctcttgcc tgcaacaact gtcgttatta    900
atgtggatca ctcaatgttt tttaccagta ttcctggccc aaccgccgag cggccaacgt    960
cgtcaccacc accaccacca c                                              981
```

<210> SEQ ID NO 77
<211> LENGTH: 327
<212> TYPE: PRT
<213> ORGANISM: Homo Sapien

<400> SEQUENCE: 77

```
Met Asp Pro Ser Ser His Ser Ser Asn Met Ala Asn Thr Gln Met Lys
 1               5                  10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Ala
            100                 105                 110

Ala Ala His Met Gly Ala Arg Arg Pro Asp Ser Arg Leu Leu Glu Leu
        115                 120                 125

His Ile Thr Met Pro Phe Ser Ser Pro Met Glu Ala Glu Leu Val Arg
    130                 135                 140

Arg Ile Leu Ser Arg Asp Ala Ala Pro Leu Pro Arg Pro Gly Ala Val
145                 150                 155                 160

Leu Lys Asp Phe Thr Val Ser Gly Asn Leu Leu Phe Ile Arg Leu Thr
                165                 170                 175

Ala Ala Asp His Arg Gln Leu Gln Leu Ser Ile Ser Ser Cys Leu Gln
            180                 185                 190

Gln Leu Ser Leu Leu Met Trp Ile Thr Gln Cys Phe Leu Pro Val Phe
        195                 200                 205

Leu Ala Gln Ala Pro Ser Gly Gln Arg Arg Gly Gly Ala Arg Gly Pro
    210                 215                 220

Glu Ser Arg Leu Leu Glu Phe Tyr Leu Ala Met Pro Phe Ala Thr Pro
225                 230                 235                 240

Met Glu Ala Glu Leu Ala Arg Arg Ser Leu Ala Gln Asp Ala Pro Pro
                245                 250                 255

Leu Pro Val Pro Gly Val Leu Leu Lys Glu Phe Thr Val Ser Gly Asn
            260                 265                 270

Ile Leu Thr Ile Arg Leu Thr Ala Ala Asp His Arg Gln Leu Gln Leu
        275                 280                 285

Ser Ile Ser Ser Cys Leu Gln Gln Leu Ser Leu Leu Met Trp Ile Thr
    290                 295                 300

Gln Cys Phe Leu Pro Val Phe Leu Ala Gln Pro Pro Ser Gly Gln Arg
305                 310                 315                 320

Arg His His His His His His
                325
```

<210> SEQ ID NO 78
<211> LENGTH: 1212
<212> TYPE: DNA
<213> ORGANISM: Homo Sapien

<400> SEQUENCE: 78

| | | | | | |
|---|---|---|---|---|---|
| atggatccaa | gcagccattc | atcaaatatg | gcgaataccc | aaatgaaatc | agacaaaatc | 60 |
| attattgctc | accgtggtgc | tagcggttat | ttaccagagc | atacgttaga | atctaaagca | 120 |
| cttgcgtttg | cacaacaggc | tgattattta | gagcaagatt | tagcaatgac | taaggatggt | 180 |
| cgtttagtgg | ttattcacga | tcacttttta | gatggcttga | ctgatgttgc | gaaaaaattc | 240 |
| ccacatcgtc | atcgtaaaga | tggccgttac | tatgtcatcg | actttacctt | aaaagaaatt | 300 |
| caaagtttag | aaatgacaga | aaactttgaa | accgcggccg | cacatatgca | ggcggaaggc | 360 |
| cgtggtactg | gcggtagcac | cggcgatgca | gatggtccgg | gcggtccggg | tattccggat | 420 |
| ggtccgggtg | gtaatgcagg | tggtccaggt | gaagcaggtg | cgactggcgg | tcgtggtcca | 480 |
| cgcggtgcag | gtgcagcgcg | tgcatctggt | ccaggtggcg | gtgcgccgcg | tggcccgcat | 540 |
| ggtggtgcag | ctagtgcgca | agatggtcgt | tgcccgtgtg | gtgcgcgtcg | tccggatagc | 600 |
| cgtctgctgg | agctgcatat | taccatgccg | tttagcagcc | caatgaaagc | tgagctggtg | 660 |
| cgtcgtattc | tgtctcgtga | cgcagcaccg | ctgccacgtc | cgggtgcggt | tctgaaagat | 720 |
| tttaccgtga | gcggcaacct | gctgtttatt | cgtctgaccg | cggcagatca | tcgtcagctg | 780 |
| caactgagca | ttagcagctg | cctgcaacag | ctgtctctgc | tgatgtggat | tacccagtgc | 840 |
| tttctgccgg | tgtttctggc | tcaggcgccg | tctggtcagc | gtcgtggtgg | tgcccgtggc | 900 |
| ccggaatctc | gtctgctgga | attttatctg | gccatgccgt | tcgcgacgcc | gatggaagca | 960 |
| gagctggccc | gtcgcagcct | ggctcaggat | gcaccgccgc | tgccggttcc | gggcgtgctg | 1020 |
| ctgaaagaat | ttacggttag | cggtaacatt | ctgaccatcc | gtctgaccgc | agcggaccac | 1080 |
| cgccaactgc | aactgtctat | cagctcttgc | ctgcaacaac | tgtcgttatt | aatgtggatc | 1140 |
| actcaatgtt | ttttaccagt | attcctggcc | caaccgccga | gcggccaacg | tcgtcaccac | 1200 |
| caccaccacc | ac | | | | | 1212 |

<210> SEQ ID NO 79
<211> LENGTH: 404
<212> TYPE: PRT
<213> ORGANISM: Homo Sapien

<400> SEQUENCE: 79

Met Asp Pro Ser Ser His Ser Ser Asn Met Ala Asn Thr Gln Met Lys
 1               5                  10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Ala
            100                 105                 110

Ala Ala His Met Gln Ala Glu Gly Arg Gly Thr Gly Gly Ser Thr Gly
        115                 120                 125

Asp Ala Asp Gly Pro Gly Gly Pro Gly Ile Pro Asp Gly Pro Gly Gly
     130                 135                 140

Asn Ala Gly Gly Pro Gly Glu Ala Gly Ala Thr Gly Gly Arg Gly Pro
145                 150                 155                 160

Arg Gly Ala Gly Ala Ala Arg Ala Ser Gly Pro Gly Gly Ala Pro
            165                 170                 175

Arg Gly Pro His Gly Gly Ala Ala Ser Ala Gln Asp Gly Arg Cys Pro
            180                 185                 190

Cys Gly Ala Arg Arg Pro Asp Ser Arg Leu Leu Glu Leu His Ile Thr
            195                 200                 205

Met Pro Phe Ser Ser Pro Met Glu Ala Glu Leu Val Arg Arg Ile Leu
    210                 215                 220

Ser Arg Asp Ala Ala Pro Leu Pro Arg Pro Gly Ala Val Leu Lys Asp
225                 230                 235                 240

Phe Thr Val Ser Gly Asn Leu Leu Phe Ile Arg Leu Thr Ala Ala Asp
                245                 250                 255

His Arg Gln Leu Gln Leu Ser Ile Ser Ser Cys Leu Gln Gln Leu Ser
            260                 265                 270

Leu Leu Met Trp Ile Thr Gln Cys Phe Leu Pro Val Phe Leu Ala Gln
        275                 280                 285

Ala Pro Ser Gly Gln Arg Arg Gly Gly Ala Arg Gly Pro Glu Ser Arg
290                 295                 300

Leu Leu Glu Phe Tyr Leu Ala Met Pro Phe Ala Thr Pro Met Glu Ala
305                 310                 315                 320

Glu Leu Ala Arg Arg Ser Leu Ala Gln Asp Ala Pro Pro Leu Pro Val
            325                 330                 335

Pro Gly Val Leu Leu Lys Glu Phe Thr Val Ser Gly Asn Ile Leu Thr
            340                 345                 350

Ile Arg Leu Thr Ala Ala Asp His Arg Gln Leu Gln Leu Ser Ile Ser
            355                 360                 365

Ser Cys Leu Gln Gln Leu Ser Leu Leu Met Trp Ile Thr Gln Cys Phe
        370                 375                 380

Leu Pro Val Phe Leu Ala Gln Pro Pro Ser Gly Gln Arg Arg His His
385                 390                 395                 400

His His His His

<210> SEQ ID NO 80
<211> LENGTH: 918
<212> TYPE: DNA
<213> ORGANISM: Homo Sapien

<400> SEQUENCE: 80
atgggccatc atcatcatca tcatcatcat catcacagca gcggccatat cgacgacgac     60
gacaagcata tgcaggcgga aggccgtggt actggcggta gcaccggcga tgcagatggt    120
ccgggcggtc cgggtattcc ggatggtccg ggtggtaatg caggtggtcc aggtgaagca    180
ggtgcgactg gcggtcgtgg tccacgcggt gcaggtgcag cgcgtgcatc tggtccaggt    240
ggcggtgcgc gcgtggccc gcatggtggt gcagctagtg cgcaagatgg tcgttgcccg     300
tgtggtgcgc gtcgtccgga tagccgtctg ctggagctgc atattaccat gccgtttagc    360
agcccaatgg aagctgagct ggtgcgtcgt attctgtctc gtgacgcagc accgctgcca    420
cgtccgggtg cggttctgaa agattttacc gtgagcggca acctgctgtt tattcgtctg    480
accgcggcag atcatcgtca gctgcaactg agcattagca gctgcctgca acagctgtct    540

```
ctgctgatgt ggattaccca gtgctttctg ccggtgtttc tggctcaggc gccgtctggt    600
cagcgtcgtg gtggtgcccg tggcccggaa tctcgtctgc tggaatttta tctggccatg    660
ccgttcgcga cgccgatgga agcagagctg gcccgtcgca gcctggctca ggatgcaccg    720
ccgctgccgt tccgggcgt gctgctgaaa gaatttacgg ttagcggtaa cattctgacc    780
atccgtctga ccgcagcgga ccaccgccaa ctgcaactgt ctatcagctc ttgcctgcaa    840
caactgtcgt tattaatgtg gatcactcaa tgttttttac cagtattcct ggcccaaccg    900
ccgagcggcc aacgtcgt                                                   918

<210> SEQ ID NO 81
<211> LENGTH: 306
<212> TYPE: PRT
<213> ORGANISM: Homo Sapien

<400> SEQUENCE: 81

Met Gly His His His His His His His His Ser Ser Gly His
 1               5                  10                  15

Ile Asp Asp Asp Lys His Met Gln Ala Glu Gly Arg Gly Thr Gly
                20                  25                  30

Gly Ser Thr Gly Asp Ala Asp Gly Pro Gly Gly Pro Gly Ile Pro Asp
            35                  40                  45

Gly Pro Gly Gly Asn Ala Gly Gly Pro Gly Glu Ala Gly Ala Thr Gly
        50                  55                  60

Gly Arg Gly Pro Arg Gly Ala Gly Ala Ala Arg Ala Ser Gly Pro Gly
    65                  70                  75                  80

Gly Gly Ala Pro Arg Gly Pro His Gly Gly Ala Ala Ser Ala Gln Asp
                85                  90                  95

Gly Arg Cys Pro Cys Gly Ala Arg Arg Pro Asp Ser Arg Leu Leu Glu
            100                 105                 110

Leu His Ile Thr Met Pro Phe Ser Ser Pro Met Glu Ala Glu Leu Val
        115                 120                 125

Arg Arg Ile Leu Ser Arg Asp Ala Ala Pro Leu Pro Arg Pro Gly Ala
    130                 135                 140

Val Leu Lys Asp Phe Thr Val Ser Gly Asn Leu Leu Phe Ile Arg Leu
145                 150                 155                 160

Thr Ala Ala Asp His Arg Gln Leu Gln Leu Ser Ile Ser Ser Cys Leu
                165                 170                 175

Gln Gln Leu Ser Leu Leu Met Trp Ile Thr Gln Cys Phe Leu Pro Val
            180                 185                 190

Phe Leu Ala Gln Ala Pro Ser Gly Gln Arg Arg Gly Gly Ala Arg Gly
        195                 200                 205

Pro Glu Ser Arg Leu Leu Glu Phe Tyr Leu Ala Met Pro Phe Ala Thr
    210                 215                 220

Pro Met Glu Ala Glu Leu Ala Arg Arg Ser Leu Ala Gln Asp Ala Pro
225                 230                 235                 240

Pro Leu Pro Val Pro Gly Val Leu Leu Lys Glu Phe Thr Val Ser Gly
                245                 250                 255

Asn Ile Leu Thr Ile Arg Leu Thr Ala Ala Asp His Arg Gln Leu Gln
            260                 265                 270

Leu Ser Ile Ser Ser Cys Leu Gln Gln Leu Ser Leu Leu Met Trp Ile
        275                 280                 285

Thr Gln Cys Phe Leu Pro Val Phe Leu Ala Gln Pro Pro Ser Gly Gln
    290                 295                 300

Arg Arg
```

<210> SEQ ID NO 82
<211> LENGTH: 684
<212> TYPE: DNA
<213> ORGANISM: Homo Sapien

<400> SEQUENCE: 82

```
atgggccatc atcatcatca tcatcatcat catcacagca gcggccatat cgacgacgac      60
gacaagcata tgggtgcgcg tggtccggaa agccgtctgc tggaattta tctggccatg     120
ccgtttgcga ccccgatgga agcggaactg gcccgtcgta gcctggctca agatgcaccg     180
ccgctgccgg ttccgggcgt gctgctgaaa gaatttaccg tgagcggcaa cattctgacc     240
attcgtctga cggcggcaga ccatcgtcag ctgcaactga gcattagcag ctgcctgcaa     300
cagctgtctc tgctgatgtg gattacccag tgctttctgc cggtgtttct ggcccagccg     360
ccgtctggtc aacgtggtgg cgcgcgtcgt ccggattctc gcctgctgga actgcatatt     420
accatgccgt tcagctctcc aatggaggcc gaattagtgc gtcgcattct gagccgtgat     480
gcggcaccgc tgccgcgtcc aggtgcggtt ctgaaagact tcaccgtatc tggcaacctg     540
ctgtttatcc gtctgaccgc agcggaccac cgccaattac aattatctat cagctcttgt     600
ttacaacaac tgtcgctgtt aatgtggatc actcaatgtt tcctgccagt attcctggct     660
caggccccga gcggtcagcg tcgt                                             684
```

<210> SEQ ID NO 83
<211> LENGTH: 228
<212> TYPE: PRT
<213> ORGANISM: Homo Sapien

<400> SEQUENCE: 83

Met Gly His His His His His His His His Ser Gly His
 1               5                   10                  15

Ile Asp Asp Asp Asp Lys His Met Gly Ala Arg Gly Pro Glu Ser Arg
             20                  25                  30

Leu Leu Glu Phe Tyr Leu Ala Met Pro Phe Ala Thr Pro Met Glu Ala
         35                  40                  45

Glu Leu Ala Arg Arg Ser Leu Ala Gln Asp Ala Pro Pro Leu Pro Val
     50                  55                  60

Pro Gly Val Leu Leu Lys Glu Phe Thr Val Ser Gly Asn Ile Leu Thr
 65                  70                  75                  80

Ile Arg Leu Thr Ala Ala Asp His Arg Gln Leu Gln Leu Ser Ile Ser
                 85                  90                  95

Ser Cys Leu Gln Gln Leu Ser Leu Leu Met Trp Ile Thr Gln Cys Phe
            100                 105                 110

Leu Pro Val Phe Leu Ala Gln Pro Pro Ser Gly Gln Arg Gly Gly Ala
        115                 120                 125

Arg Arg Pro Asp Ser Arg Leu Leu Glu Leu His Ile Thr Met Pro Phe
    130                 135                 140

Ser Ser Pro Met Glu Ala Glu Leu Val Arg Arg Ile Leu Ser Arg Asp
145                 150                 155                 160

Ala Ala Pro Leu Pro Arg Pro Gly Ala Val Leu Lys Asp Phe Thr Val
                165                 170                 175

Ser Gly Asn Leu Leu Phe Ile Arg Leu Thr Ala Ala Asp His Arg Gln
            180                 185                 190

Leu Gln Leu Ser Ile Ser Ser Cys Leu Gln Gln Leu Ser Leu Leu Met
        195                 200                 205

Trp Ile Thr Gln Cys Phe Leu Pro Val Phe Leu Ala Gln Ala Pro Ser
    210                 215                 220

Gly Gln Arg Arg
225

<210> SEQ ID NO 84
<211> LENGTH: 915
<212> TYPE: DNA
<213> ORGANISM: Homo Sapien

<400> SEQUENCE: 84
atgggccatc atcatcatca tcatcatcat catcacagca gcggccatat cgacgacgac    60
gacaagcata tgcaggcgga aggccgtggc accggtggta gcaccggcga tgcggatggt   120 ccggcggtc cgggtattcc ggacgggcct ggtggtaatg cgggtgggcc aggtgaagcg   180
ggtgcgaccg gtggtcgtgg tccgcggggg gcaggcgcag cacgtgcatc tggtccgggt   240
ggtggtgcac cgcgcggtcc gcatggtggt gcggcgagcg gcctgaatgg ttgctgccgt   300
tgcggtgcgc gtggtccgga aagccgtctg ctggaatttt atctggccat gccgtttgcg   360
accccgatgg aagcggaact ggcccgtcgt agcctggctc aagatgcacc gccgctgccg   420
gttccgggcg tgctgctgaa agaatttacc gtgagcggca acattctgac cattcgtctg   480
acggcggcag accatcgtca gctgcaactg agcattagca gctgcctgca acagctgtct   540
ctgctgatgt ggattaccca gtgctttctg ccggtgtttc tggcccagcc gccgtctggt   600
caacgtggtg gcgcgcgtcg tccggattct cgcctgctgg aactgcatat taccatgccg   660
ttcagctctc caatggaggc cgaattagtg cgtcgcattc tgagccgtga tgcggcaccg   720
ctgccgcgtc aggtgcggt tctgaaagac ttcaccgtat ctggcaacct gctgtttatc   780
cgtctgaccg cagcggacca ccgccaatta caattatcta tcagctcttg tttacaacaa   840
ctgtcgctgt taatgtggat cactcaatgt ttcctgccag tattcctggc tcaggccccg   900
agcggtcagc gtcgt                                                    915

<210> SEQ ID NO 85
<211> LENGTH: 305
<212> TYPE: PRT
<213> ORGANISM: Homo Sapien

<400> SEQUENCE: 85

Met Gly His His His His His His His His Ser Ser Gly His
  1               5                  10                  15

Ile Asp Asp Asp Asp Lys His Met Gln Ala Glu Gly Arg Gly Thr Gly
                 20                  25                  30

Gly Ser Thr Gly Asp Ala Asp Gly Pro Gly Gly Pro Gly Ile Pro Asp
             35                  40                  45

Gly Pro Gly Gly Asn Ala Gly Gly Pro Gly Glu Ala Gly Ala Thr Gly
         50                  55                  60

Gly Arg Gly Pro Arg Gly Ala Gly Ala Ala Arg Ala Ser Gly Pro Gly
 65                  70                  75                  80

Gly Gly Ala Pro Arg Gly Pro His Gly Gly Ala Ala Ser Gly Leu Asn
                 85                  90                  95

Gly Cys Cys Arg Cys Gly Ala Arg Gly Pro Glu Ser Arg Leu Leu Glu
            100                 105                 110

Phe Tyr Leu Ala Met Pro Phe Ala Thr Pro Met Glu Ala Glu Leu Ala
        115                 120                 125

Arg Arg Ser Leu Ala Gln Asp Ala Pro Pro Leu Pro Val Pro Gly Val

```
                  130                 135                 140
Leu Leu Lys Glu Phe Thr Val Ser Gly Asn Ile Leu Thr Ile Arg Leu
145                 150                 155                 160

Thr Ala Ala Asp His Arg Gln Leu Gln Leu Ser Ile Ser Ser Cys Leu
                165                 170                 175

Gln Gln Leu Ser Leu Leu Met Trp Ile Thr Gln Cys Phe Leu Pro Val
            180                 185                 190

Phe Leu Ala Gln Pro Pro Ser Gly Gln Arg Gly Gly Ala Arg Arg Pro
        195                 200                 205

Asp Ser Arg Leu Leu Glu Leu His Ile Thr Met Pro Phe Ser Ser Pro
    210                 215                 220

Met Glu Ala Glu Leu Val Arg Arg Ile Leu Ser Arg Asp Ala Ala Pro
225                 230                 235                 240

Leu Pro Arg Pro Gly Ala Val Leu Lys Asp Phe Thr Val Ser Gly Asn
                245                 250                 255

Leu Leu Phe Ile Arg Leu Thr Ala Ala Asp His Arg Gln Leu Gln Leu
            260                 265                 270

Ser Ile Ser Ser Cys Leu Gln Gln Leu Ser Leu Leu Met Trp Ile Thr
        275                 280                 285

Gln Cys Phe Leu Pro Val Phe Leu Ala Gln Ala Pro Ser Gly Gln Arg
    290                 295                 300

Arg
305

<210> SEQ ID NO 86
<211> LENGTH: 687
<212> TYPE: DNA
<213> ORGANISM: Homo Sapien

<400> SEQUENCE: 86
atgggccatc atcatcatca tcatcatcat catcacagca gcggccatat cgacgacgac      60
gacaagcata tgggtgcgcg tcgtccggat agccgtctgc tggagctgca tattaccatg     120
ccgtttagca gcccaatgga agctgagctg gtgcgtcgta ttctgtctcg tgacgcagca     180
ccgctgccac gtccgggtgc ggttctgaaa gattttaccg tgagcggcaa cctgctgttt     240
attcgtctga ccgcggcaga tcatcgtcag ctgcaactga gcattagcag ctgcctgcaa     300
cagctgtctc tgctgatgtg gattacccag tgctttctgc cggtgtttct ggctcaggcg     360
ccgtctggtc agcgtcgtgg tggtgcccgt ggcccggaat ctcgtctgct ggaattttat     420
ctggccatgc cgttcgcgac gccgatggaa gcagagctgg cccgtcgcag cctggctcag     480
gatgcaccgc cgctgccggt tccgggcgtg ctgctgaaag aatttacggt tagcggtaac     540
attctgacca tccgtctgac cgcagcggac caccgccaac tgcaactgtc tatcagctct     600
tgcctgcaac aactgtcgtt attaatgtgg atcactcaat gttttttacc agtattcctg     660
gcccaaccgc cgagcggcca acgtcgt                                         687

<210> SEQ ID NO 87
<211> LENGTH: 229
<212> TYPE: PRT
<213> ORGANISM: Homo Sapien

<400> SEQUENCE: 87

Met Gly His His His His His His His His Ser Ser Gly His
1               5                   10                  15

Ile Asp Asp Asp Asp Lys His Met Gly Ala Arg Arg Pro Asp Ser Arg
            20                  25                  30
```

```
Leu Leu Glu Leu His Ile Thr Met Pro Phe Ser Ser Pro Met Glu Ala
             35                  40                  45
Glu Leu Val Arg Arg Ile Leu Ser Arg Asp Ala Ala Pro Leu Pro Arg
 50                  55                  60
Pro Gly Ala Val Leu Lys Asp Phe Thr Val Ser Gly Asn Leu Leu Phe
 65                  70                  75                  80
Ile Arg Leu Thr Ala Ala Asp His Arg Gln Leu Gln Leu Ser Ile Ser
                 85                  90                  95
Ser Cys Leu Gln Gln Leu Ser Leu Leu Met Trp Ile Thr Gln Cys Phe
                100                 105                 110
Leu Pro Val Phe Leu Ala Gln Ala Pro Ser Gly Gln Arg Gly Arg Gly
                115                 120                 125
Ala Arg Gly Pro Glu Ser Arg Leu Leu Glu Phe Tyr Leu Ala Met Pro
            130                 135                 140
Phe Ala Thr Pro Met Glu Ala Glu Leu Ala Arg Arg Ser Leu Ala Gln
145                 150                 155                 160
Asp Ala Pro Pro Leu Pro Val Pro Gly Val Leu Leu Lys Glu Phe Thr
                165                 170                 175
Val Ser Gly Asn Ile Leu Thr Ile Arg Leu Thr Ala Ala Asp His Arg
                180                 185                 190
Gln Leu Gln Leu Ser Ile Ser Ser Cys Leu Gln Leu Ser Leu Leu
            195                 200                 205
Met Trp Ile Thr Gln Cys Phe Leu Pro Val Phe Leu Ala Gln Pro Pro
210                 215                 220
Ser Gly Gln Arg Arg
225

<210> SEQ ID NO 88
<211> LENGTH: 1197
<212> TYPE: DNA
<213> ORGANISM: Homo Sapien

<400> SEQUENCE: 88
atggatccaa gcagccattc atcaaatatg gcgaatactc aaatgaaatc agacaaaatc        60
attattgctc accgtggtgc tagcggttat ttaccagagc atacgttaga atctaaagca       120
cttgcgtttg cacaacaggc tgattattta gagcaagatt tagcaatgac taaggatggt       180
cgtttagtgg ttattcacga tcactttta gatggcttga ctgatgttgc gaaaaaattc       240
ccacatcgtc atcgtaaaga tggccgttac tatgtcatcg actttacctt aaaagaaatt       300
caaagtttag aaatgacaga aaactttgaa acccaggcgg aaggccgtgg tactggcggt       360
agcaccggcg atgcagatgg tccgggcggt ccgggtattc cggatggtcc gggtggtaat       420
gcaggtggtc caggtgaagc aggtgcgact ggcggtcgtg gtccacgcgg tgcaggtgca       480
gcgcgtgcat ctggtccagg tgcggtgcg ccgcgtggcc cgcatggtgg tgcagctagt       540
gcgcaagatg gtcgttgccc gtgtggtgcg cgtcgtccgg atagccgtct gctggagctg       600
catattacca tgccgtttag cagcccaatg gaagctgagc tggtgcgtcg tattctgtct       660
cgtgacgcag caccgctgcc acgtccgggt gcggttctga agattttac cgtgagcggc       720
aacctgctgt ttattcgtct gaccgcggca gatcatcgtc agctgcaact gagcattagc       780
agctgcctgc aacagctgtc tctgctgatg tggattaccc agtgctttct gccggtgttt       840
ctggctcagg cgccgtctgg tcagcgtcgt ggtggtgccc gtggccggga atctcgtctg       900
ctggaatttt atctggccat gccgttcgcg acgccgatgg aagcagagct ggcccgtcgc       960
```

```
agcctggctc aggatgcacc gccgctgccg gttccgggcg tgctgctgaa agaatttacg    1020
gttagcggta acattctgac catccgtctg accgcagcgg accaccgcca actgcaactg    1080
tctatcagct cttgcctgca acaactgtcg ttattaatgt ggatcactca atgttttta    1140 ccagtattcc tggcccaacc gccgagcggc aacgtcgtc accaccacca ccaccac       1197
```

<210> SEQ ID NO 89
<211> LENGTH: 399
<212> TYPE: PRT
<213> ORGANISM: Homo Sapien

<400> SEQUENCE: 89

```
Met Asp Pro Ser Ser His Ser Ser Asn Met Ala Asn Thr Gln Met Lys
 1               5                  10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Gln
            100                 105                 110

Ala Glu Gly Arg Gly Thr Gly Gly Ser Thr Gly Asp Ala Asp Gly Pro
        115                 120                 125

Gly Gly Pro Gly Ile Pro Asp Gly Pro Gly Gly Asn Ala Gly Gly Pro
    130                 135                 140

Gly Glu Ala Gly Ala Thr Gly Gly Arg Gly Pro Arg Gly Ala Gly Ala
145                 150                 155                 160

Ala Arg Ala Ser Gly Pro Gly Gly Gly Ala Pro Arg Gly Pro His Gly
                165                 170                 175

Gly Ala Ala Ser Ala Gln Asp Gly Arg Cys Pro Cys Gly Ala Arg Arg
            180                 185                 190

Pro Asp Ser Arg Leu Leu Glu Leu His Ile Thr Met Pro Phe Ser Ser
        195                 200                 205

Pro Met Glu Ala Glu Leu Val Arg Arg Ile Leu Ser Arg Asp Ala Ala
    210                 215                 220

Pro Leu Pro Arg Pro Gly Ala Val Leu Lys Asp Phe Thr Val Ser Gly
225                 230                 235                 240

Asn Leu Leu Phe Ile Arg Leu Thr Ala Ala Asp His Arg Gln Leu Gln
                245                 250                 255

Leu Ser Ile Ser Ser Cys Leu Gln Gln Leu Ser Leu Leu Met Trp Ile
            260                 265                 270

Thr Gln Cys Phe Leu Pro Val Phe Leu Ala Gln Ala Pro Ser Gly Gln
        275                 280                 285

Arg Arg Gly Gly Ala Arg Gly Pro Glu Ser Arg Leu Leu Glu Phe Tyr
    290                 295                 300

Leu Ala Met Pro Phe Ala Thr Pro Met Glu Ala Glu Leu Ala Arg Arg
305                 310                 315                 320

Ser Leu Ala Gln Asp Ala Pro Pro Leu Pro Val Pro Gly Val Leu Leu
                325                 330                 335

Lys Glu Phe Thr Val Ser Gly Asn Ile Leu Thr Ile Arg Leu Thr Ala
```

340                 345                 350
Ala Asp His Arg Gln Leu Gln Leu Ser Ile Ser Ser Cys Leu Gln Gln
            355                 360                 365

Leu Ser Leu Leu Met Trp Ile Thr Gln Cys Phe Leu Pro Val Phe Leu
        370                 375                 380

Ala Gln Pro Pro Ser Gly Gln Arg Arg His His His His His His
385                 390                 395

<210> SEQ ID NO 90
<211> LENGTH: 1194
<212> TYPE: DNA
<213> ORGANISM: Homo Sapien

<400> SEQUENCE: 90
atggatccaa gcagccattc atcaaatatg gcgaatacccc aaatgaaatc agacaaaatc    60
attattgctc accgtggtgc tagcggttat ttaccagagc atacgttaga atctaaagca   120
cttgcgtttg cacaacaggc tgattattta gagcaagatt tagcaatgac taaggatggt   180
cgtttagtgg ttattcacga tcactttta gatggcttga ctgatgttgc gaaaaaattc   240
ccacatcgtc atcgtaaaga tggccgttac tatgtcatcg actttacctt aaaagaaatt   300
caaagtttag aaatgacaga aactttgaa acccaggcgg aaggccgtgg caccggtggt   360
agcaccggcg atgcggatgg tccgggcggt ccgggtattc cggacgggcc tggtggtaat   420
gcgggtgggc caggtgaagc gggtgcgacc ggtggtcgtg gtccgcgggg ggcaggcgca   480
gcacgtgcat ctggtccggg tggtggtgca ccgcgcggtc gcatggtgg tcggcgagc   540 ggcctgaatg gttgctgccg ttgcggtgcg cgtggtccgg aaagccgtct gctggaattt   600
tatctggcca tgccgtttgc gaccccgatg gaagcggaac tggcccgtcg tagcctggct   660
caagatgcac cgccgctgcc ggttccgggc gtgctgctga agaatttac cgtgagcggc   720 aacattctga ccattcgtct gacggcggca gaccatcgtc agctgcaact gagcattagc   780
agctgcctgc aacagctgtc tctgctgatg tggattaccc agtgctttct gccggtgttt   840
ctggcccagc cgccgtctgg tcaacgtggt ggcgcgcgtc gtccggattc tcgcctgctg   900
gaactgcata ttaccatgcc gttcagctct ccaatggagg ccgaattagt gcgtcgcatt   960
ctgagccgtg atgcggcacc gctgccgcgt ccaggtgcgg ttctgaaaga cttcaccgta  1020
tctggcaacc tgctgtttat ccgtctgacc gcagcggacc accgcaatt acaattatct  1080 atcagctctt gtttacaaca actgtcgctg ttaatgtgga tcactcaatg tttcctgcca  1140
gtattcctgg ctcaggcccc gagcggtcag cgtcgtcacc accaccacca ccac         1194

<210> SEQ ID NO 91
<211> LENGTH: 398
<212> TYPE: PRT
<213> ORGANISM: Homo Sapien

<400> SEQUENCE: 91

Met Asp Pro Ser Ser His Ser Ser Asn Met Ala Asn Thr Gln Met Lys
1               5                   10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe

```
                65                  70                  75                  80
Pro His Arg His Arg Lys Asp Gly Arg Tyr Tyr Val Ile Asp Phe Thr
                        85                  90                  95
Leu Lys Glu Ile Gln Ser Leu Glu Met Thr Glu Asn Phe Glu Thr Gln
                    100                 105                 110
Ala Glu Gly Arg Gly Thr Gly Gly Ser Thr Gly Asp Ala Asp Gly Pro
                115                 120                 125
Gly Gly Pro Gly Ile Pro Asp Gly Pro Gly Asn Ala Gly Gly Pro
            130                 135                 140
Gly Glu Ala Gly Ala Thr Gly Gly Arg Gly Pro Arg Gly Ala Gly Ala
145                 150                 155                 160
Ala Arg Ala Ser Gly Pro Gly Gly Ala Pro Arg Gly Pro His Gly
                165                 170                 175
Gly Ala Ala Ser Gly Leu Asn Gly Cys Arg Cys Gly Ala Arg Gly
                180                 185                 190
Pro Glu Ser Arg Leu Leu Glu Phe Tyr Leu Ala Met Pro Phe Ala Thr
                195                 200                 205
Pro Met Glu Ala Glu Leu Ala Arg Arg Ser Leu Ala Gln Asp Ala Pro
    210                 215                 220
Pro Leu Pro Val Pro Gly Val Leu Leu Lys Glu Phe Thr Val Ser Gly
225                 230                 235                 240
Asn Ile Leu Thr Ile Arg Leu Thr Ala Ala Asp His Arg Gln Leu Gln
                    245                 250                 255
Leu Ser Ile Ser Ser Cys Leu Gln Gln Leu Ser Leu Leu Met Trp Ile
                260                 265                 270
Thr Gln Cys Phe Leu Pro Val Phe Leu Ala Gln Pro Pro Ser Gly Gln
            275                 280                 285
Arg Gly Gly Ala Arg Arg Pro Asp Ser Arg Leu Leu Glu Leu His Ile
    290                 295                 300
Thr Met Pro Phe Ser Ser Pro Met Glu Ala Glu Leu Val Arg Arg Ile
305                 310                 315                 320
Leu Ser Arg Asp Ala Ala Pro Leu Pro Arg Pro Gly Ala Val Leu Lys
                    325                 330                 335
Asp Phe Thr Val Ser Gly Asn Leu Leu Phe Ile Arg Leu Thr Ala Ala
                340                 345                 350
Asp His Arg Gln Leu Gln Leu Ser Ile Ser Ser Cys Leu Gln Gln Leu
            355                 360                 365
Ser Leu Leu Met Trp Ile Thr Gln Cys Phe Leu Pro Val Phe Leu Ala
    370                 375                 380
Gln Ala Pro Ser Gly Gln Arg Arg His His His His His
385                 390                 395

<210> SEQ ID NO 92
<211> LENGTH: 867
<212> TYPE: DNA
<213> ORGANISM: Homo Sapien

<400> SEQUENCE: 92
atgcatcatc atcatcatca ccaggcggaa ggccgtggta ctggcggtag caccggcgat      60
gcagatggtc cgggcggtcc gggtattccg gatggtccgg gtggtaatgc aggtggtcca     120
ggtgaagcag gtgcgactgg cggtcgtggt ccacgcggtg caggtgcagc gcgtgcatct     180
ggtccaggtg gcggtgcgcc gcgtggcccg catggtggtg cagctagtgc gcaagatggt     240
cgttgcccgt gtggtgcgcg tcgtccggat agccgtctgc tggagctgca tattaccatg     300
```

```
ccgtttagca gcccaatgga agctgagctg gtgcgtcgta ttctgtctcg tgacgcagca    360
ccgctgccac gtccgggtgc ggttctgaaa gattttaccg tgagcggcaa cctgctgttt    420
attcgtctga ccgcggcaga tcatcgtcag ctgcaactga gcattagcag ctgcctgcaa    480
cagctgtctc tgctgatgtg gattacccag tgctttctgc cggtgtttct ggctcaggcg    540
ccgtctggtc agcgtcgtgg tggtgcccgt ggcccggaat ctcgtctgct ggaattttat    600
ctggccatgc cgttcgcgac gccgatgaaa gcagagctgg cccgtcgcag cctggctcag    660
gatgcaccgc cgctgccggt tccgggcgtg ctgctgaaag aatttacggt tagcggtaac    720
attctgacca tccgtctgac cgcagcggac caccgccaac tgcaactgtc tatcagctct    780
tgcctgcaac aactgtcgtt attaatgtgg atcactcaat gttttttacc agtattcctg    840
gcccaaccgc cgagcggcca acgtcgt                                        867
```

<210> SEQ ID NO 93
<211> LENGTH: 289
<212> TYPE: PRT
<213> ORGANISM: Homo Sapien
<400> SEQUENCE: 93

```
Met His His His His His His Gln Ala Glu Gly Arg Gly Thr Gly Gly
 1               5                  10                  15

Ser Thr Gly Asp Ala Asp Gly Pro Gly Gly Pro Gly Ile Pro Asp Gly
            20                  25                  30

Pro Gly Gly Asn Ala Gly Gly Pro Gly Glu Ala Gly Ala Thr Gly Gly
        35                  40                  45

Arg Gly Pro Arg Gly Ala Gly Ala Arg Ala Ser Gly Pro Gly Gly
    50                  55                  60

Gly Ala Pro Arg Gly Pro His Gly Gly Ala Ala Ser Ala Gln Asp Gly
65                  70                  75                  80

Arg Cys Pro Cys Gly Ala Arg Arg Pro Asp Ser Arg Leu Leu Glu Leu
                85                  90                  95

His Ile Thr Met Pro Phe Ser Ser Pro Met Glu Ala Glu Leu Val Arg
            100                 105                 110

Arg Ile Leu Ser Arg Asp Ala Ala Pro Leu Pro Arg Pro Gly Ala Val
        115                 120                 125

Leu Lys Asp Phe Thr Val Ser Gly Asn Leu Leu Phe Ile Arg Leu Thr
    130                 135                 140

Ala Ala Asp His Arg Gln Leu Gln Leu Ser Ile Ser Ser Cys Leu Gln
145                 150                 155                 160

Gln Leu Ser Leu Leu Met Trp Ile Thr Gln Cys Phe Leu Pro Val Phe
                165                 170                 175

Leu Ala Gln Ala Pro Ser Gly Gln Arg Arg Gly Gly Ala Arg Gly Pro
            180                 185                 190

Glu Ser Arg Leu Leu Glu Phe Tyr Leu Ala Met Pro Phe Ala Thr Pro
        195                 200                 205

Met Glu Ala Glu Leu Ala Arg Arg Ser Leu Ala Gln Asp Ala Pro Pro
    210                 215                 220

Leu Pro Val Pro Gly Val Leu Leu Lys Glu Phe Thr Val Ser Gly Asn
225                 230                 235                 240

Ile Leu Thr Ile Arg Leu Thr Ala Ala Asp His Arg Gln Leu Gln Leu
                245                 250                 255

Ser Ile Ser Ser Cys Leu Gln Gln Leu Ser Leu Leu Met Trp Ile Thr
            260                 265                 270

Gln Cys Phe Leu Pro Val Phe Leu Ala Gln Pro Pro Ser Gly Gln Arg
```

275                 280                 285
Arg

<210> SEQ ID NO 94
<211> LENGTH: 633
<212> TYPE: DNA
<213> ORGANISM: Homo Sapien

<400> SEQUENCE: 94
atgcatcatc atcatcatca cggtgcgcgt ggtccggaaa gccgtctgct ggaattttat      60
ctggccatgc cgtttgcgac cccgatggaa gcggaactgg cccgtcgtag cctggctcaa     120
gatgcaccgc cgctgccggt tccgggcgtg ctgctgaaag aatttaccgt gagcggcaac     180
attctgacca ttcgtctgac ggcggcagac catcgtcagc tgcaactgag cattagcagc     240
tgcctgcaac agctgtctct gctgatgtgg attacccagt gctttctgcc ggtgtttctg     300
gcccagccgc cgtctggtca acgtggtggc gcgcgtcgtc cggattctcg cctgctggaa     360
ctgcatatta ccatgccgtt cagctctcca atggaggccg aattagtgcg tcgcattctg     420
agccgtgatg cggcaccgct gccgcgtcca ggtgcggttc tgaaagactt caccgtatct     480
ggcaacctgc tgtttatccg tctgaccgca gcggaccacc gccaattaca attatctatc     540
agctcttgtt tacaacaact gtcgctgtta atgtggatca ctcaatgttt cctgccagta     600
ttcctggctc aggccccgag cggtcagcgt cgt                                  633

<210> SEQ ID NO 95
<211> LENGTH: 211
<212> TYPE: PRT
<213> ORGANISM: Homo Sapien

<400> SEQUENCE: 95

Met His His His His His His Gly Ala Arg Gly Pro Glu Ser Arg Leu
  1               5                  10                  15

Leu Glu Phe Tyr Leu Ala Met Pro Phe Ala Thr Pro Met Glu Ala Glu
             20                  25                  30

Leu Ala Arg Arg Ser Leu Ala Gln Asp Ala Pro Pro Leu Pro Val Pro
         35                  40                  45

Gly Val Leu Leu Lys Glu Phe Thr Val Ser Gly Asn Ile Leu Thr Ile
     50                  55                  60

Arg Leu Thr Ala Ala Asp His Arg Gln Leu Gln Leu Ser Ile Ser Ser
 65                  70                  75                  80

Cys Leu Gln Gln Leu Ser Leu Leu Met Trp Ile Thr Gln Cys Phe Leu
                 85                  90                  95

Pro Val Phe Leu Ala Gln Pro Pro Ser Gly Gln Arg Gly Gly Ala Arg
            100                 105                 110

Arg Pro Asp Ser Arg Leu Leu Glu Leu His Ile Thr Met Pro Phe Ser
        115                 120                 125

Ser Pro Met Glu Ala Glu Leu Val Arg Arg Ile Leu Ser Arg Asp Ala
    130                 135                 140

Ala Pro Leu Pro Arg Pro Gly Ala Val Leu Lys Asp Phe Thr Val Ser
145                 150                 155                 160

Gly Asn Leu Leu Phe Ile Arg Leu Thr Ala Ala Asp His Arg Gln Leu
                165                 170                 175

Gln Leu Ser Ile Ser Ser Cys Leu Gln Gln Leu Ser Leu Leu Met Trp
            180                 185                 190

Ile Thr Gln Cys Phe Leu Pro Val Phe Leu Ala Gln Ala Pro Ser Gly
        195                 200                 205

Gln Arg Arg
    210

<210> SEQ ID NO 96
<211> LENGTH: 864
<212> TYPE: DNA
<213> ORGANISM: Homo Sapien

<400> SEQUENCE: 96

```
atgcatcatc atcatcatca ccaggcggaa ggccgtggca ccggtggtag caccggcgat      60
gcggatggtc cgggcggtcc gggtattccg gacgggcctg gtggtaatgc gggtgggcca     120
ggtgaagcgg gtgcgaccgg tggtcgtggt ccgcgggggg caggcgcagc acgtgcatct     180
ggtccgggtg gtggtgcacc gcgcggtccg catggtggtg cggcgagcgg cctgaatggt     240
tgctgccgtt gcggtgcgcg tggtccggaa agccgtctgc tggaatttta tctggccatg     300
ccgtttgcga ccccgatgga agcggaactg gcccgtcgta gcctggctca agatgcaccg     360
ccgctgccgg ttccgggcgt gctgctgaaa gaatttaccg tgagcggcaa cattctgacc     420
attcgtctga cggcggcaga ccatcgtcag ctgcaactga gcattagcag ctgcctgcaa     480
cagctgtctc tgctgatgtg gattacccag tgctttctgc cggtgtttct ggcccagccg     540
ccgtctggtc aacgtggtgg cgcgcgtcgt ccggattctc gcctgctgga actgcatatt     600
accatgccgt tcagctctcc aatggaggcc gaattagtgc gtcgcattct gagccgtgat     660
gcggcaccgc tgccgcgtcc aggtgcggtt ctgaaagact tcaccgtatc tggcaacctg     720
ctgtttatcc gtctgaccgc agcggaccac cgccaattac aattatctat cagctcttgt     780
ttacaacaac tgtcgctgtt aatgtggatc actcaatgtt tcctgccagt attcctggct     840
caggccccga gcggtcagcg tcgt                                            864
```

<210> SEQ ID NO 97
<211> LENGTH: 288
<212> TYPE: PRT
<213> ORGANISM: Homo Sapien

<400> SEQUENCE: 97

```
Met His His His His His Gln Ala Glu Gly Arg Gly Thr Gly Gly
1               5                   10                  15

Ser Thr Gly Asp Ala Asp Gly Pro Gly Gly Pro Gly Ile Pro Asp Gly
            20                  25                  30

Pro Gly Gly Asn Ala Gly Gly Pro Gly Glu Ala Gly Ala Thr Gly Gly
        35                  40                  45

Arg Gly Pro Arg Gly Ala Gly Ala Ala Arg Ala Ser Gly Pro Gly Gly
    50                  55                  60

Gly Ala Pro Arg Gly Pro His Gly Gly Ala Ala Ser Gly Leu Asn Gly
65                  70                  75                  80

Cys Cys Arg Cys Gly Ala Arg Gly Pro Glu Ser Arg Leu Leu Glu Phe
                85                  90                  95

Tyr Leu Ala Met Pro Phe Ala Thr Pro Met Glu Ala Glu Leu Ala Arg
            100                 105                 110

Arg Ser Leu Ala Gln Asp Ala Pro Leu Pro Val Pro Gly Val Leu
        115                 120                 125

Leu Lys Glu Phe Thr Val Ser Gly Asn Ile Leu Thr Ile Arg Leu Thr
    130                 135                 140

Ala Ala Asp His Arg Gln Leu Gln Leu Ser Ile Ser Ser Cys Leu Gln
145                 150                 155                 160
```

-continued

Gln Leu Ser Leu Leu Met Trp Ile Thr Gln Cys Phe Leu Pro Val Phe
            165                 170                 175

Leu Ala Gln Pro Pro Ser Gly Gln Gly Gly Ala Arg Arg Pro Asp
            180                 185                 190

Ser Arg Leu Leu Glu Leu His Ile Thr Met Pro Phe Ser Ser Pro Met
        195                 200                 205

Glu Ala Glu Leu Val Arg Arg Ile Leu Ser Arg Asp Ala Ala Pro Leu
    210                 215                 220

Pro Arg Pro Gly Ala Val Leu Lys Asp Phe Thr Val Ser Gly Asn Leu
225                 230                 235                 240

Leu Phe Ile Arg Leu Thr Ala Ala Asp His Arg Gln Leu Gln Leu Ser
                245                 250                 255

Ile Ser Ser Cys Leu Gln Gln Leu Ser Leu Leu Met Trp Ile Thr Gln
            260                 265                 270

Cys Phe Leu Pro Val Phe Leu Ala Gln Ala Pro Ser Gly Gln Arg Arg
            275                 280                 285

<210> SEQ ID NO 98
<211> LENGTH: 450
<212> TYPE: PRT
<213> ORGANISM: Artificial Sequence
<220> FEATURE:
<223> OTHER INFORMATION: Protein D-MAGE-a3-hIS

<400> SEQUENCE: 98

Met Asp Pro Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
            20                  25                  30

Ser Asp Lys Ile Ile Ile Ala His Arg Gly Ala Ser Gly Tyr Leu Pro
        35                  40                  45

Glu His Thr Leu Glu Ser Lys Ala Leu Ala Phe Ala Gln Gln Ala Asp
    50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                85                  90                  95

Pro His Arg His Arg Lys Asp Gly Arg Tyr Tyr Val Ile Asp Phe Thr
            100                 105                 110

Leu Lys Glu Ile Gln Ser Leu Glu Met Thr Glu Asn Phe Glu Thr Met
        115                 120                 125

Asp Leu Glu Gln Arg Ser Gln His Cys Lys Pro Glu Glu Gly Leu Glu
    130                 135                 140

Ala Arg Gly Glu Ala Leu Gly Leu Val Gly Ala Gln Ala Pro Ala Thr
145                 150                 155                 160

Glu Glu Gln Glu Ala Ala Ser Ser Ser Thr Leu Val Glu Val Thr
                165                 170                 175

Leu Gly Glu Val Pro Ala Ala Glu Ser Pro Asp Pro Pro Gln Ser Pro
            180                 185                 190

Gln Gly Ala Ser Ser Leu Pro Thr Thr Met Asn Tyr Pro Leu Trp Ser
        195                 200                 205

Gln Ser Tyr Glu Asp Ser Ser Asn Gln Glu Glu Gly Pro Ser Thr
    210                 215                 220

Phe Pro Asp Leu Glu Ser Glu Phe Gln Ala Ala Leu Ser Arg Lys Val
225                 230                 235                 240

Ala Glu Leu Val His Phe Leu Leu Leu Lys Tyr Arg Ala Arg Glu Pro

-continued

```
                    245                     250                     255
Val Thr Lys Ala Glu Met Leu Gly Ser Val Val Gly Asn Trp Gln Tyr
            260                     265                     270

Phe Phe Pro Val Ile Phe Ser Lys Ala Ser Ser Ser Leu Gln Leu Val
            275                     280                     285

Phe Gly Ile Glu Leu Met Glu Val Asp Pro Ile Gly His Leu Tyr Ile
            290                     295                     300

Phe Ala Thr Cys Leu Gly Leu Ser Tyr Asp Gly Leu Leu Gly Asp Asn
305                     310                     315                     320

Gln Ile Met Pro Lys Ala Gly Leu Leu Ile Ile Val Leu Ala Ile Ile
            325                     330                     335

Ala Arg Glu Gly Asp Cys Ala Pro Glu Glu Lys Ile Trp Glu Glu Leu
            340                     345                     350

Ser Val Leu Glu Val Phe Glu Gly Arg Glu Asp Ser Ile Leu Gly Asp
            355                     360                     365

Pro Lys Lys Leu Leu Thr Gln His Phe Val Gln Glu Asn Tyr Leu Glu
            370                     375                     380

Tyr Arg Gln Val Pro Gly Ser Asp Pro Ala Cys Tyr Glu Phe Leu Trp
385                     390                     395                     400

Gly Pro Arg Ala Leu Val Glu Thr Ser Tyr Val Lys Val Leu His His
            405                     410                     415

Met Val Lys Ile Ser Gly Gly Pro His Ile Ser Tyr Pro Pro Leu His
            420                     425                     430

Glu Trp Val Leu Arg Glu Gly Glu Glu Gly Gly His His His His His
            435                     440                     445

His His
    450
```